United States Patent
Ra et al.

(10) Patent No.: US 10,748,293 B2
(45) Date of Patent: *Aug. 18, 2020

(54) TOMOGRAPHY APPARATUS AND METHOD FOR RECONSTRUCTING TOMOGRAPHY IMAGE THEREOF

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Jong Beom Ra, Daejeon (KR); Seungeon Kim, Bucheon-si (KR); Kyoung-yong Lee, Hwaseong-si (KR); Toshihiro Rifu, Suwon-si (KR); Jonghyon Yi, Yongin-si (KR); Iljun Ahn, Daejeon (KR); Yongjin Chang, Incheon (KR); Byung-sun Choi, Yongin-si (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 112 days.

This patent is subject to a terminal disclaimer.

(21) Appl. No.: 15/922,144

(22) Filed: Mar. 15, 2018

(65) Prior Publication Data

US 2018/0204330 A1 Jul. 19, 2018

Related U.S. Application Data

(62) Division of application No. 14/554,799, filed on Nov. 26, 2014, now Pat. No. 9,959,631.

(Continued)

(30) Foreign Application Priority Data

Jul. 23, 2014 (KR) .................. 10-2014-0093405
Sep. 1, 2014 (KR) .................. 10-2014-0115697

(51) Int. Cl.
*G06T 7/246* (2017.01)
*A61B 6/03* (2006.01)
(Continued)

(52) U.S. Cl.
CPC .............. *G06T 7/246* (2017.01); *A61B 6/032* (2013.01); *A61B 6/037* (2013.01); *A61B 6/5205* (2013.01);
(Continued)

(58) Field of Classification Search
None
See application file for complete search history.

(56) References Cited

U.S. PATENT DOCUMENTS 5,579,358 A 11/1996 Lin
6,621,889 B1 9/2003 Mostafavi
(Continued)

FOREIGN PATENT DOCUMENTS

CN 102397078 A 4/2012
CN 103413274 A 11/2013
(Continued)

OTHER PUBLICATIONS

Communication dated Mar. 26, 2018 from the Russian Patent Office in counterpart Russian Application No. 2016137475/14.
(Continued)

*Primary Examiner* — Nancy Bitar
(74) *Attorney, Agent, or Firm* — Sughrue Mion, PLLC

(57) ABSTRACT

A tomography apparatus includes a data acquirer configured to acquire partial images of an object including a first image
(Continued)

and a second image having imaged a surface of a portion of the object corresponding to a first time and a second time, respectively, by performing a tomography scan on the object that is moving, and acquire first information indicating motion of the object by using the first image and the second image; and an image reconstructor configured to reconstruct a target image by using the first information.

25 Claims, 47 Drawing Sheets

Related U.S. Application Data

(60) Provisional application No. 61/942,731, filed on Feb. 21, 2014.

(51) Int. Cl.
*G06T 11/00* (2006.01)
*A61B 6/00* (2006.01)

(52) U.S. Cl.
CPC .......... *A61B 6/5264* (2013.01); *G06T 7/248* (2017.01); *G06T 11/006* (2013.01); *G06T 2207/10081* (2013.01); *G06T 2211/412* (2013.01); *G06T 2211/421* (2013.01)

(56) References Cited

U.S. PATENT DOCUMENTS

| | | | |
|---|---|---|---|
| 6,888,915 B2 | 5/2005 | Koenig et al. | |
| 6,934,357 B2 | 8/2005 | Boyd et al. | |
| 7,315,605 B2 | 1/2008 | Boese et al. | |
| 8,055,050 B2 | 11/2011 | Roessl et al. | |
| 8,184,883 B2 | 5/2012 | Grass et al. | |
| 8,224,056 B2 | 7/2012 | Pack et al. | |
| 8,306,303 B2 | 11/2012 | Bruder et al. | |
| 8,437,524 B2 | 5/2013 | Bontus et al. | |
| 8,446,408 B2 | 5/2013 | Grass et al. | |
| 8,553,962 B2 | 10/2013 | Allmendinger et al. | |
| 8,588,493 B2 | 11/2013 | Bruder et al. | |
| 8,611,630 B1 | 12/2013 | Katsevich et al. | |
| 8,731,264 B2 | 5/2014 | Kruecker et al. | |
| 8,731,266 B2 | 5/2014 | Zeng et al. | |
| 8,731,268 B2 | 5/2014 | Li et al. | |
| 9,247,920 B2 * | 2/2016 | Al Assad | A61B 6/5258 |
| 9,336,569 B2 | 5/2016 | Lou et al. | |
| 9,380,985 B2 | 7/2016 | Akahori | |
| 9,576,391 B2 | 2/2017 | Ra et al. | |
| 2002/0025017 A1 | 2/2002 | Stergiopoulos et al. | |
| 2004/0136501 A1 | 7/2004 | Boyd et al. | |
| 2005/0232389 A1 * | 10/2005 | Klingenbeck-Regn | A61B 6/032 378/9 |
| 2007/0092055 A1 | 4/2007 | Vives et al. | |
| 2007/0092066 A1 | 4/2007 | Tkaczyk et al. | |
| 2007/0116175 A1 | 5/2007 | Zhang et al. | |
| 2009/0018435 A1 * | 1/2009 | Hsieh | A61B 5/0402 600/425 |
| 2009/0185656 A1 | 7/2009 | Heuscher | |
| 2009/0242776 A1 | 10/2009 | Kobashi et al. | |
| 2010/0092059 A1 | 4/2010 | Maier | |
| 2010/0316270 A1 | 12/2010 | Erhard et al. | |
| 2011/0092793 A1 | 4/2011 | Thomson et al. | |
| 2011/0142315 A1 | 6/2011 | Hsieh et al. | |
| 2012/0305780 A1 | 12/2012 | Thiruvenkadam et al. | |
| 2013/0114871 A1 | 5/2013 | Berkus et al. | |
| 2013/0177213 A1 | 7/2013 | Lee et al. | |
| 2013/0303898 A1 | 11/2013 | Kinahan et al. | |
| 2014/0355855 A1 | 12/2014 | Miao et al. | |
| 2015/0093001 A1 | 4/2015 | Wang | |

FOREIGN PATENT DOCUMENTS

| | | |
|---|---|---|
| JP | 2009-233025 A | 10/2009 |
| RU | 2479038 C2 | 4/2013 |
| WO | 2013005833 A1 | 1/2013 |

OTHER PUBLICATIONS

Communication dated Jul. 9, 2015, issued by the European Patent Office in counterpart European Patent Application No. 15156187.5.
Communication dated May 28, 2015, issued by the International Searching Authority in counterpart International Patent Application No. PCT/KR2015/001717.
Communication dated Oct. 2, 2017, from the Russian Patent Office in counterpart application No. 2016137475/14.
Dennis L. Parker; "Optimal Short Scan Convolution Reconstruction for Fanbeam CT"; Medical Physics; vol. 9; No. 2; Mar./Apr. 1982; pp. 254-257.
Dirk Schafer et al.; "Motion-Compensated and Gated Cone Beam Filtered Back-Projection for 3-D Rotational X-Ray Angiography"; Medical Imaging, IEEE Transactions on Medical Imaging; vol. 25; No. 7; Jul. 2006; 11 page total.
Communication dated Jun. 9, 2020 from the Intellectual Property Office of the P.R.China in application No. 201580020945.2.

* cited by examiner

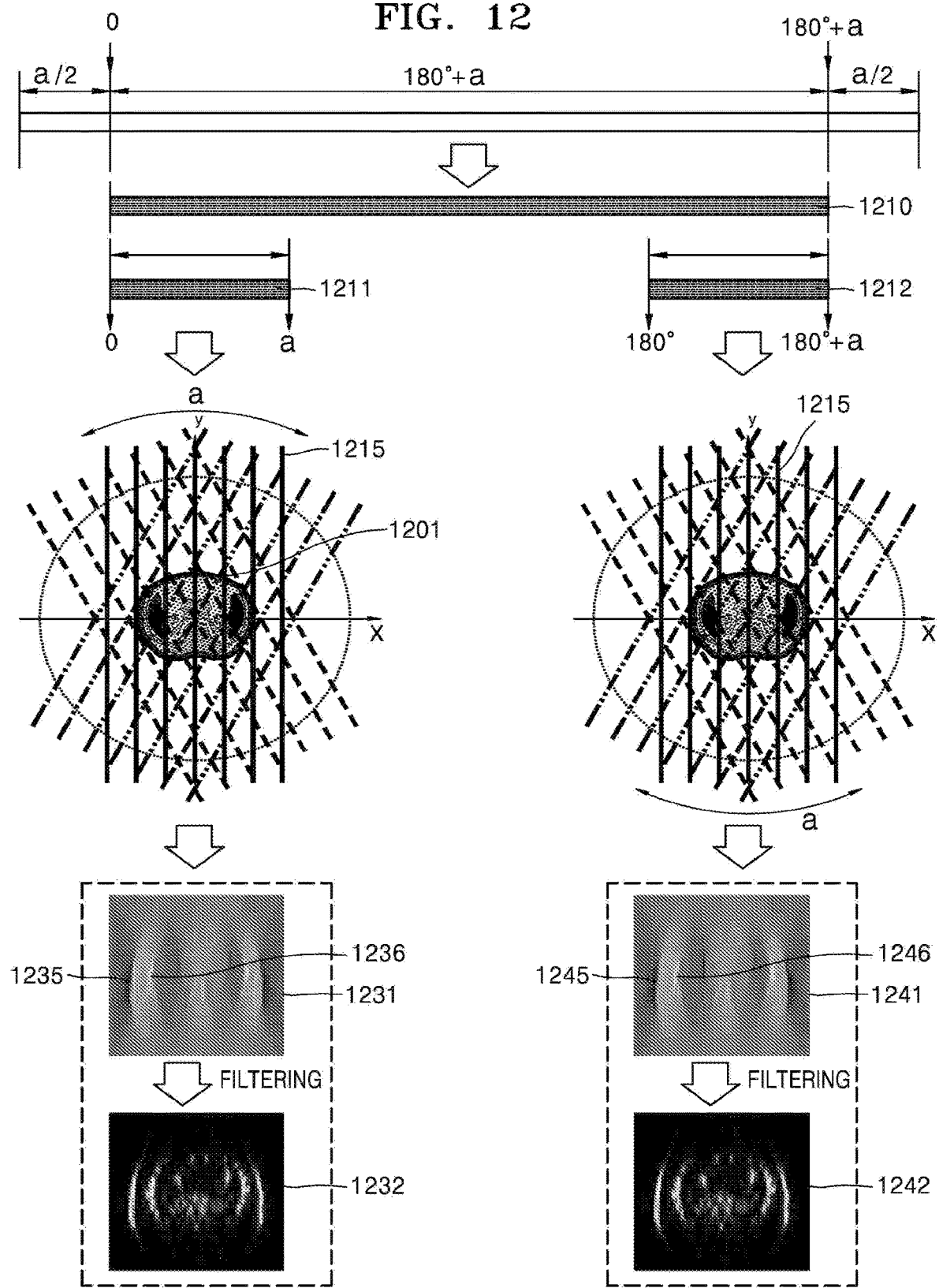

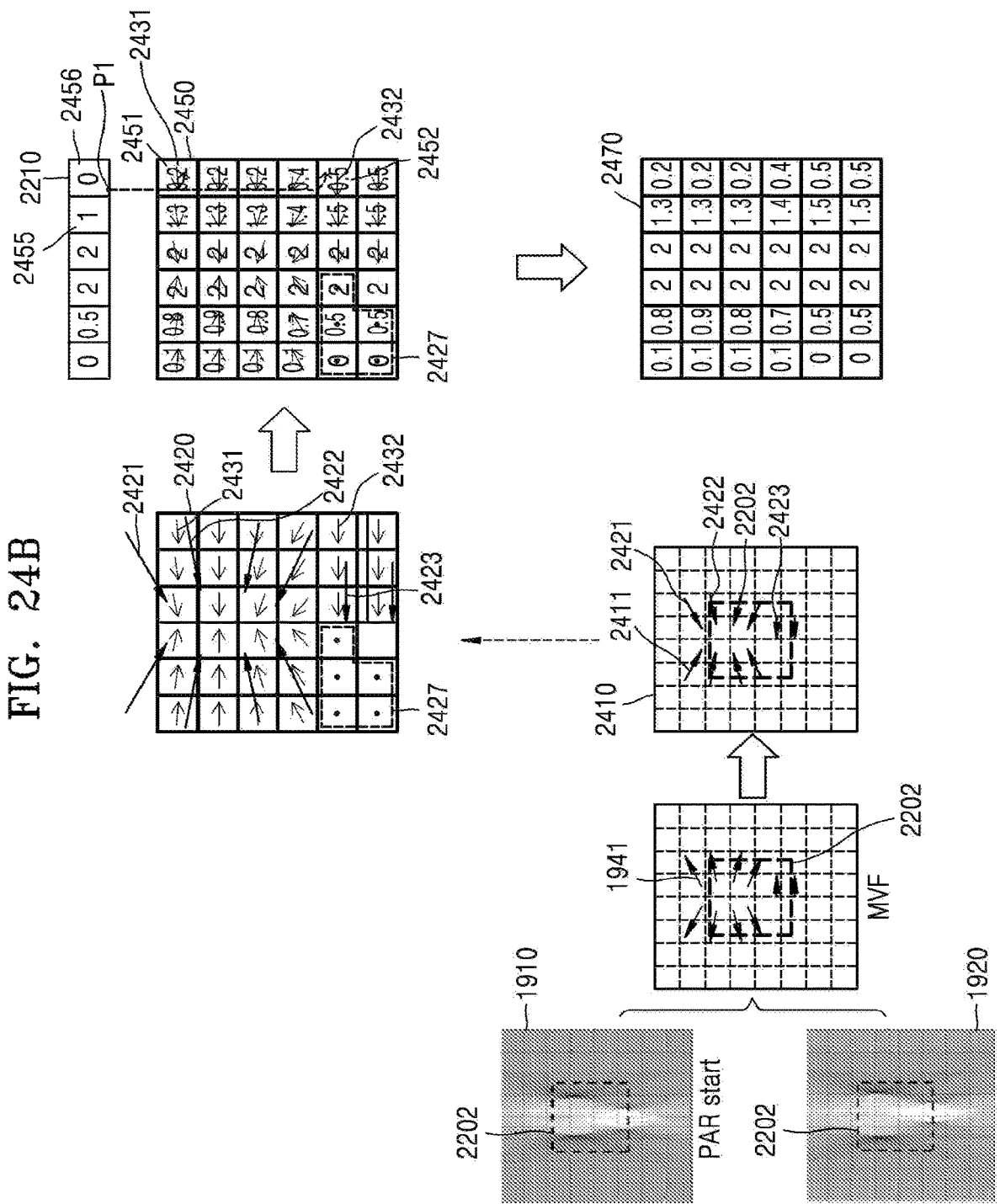

TOMOGRAPHY APPARATUS AND METHOD FOR RECONSTRUCTING TOMOGRAPHY IMAGE THEREOF

CROSS REFERENCE TO RELATED APPLICATIONS

This application is a divisional application of U.S. application Ser. No. 14/554,799, filed Nov. 26, 2014, which claims benefit of the filing date of U.S. Provisional Application No. 61/942,731, filed Feb. 21, 2014, and claims priority from Korean Patent Application No. 10-2014-0093405, filed Jul. 23, 2014 in the Korean Intellectual Property Office, and Korean Patent Application No. 10-2014-0115697, filed Sep. 1, 2014 in the Korean Intellectual Property Office. The disclosures of the above-named applications are incorporated herein in their entireties by reference.

BACKGROUND

1. Field

One or more embodiments of the present invention relate to a tomography apparatus and a method for reconstructing a tomography image thereof.

2. Description of the Related Art

Medical imaging apparatuses are used to acquire an image of an internal structure of an object. Medical image apparatuses that are non-invasive testing apparatuses capture images and provide a processed image to a user including processed structural details, internal tissues, and the flow of fluids in a human body. The user who is, for example, a medical doctor, may diagnose a health state and a disease of a patient by using a medical image output from the medical image processing apparatus.

A tomography apparatus is a typical apparatus among apparatuses for capturing an image of an object by projecting X-rays toward a patient. Herein, tomography apparatus includes a computed tomography (CT) apparatus.

Of the medical image processing apparatuses, the tomography apparatus may provide a cross-sectional image of an object which clearly shows an internal structure, for example, organs such as kidneys, lungs, etc., of the object, without an overlap therebetween, contrary to a general X-ray apparatus. Accordingly, the tomography apparatus is widely used for accurate diagnosis of diseases. In the following description, a medical image acquired by the tomography apparatus is referred to as a tomography image.

In order to acquire a tomography image, a tomography scan is performed on the object by using a tomography apparatus and thus raw data is acquired. The tomography image is reconstructed by using the acquired raw data. The raw data may be projection data, which is obtained by projecting X-rays toward the object, or a sinogram that is a group of pieces of the projection data.

When an object that is a target of a tomography scan moves, motion of the object occurs during one cycle. Due to the motion of the object, motion artifacts may occur in the reconstruction of a tomography image FIG. 2 is a view for describing motion artifacts existing in a reconstructed tomography image 200. FIG. 2 illustrates a tomography image acquired by a full reconstruction method in which an image is reconstructed by using raw data acquired when rotating around an object 210 by 360° or more.

Referring to FIG. 2, when motion artifacts are present in the reconstructed tomography image 200, an outermost edge 220 of the object 210 is unclear due to the motion artifacts. Further, an inner edge 230 of the reconstructed tomography image 200 is blurred due to the motion of the object 210.

The motion artifacts in a tomography image degrade the quality of the tomography image, and thus when a user, for example, a medical doctor, reads the tomography image and diagnoses a disease, the user is unable to accurately read the tomography image and diagnose the disease.

Thus, when a tomography scan is performed on a moving object, it is important to reconstruct a tomography image in which image blurring caused by motion artifacts is reduced.

SUMMARY

One or more embodiments of the present invention include a tomography apparatus which may reduce occurrence of motion artifacts in a reconstructed tomography image, and a method for reconstructing a tomography image thereof.

One or more embodiments of the present invention include a tomography apparatus which may reduce a dose of radiation exposed to a human body and may reconstruct a tomography image in which occurrence of motion artifacts is reduced, and a method for reconstructing a tomography image thereof.

Additional aspects will be set forth in part in the description which follows and, in part, will be apparent from the description, or may be learned by practice of the presented embodiments.

According to one or more embodiments of the present invention, a tomography apparatus includes: a data acquirer acquiring a first image and a second image that are partial images, by using data acquired in a first angular section corresponding to a first time point and a second angular section corresponding to a second time and facing the first angular section, by performing a tomography scan on an object that is moving, and acquiring first information indicating a motion amount of the object by using the first image and the second image; and an image reconstructor reconstructing a target image indicating the object at a target time, based on the first information.

Each of the first angular section and the second angular section may be less than 180°.

The first information may be acquired by comparing only the first image and the second image.

The object being imaged in the first image and the object being imaged in the second image may be different from each other in at least one of a size, a position, and a shape.

In the target image, a degree of motion correction (MC) of the object indicated in the target image may vary according to the target time.

In the target image, motion correction of the object when the target time may correspond to a middle angle between the first angular section and the second angular section may be improved compared to motion correction of the object when the target time does not correspond to the middle angle.

The first information may indicate a motion amount of a surface forming the object.

The first information may indicate a motion amount of a surface forming the object corresponding to time points, as information corresponding to a motion vector field between the first and second image.

The motion vector field may be measured by using non-rigid registration.

In the first information, a value of the time point and a value of the motion amount of the surface indicated as the motion vector field may have a linear relationship.

The data acquirer may acquire the first image and the second image by using raw data acquired by performing the tomography scan in a one-cycle angular section that is less than one turn, and the first angular section and the second angular section may be a start section and an end section of the one-cycle angular section, respectively.

The image reconstructor may reconstruct the target image by using a plurality of pieces of projection data corresponding to a plurality of views that are raw data acquired by performing the tomography scan while rotating less than one turn.

The first information may include information about motions of a surface of the object in all directions, the object being imaged in the first image and the second image.

The image reconstructor may estimate a motion amount of the object at the target time based on the first information and reconstructs the target image based on the estimated motion amount.

The image reconstructor may reconstruct the target image by warping a plurality of partial images representing parts of the object, based on the first information.

The image reconstructor may warp an image grid to image the object based on the first information and reconstructs the target image by using the warped image grid.

In a back-projection process, the image reconstructor may reconstruct the target image by warping a pixel corresponding to the data acquired by the CT scan based on the first information.

The image reconstructor may reconstruct the target image by warping a center of a voxel indicating the object, based on the first information, and performing back-projection with respect to a position of the warped voxel.

The tomography apparatus may further include displaying a user interface receiving information indicating a relationship between time and a motion amount of the object indicated by the first information through the user interface screen for setting the first information, wherein the data acquirer acquires the first information based on the information indicating the relationship.

The data acquirer may perform the tomography scan in an angular section having an angle of 180°+an additional angle in a half reconstruction method using a rebinned parallel beam.

The data acquirer may acquire projection data corresponding to an angular section having an angle of 180°+an additional angle, and the additional angle may be about 30° to 70°.

The tomography apparatus may further include a display displaying a user interface screen that includes a menu for setting the target time.

The tomography apparatus may further include a display displaying a screen that comprises at least one of the first information, a user interface screen for setting the first information, the target time, and the target image.

The data acquirer may divide projection data acquired by performing a tomography scan while rotating around the object, into a plurality of conjugate view sectors, acquire a plurality of partial image pairs including the first image and the second image in each of the plurality of conjugate view sectors, and acquire the first information by using the plurality of partial image pairs corresponding to the plurality of conjugate view sectors.

The tomography apparatus may further include: a display displaying a medical image; and a user interface for setting a region of interest of the medical image, wherein the data acquirer extracts at least one surface included in the region of interest, sets at least one of the first angular section, the second angular section, a start position of a one-cycle angular section, an end position of the one-cycle angular section, and the target time based on a direction of the extracted surface, acquires the first image and the second image in the first angular section and the second angular section, respectively, corresponding to the setting, and acquires the first information indicating a motion amount of the object by using the first image and the second image.

The data acquirer may set at least one of the first angular section, the second angular section, the first time, the second time, a start position of a one-cycle angular section, an end position of the one-cycle angular section, and the target time, considering a direction in which the object moves.

The object may be at least one of a heart, abdomen, womb, brain, breast, and liver.

The object may be a heart that is expressed by a surface, and the heart may include at least one of tissues having different brightness values in a predetermined area.

The data acquirer may perform a tomography scan according to at least one of an axial scanning method and a helical scanning method.

The data acquirer may acquire additional information that is information about motion generated in at least one of the object and the outside of the object during a tomography scan, and acquire first information indicating a motion amount of the object based on the first image, the second image, and the additional information.

The data acquirer may acquire a plurality of partial image pairs including the first image and the second image that image the same portion of the object, by using a helical scanning method, and acquire the first information by using the plurality of partial image pairs.

According to one or more embodiments of the present invention, a tomography apparatus includes: a data acquirer acquiring a first image indicating a first image indicating a surface of a portion of an object and a second image indicating the surface of the portion of the object that are partial images corresponding to a first time and a second time, by performing a tomography scan on the object that is moving, and acquiring first information indicating motion of the object by using the first image and the second image; and an image reconstructor reconstructing a target image by using the first information.

The first image and the second image may be partial images that are reconstructed by using data acquired in a first angular section and a second angular section have values less than 180°.

The first information may be acquired by comparing only the first image and the second image.

The object being imaged in the first image and the object being imaged in the second image may be different from each other in at least one of a size, a position, and a shape.

The first information may be information indicating a motion amount of a surface forming the object corresponding to time point, as information corresponding to a motion vector field between the first image and the second image.

The data acquirer may perform the tomography scan in a one-cycle angular section that is less than one turn, and the first time may correspond to a start section of the one-cycle angular section and the second time corresponds to an end section of the one-cycle angular section.

The image reconstructor may reconstruct a target image indicating the object at a target time between the first time and the second time, based on the first information.

In the target image, a degree of motion correction of the object included in the target image may vary according to the target time.

In the target image, motion correction of the object when the target time may correspond to a middle angle between the first angular section and the second angular section may be improved, compared to motion correction of the object when the target time does not correspond to the middle angle.

The image reconstructor may reconstruct the target image by using a plurality of pieces of projection data corresponding to a plurality of views that are raw data acquired by performing the tomography scan while rotating less than one turn.

The first information may be information indicating a motion amount of a surface of the object during a period between the first time and the second time.

According to one or more embodiments of the present invention, a method for reconstructing a tomography image includes: acquiring a first image and a second image that are partial images, by using data acquired in a first angular section corresponding to a first time and a second angular section corresponding to a second time and facing the first angular section, by performing a tomography scan on an object that is moving; acquiring first information indicating a motion amount of the object at a time point, by using the first image and the second image; and reconstructing a target image indicating the object at a target time, based on the first information.

Each of the first angular section and the second angular section may be less than 180°.

The acquiring of the first information may include acquiring the first information by comparing only the first image and the second image.

The object being imaged in the first image and the object being imaged in the second image may be different from each other in at least one of a size, a position, and a shape.

In the target image, a degree of motion correction of the object indicated in the target image may vary according to the target time.

In the target image, motion correction of the object when the target time may correspond to a middle angle between the first angular section and the second angular section is improved, compared to motion correction of the object when the target time does not correspond to the middle angle.

The first information may indicate a motion amount of a surface forming the object.

The first information may indicate a motion amount of a surface forming the object corresponding to time point, as information corresponding to a motion vector field between the first and second image.

The motion vector field may be measured by using non-rigid registration.

In the first information, a value of the time point and a value of the motion amount of the surface indicated as the motion vector field may have a linear relationship.

The acquiring of the first image and the second image may include acquiring the first image and the second image by using raw data acquired by performing a tomography scan in a one-cycle angular section that is less than one turn, and the first angular section and the second angular section may be a start section and an end section of the one-cycle angular section, respectively.

The reconstructing of the target image may include reconstructing the target image by using a plurality of pieces of projection data corresponding to a plurality of views that are raw data acquired by performing a tomography scan while rotating less than one turn.

The first information may include information about a motion of a surface of the object in all directions, the object being imaged in the first image and the second image.

The reconstructing of the target image may include estimating a motion amount of the object at the target time based on the first information and reconstructing the target image based on the estimated motion amount.

The reconstructing of the target image may include reconstructing the target image by warping a plurality of partial images indicating parts of the object, based on the first information.

The reconstructing of the target image may include; warping a center of a voxel indicating the object, based on the first information; and reconstructing the target image by performing back-projection with respect to a position of the warped voxel.

The method may further include receiving information indicating a relationship between time and a motion amount of the object indicated by the first information through the user interface screen for setting the first information, wherein, in the acquiring of the first information, the first information is acquired based on the information indicating the relationship.

The acquiring of the first image and the second image may include performing the tomography scan in an angular section having an angle of 180°+an additional angle in a half reconstruction method using a rebinned parallel beam.

The method may further include acquiring projection data corresponding to angle of 180°+an additional angle, wherein the additional angle has a value of about 30° to 70°.

The method may further include displaying a user interface screen that may include a menu for setting the target time.

The method may further include displaying a screen that may include at least one of the first information, a user interface screen for setting the first information, the target time, and the target image.

The acquiring of the first image and the second image may include: dividing projection data acquired by performing a tomography scan while rotating around the object, into a plurality of conjugate view sectors; and acquiring a plurality of partial image pairs including the first image and the second image in each of the plurality of conjugate view sectors, and the acquiring of the first information may include acquiring the first information by using the plurality of partial image pairs corresponding to the plurality of conjugate view sectors.

The method may further include: displaying a medical image; and setting a region of interest of the medical image, wherein the acquiring of the first image and the second image may include extracting at least one surface included in the region of interest, setting at least one of the first angular section, the second angular section, a start position of a one-cycle angular section, an end position of the one-cycle angular section, and the target time based on a direction of the extracted surface, acquiring the first image and the second image in the first angular section and the second angular section, respectively, corresponding to the setting, and acquiring the first information indicating a motion amount of the object by using the first image and the second image.

The method may further include setting at least one of the first angular section, the second angular section, the first time, the second time, a start position of a one-cycle angular section, an end position of the one-cycle angular section, and the target time, considering a direction in which the object moves.

The object may include at least one of a heart, abdomen, womb, brain, breast, and liver.

The object may include a heart that is expressed by a surface, and the heart may include at least one of tissues having different brightness values in a predetermined area.

The method may further include performing a tomography scan according to at least one of an axial scanning method and a helical scanning method.

The method may further include acquiring additional information that is information about motion generated in at least one of the object and the outside of the object during a tomography scan, wherein the acquiring of the first information may include acquiring first information indicating a motion amount of the object based on the first image, the second image, and the additional information.

The acquiring of the first image and the second image may include acquiring a plurality of partial image pairs including the first image and the second image that image the same portion of the object, by using a helical scanning method, and the acquiring of the first information may include acquiring the first information by using the plurality of partial image pairs.

According to one or more embodiments of the present invention, a method for reconstructing a tomography image includes: acquiring a first image and a second image that indicate same portions of a surface forming an object and are partial images corresponding to a first time and a second time, by performing a tomography scan on the object that is moving; acquiring first information indicating motion of the object by using the first image and the second image; and reconstructing a target image by using the first information.

The first image and the second image may be partial images that are reconstructed by using data acquired in a first angular section and a second angular section that are less than 180°.

In the acquiring of the first information, the first information may be acquired by comparing only the first image and the second image The object being imaged in the first image and the object being imaged in the second image may be different from each other in at least one of a size, a position, and a shape.

The first information may be information indicating a motion amount of a surface forming the object corresponding to time point, as information corresponding to a motion vector field between the first image and the second image.

The acquiring of the first image and the second image may include performing the tomography scan in a one-cycle angular section that is less than one turn, and the first time may correspond to a start section of the one-cycle angular section and the second time may correspond to an end section of the one-cycle angular section.

The reconstructing of the target image may include reconstructing a target image indicating the object at a target time between the first time and the second time, based on the first information.

In the target image, a degree of motion correction of the object included in the target image may vary according to the target time.

In the target image, motion correction of the object when the target time corresponds to a middle angle between the first angular section and the second angular section may be improved, compared to motion correction of the object when the target time does not correspond to the middle angle.

The reconstructing of the target image may include reconstructing the target image by using a plurality of pieces of projection data corresponding to a plurality of views that are raw data acquired by performing the tomography scan while rotating less than one turn.

The first information may be information indicating a motion amount of a surface of the object during a period between the first time and the second time.

According to one or more embodiments of the present invention, a tomography apparatus includes: a data acquirer acquiring a first partial image and a second partial image that are partial images, by using data acquired in each of a start angular section and an end angular section facing the start angular section, by performing a tomography scan on an object that is moving, and acquiring first information indicating a relationship between time and a motion amount of a surface of the object corresponding to a motion vector field between the first partial image and the second partial image; and an image reconstructor reconstructing a target image indicating the object at a target time, based on the first information.

According to one or more embodiments of the present invention, a tomography apparatus includes: a data acquirer acquiring a first image and a second image that are partial images respectively corresponding to a first time and a second time and indicating same portions of surfaces forming an object, by performing a tomography scan on the object that is moving, and acquiring first information indicating motion of the object by using the first image and the second image; and an image reconstructor reconstructing a target image indicating the object at a target time by warping at least one of raw data needed for half reconstruction and an image acquired by performing filtered back-projection on the raw data, based on the first information.

According to one or more embodiments of the present invention, a tomography apparatus include: a data acquirer acquiring a first image and a second image that are partial images, by using data acquired in a first angular section corresponding to a first time point and a second angular section corresponding to a second time and facing the first angular section, by performing a tomography scan on an object, and acquiring first information indicating a motion amount of the object by using the first image and the second image; and an image reconstructor reconstructing a target image indicating the object at a target time, based on the first information.

According to one or more embodiments of the present invention, a medical imaging apparatus include: a data acquirer acquiring a first image and a second image that are partial images, by using data acquired in a first angular section corresponding to a first time point and a second angular section corresponding to a second time and facing the first angular section, by performing a tomography scan on an object that is moving, and acquiring first information indicating a motion amount of the object by using the first image and the second image; and an image reconstructor reconstructing a target image indicating the object at a target time, based on the first information.

BRIEF DESCRIPTION OF THE DRAWINGS

These and/or other aspects will become apparent and more readily appreciated from the following description of the embodiments, taken in conjunction with the accompanying drawings in which:

FIG. 12 is a view for describing the operation of a tomography apparatus according to an embodiment of the present invention;

FIGS. 24A and 24B are views for describing an operation of reconstructing a target image;

DETAILED DESCRIPTION

Figure 1A:
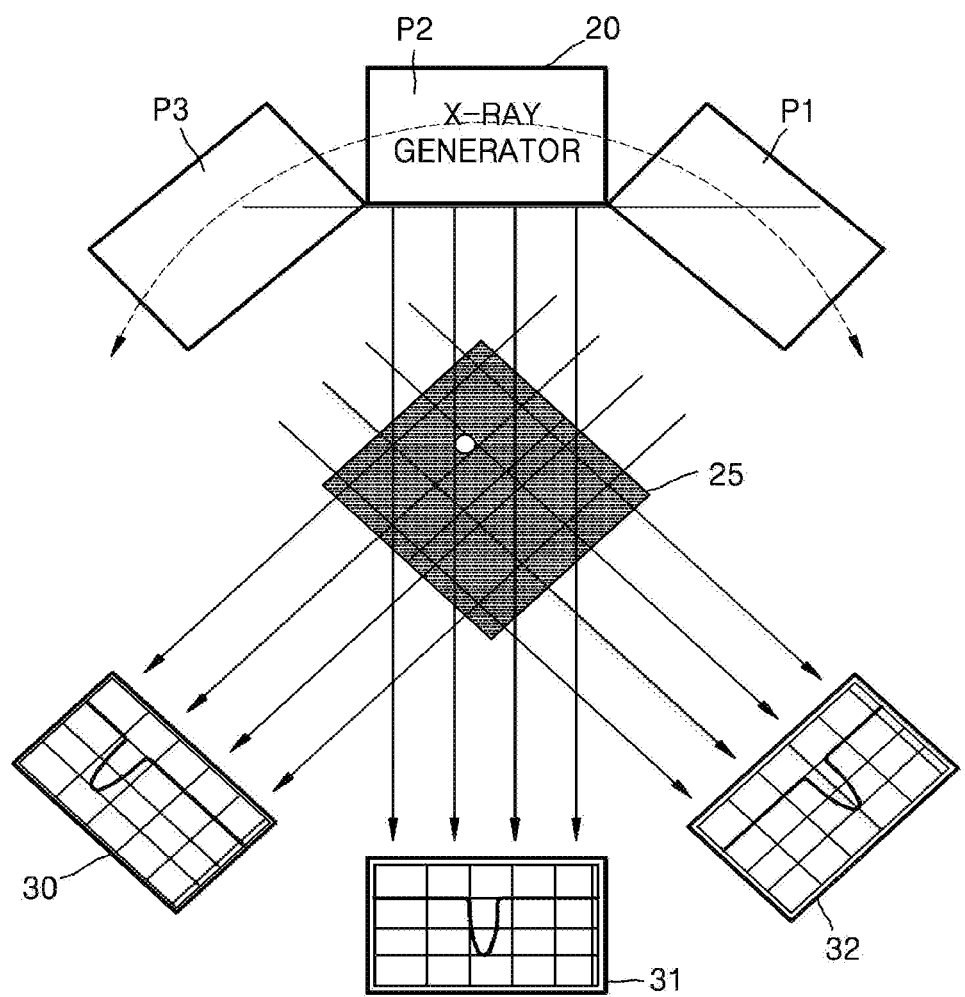
FIGS. 1A and 1B are views for describing tomography imaging and reconstruction operations.

Advantages and features of one or more embodiments of the present invention and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present invention will only be defined by the appended claims Like reference numerals refer to like elements throughout the specification.

Hereinafter, the terms used in the specification will now be briefly defined, and the embodiments will now be described in detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present invention means a software component or hardware components such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail since they would obscure the embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a tomography imaging apparatus.

Throughout the specification, a "tomography image" may mean an image obtained by performing a tomography scan on an object by using a tomography imaging apparatus, that is, an image obtained by projecting a light beam such as an X-ray toward an object and imaging by using projection data. Throughout the specification, a "tomography image" may mean an image generated by synthesizing a plurality of X-ray images that are obtained by capturing an image of an object while a tomography imaging apparatus rotates around at least one axis with respect to the object.

Throughout the specification, examples of an "object" may include a human, an animal, or a part of a human or animal. For example, examples of the object may include at least one of organs such as liver, heart, womb, brain, breast, abdomen, etc., and blood vessels. Also, the object may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a doctor, a nurse, a medical laboratory technologist, a medial image expert, and a technician who repairs a medical apparatus.

Since a tomography system, such as CT system, is capable of providing a cross-sectional image of an object, the tomography system may express an inner structure (e.g., organs such as kidneys, lungs, etc.) of the object without an overlap therebetween, contrary to a general X-ray imaging apparatus.

In detail, a tomography system may include all tomography apparatuses such as a computed tomography (CT) apparatus, an optical coherence tomography (OCT), or a positron emission tomography (PET)-CT apparatus. In the following description, a CT system is exemplified as the tomography system.

The tomography system may obtain a plurality of pieces of image data with a thickness not more than 2 mm, several tens to several hundreds of times per second, and then may process the plurality of pieces of image data, so that the tomography system may provide a relatively accurate a cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method that displays only voxels having a predetermined Hounsfield Units (HU) value.

Maximum intensity projection (MIP)/minimum intensity projection (MinIP)—a 3D imaging method that displays only voxels having the greatest or smallest HU value from among voxels that construct an image.

Volume rendering (VR)—an imaging method capable of adjusting a color and transmittance of voxels that construct an image, according to regions of interest.

Virtual endoscopy—a method that allows an endoscopy observation in a 3D image that is reconstructed by using the VR method or the SSD method.

Multi-planar reformation (MPR)—a method used to reconstruct an image into a different cross-sectional image. A user may reconstruct an image in every desired direction.

Editing—a method that involves editing adjacent voxels so as to allow a user to easily observe a region of interest in volume rendering.

Voxel of interest (VOI)—a method that displays only a selected area in volume rendering.

For example, in order to acquire a tomography image, an operation of image reconstruction is performed by using the sinogram acquired through the tomography scan. The tomography image reconstruction operation is described below in detail with reference to FIGS. 1A and 1B.

Figure 1B:
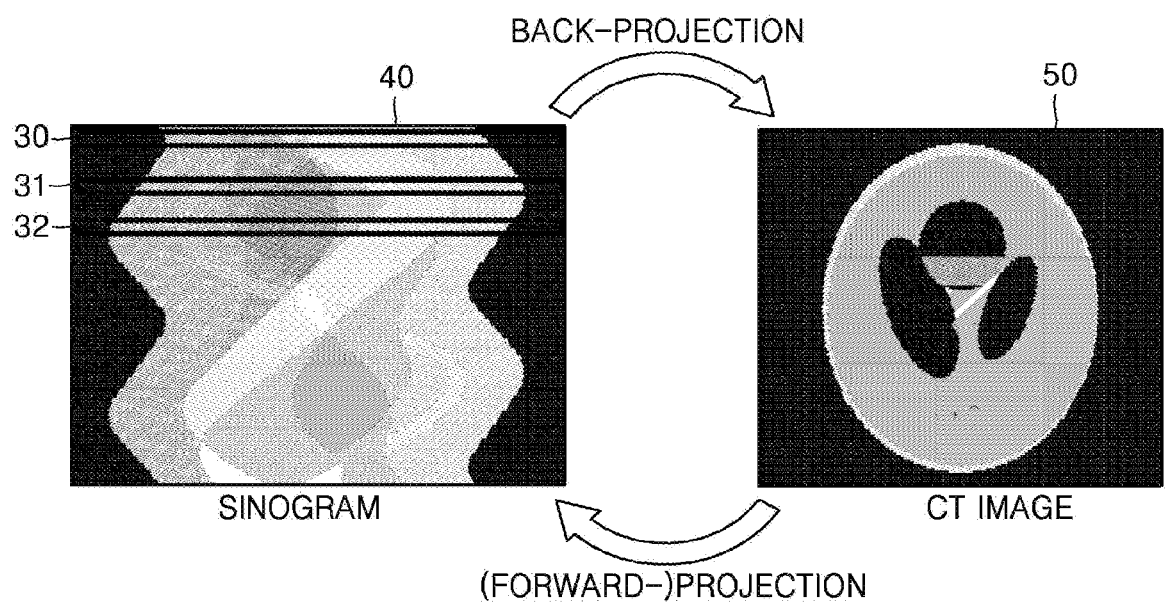

FIGS. 1A and 1B are views for describing tomography imaging and reconstruction operations.

In detail, FIG. 1A is a diagram for describing a tomography imaging operation of a tomography apparatus that performs a tomography scan while rotating around an object 25 and acquires raw data corresponding thereto. FIG. 1B is a sinogram acquired by a tomography scan and a reconstructed tomography image.

The tomography apparatus generates and projects X-rays toward the object 25, and the X-rays passing through the object 25 are detected by an X-ray detector (not shown). The X-ray detector generates raw data corresponding to the detected X-ray.

In detail, referring to FIG. 1A, an X-ray generator 20 included in the tomography apparatus projects X-rays toward the object 25. In the tomography scan which is performed by the tomography apparatus, the X-ray generator 20 rotates around the object 25 and acquires a plurality of pieces of first, second, and third raw data 30, 31, and 32 according to a rotating angle. In detail, the X-ray generator 20 acquires the first, second, and third raw data 30, 31, and 32 by detecting the X-ray beam applied to the object 25 at positions P1, P2, and P3, respectively. The raw data may be projection data.

In order to generate one cross-sectional tomography image, the X-ray generator 20 performs a tomography scan while rotating at least 180°.

Referring to FIG. 1B, as described in FIG. 1A, a sinogram 40 may be obtained by combining the first, second, and third projection data 30, 31, and 32 which are acquired by moving the X-ray generator 20 at a predetermined angular interval. The sinogram 40 is acquired through a tomography scan performed while the X-ray generator 20 rotates during one cycle. The sinogram 40 corresponding to one cyclic rotation may be used for generation of one cross-sectional tomography image. One cyclic rotation may be about more than a half turn or one turn according to the specifications of the tomography system.

A tomography image 50 is reconstructed by performing filtered back-projection on the sinogram 40.

In general, it takes about 0.2 seconds for the X-ray generator 20 to rotate a half turn.

A tomography system 100 according to an embodiment of the present invention will now be described with reference to FIG. 3. The tomography system 100 may include various types of devices.

Figure 3:
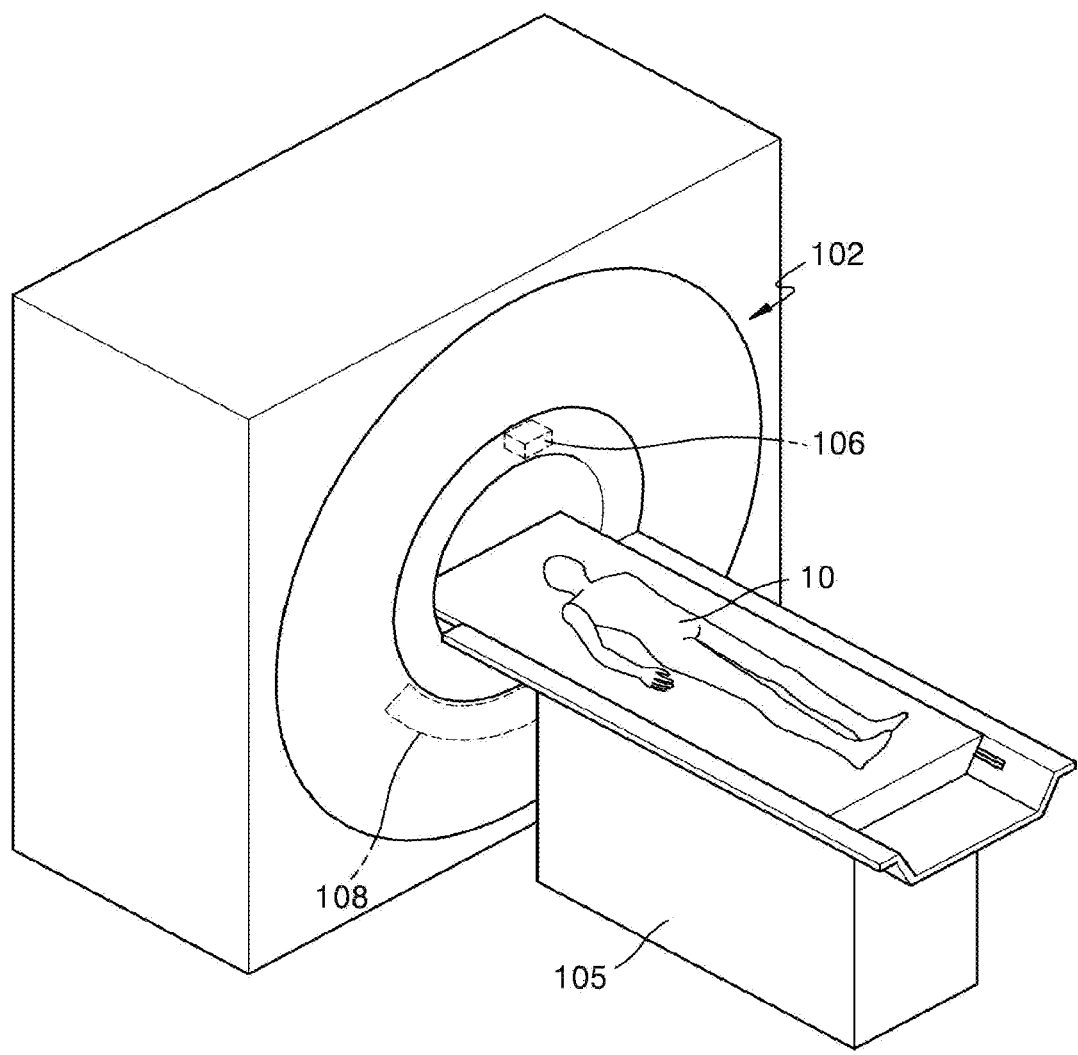
FIG. 3 is a schematic view of a tomography system.

FIG. 3 schematically illustrates the tomography system 100. Referring to FIG. 3, the tomography system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction, for example, at least one of up, down, right, and left directions, during a tomography imaging procedure. Also, the table 105 may tilt or rotate by a predetermined degree in a predetermined direction.

The gantry 102 may also tilt by a predetermined degree in a predetermined direction.

Figure 4:
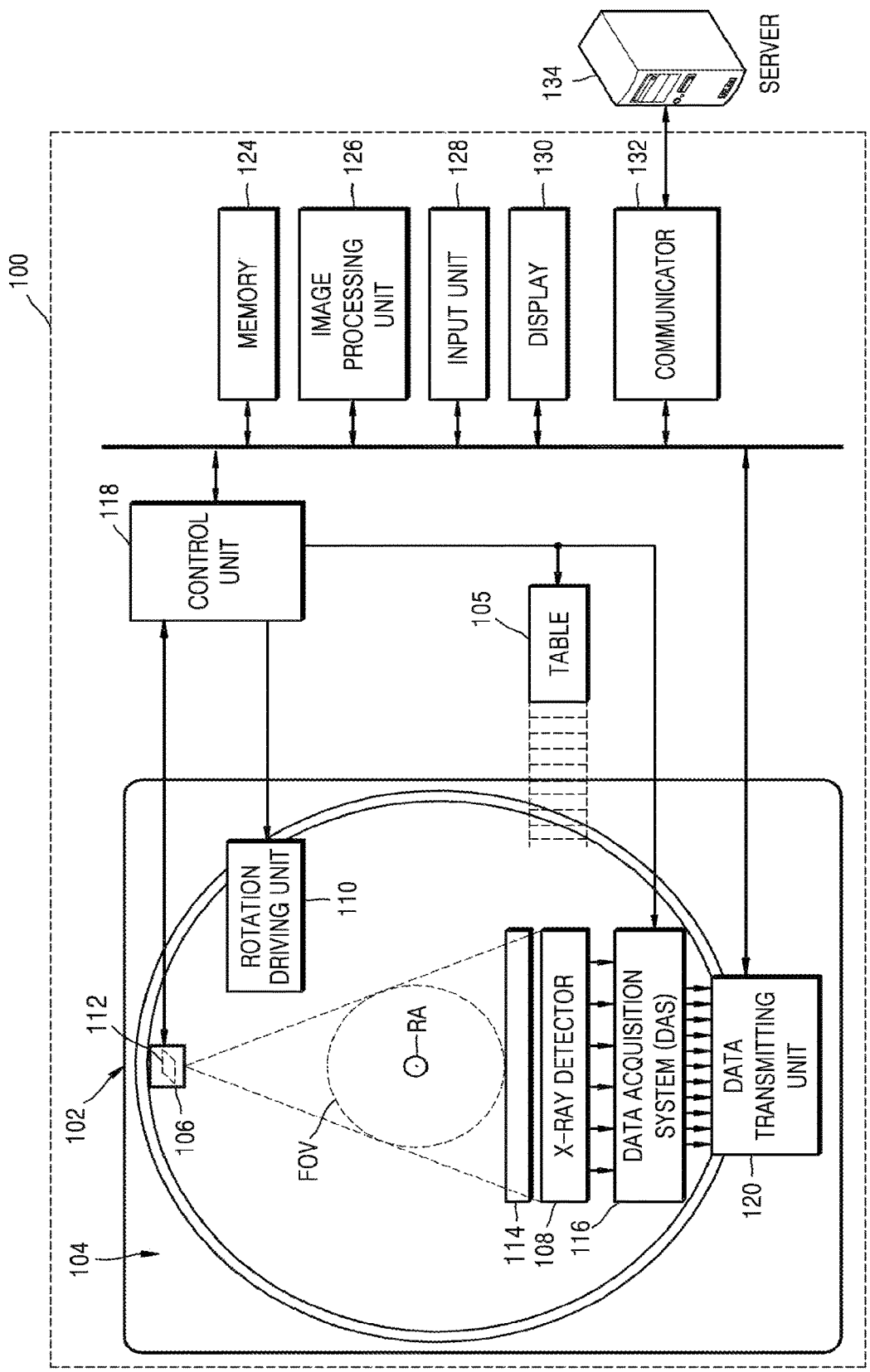
FIG. 4 is a block diagram illustrating a structure of a tomography system according to an embodiment of the present invention.

FIG. 4 is a diagram illustrating a structure of the tomography system 100 according to an embodiment of the present invention.

The tomography system 100 may include the gantry 102, the table 105, a control unit 118, a memory 124, an image processing unit 126, an input unit 128, a display 130, and a communicator 132.

As described above, the object 10 may be positioned on the table 105. In the present embodiment, the table 105 may move in a predetermined direction, for example, at least one of up, down, right, and left directions, and motion of the table 105 may be controlled by the control unit 118.

The gantry 102 may include a rotating frame 104, the X-ray generator 106, the X-ray detector 108, a rotation driving unit 110, a data acquisition system (DAS) 116, and a data transmitting unit 120.

The gantry 102 may include the rotating frame 104 having a loop shape capable of rotating with respect to a predetermined rotation axis RA. Also, the rotating frame 104 may have a disc shape.

The rotating frame 104 may include the X-ray generator 106 and the X-ray detector 108 that are arranged to face each other so as to have predetermined field of views (FOV). The rotating frame 104 may also include an anti-scatter grid 114. The anti-scatter grid 114 may be positioned between the X-ray generator 106 and the X-ray detector 108.

Although FIG. 4 illustrates that the rotating frame 104 includes one X-ray generator 106, the rotating frame 104 may include a plurality of X-ray generators. Also, when the rotating frame 104 includes a plurality of X-ray generators, the rotating frame 104 includes a plurality of X-ray detectors corresponding to the plurality of X-ray generators. In detail, one X-ray generator 106 is one X-ray source. For example, when the rotating frame 104 includes two X-ray generators 106, it may be said that the rotating frame 104 includes a dual source. In the following description, when the rotating frame 104 includes one X-ray generator 106, the one X-ray generator 106 included in the rotating frame 104 is referred to as a single source. Also, when the rotating frame 104 includes two X-ray generators (not shown), the two X-ray generators included in the rotating frame 104 is referred to as a dual source. In the two X-ray generators forming a dual source, one X-ray generator is referred to as a first source and the other X-ray generator is referred to as a second source. Also, the tomography system 100 in which the X-ray generator 106 is included in the rotating frame 104 is referred to as a single source tomography apparatus and, when two X-ray generators are included in the rotating frame 104 may be referred to as a dual source tomography apparatus.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generator 106 and the X-ray detector 108 at a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via wireless communication.

The X-ray generator 106 may receive a voltage and current from a power distribution unit (PDU) (not shown) via a slip ring (not shown) and a high voltage generating unit (not shown), and then may generate and project X-rays. When the high voltage generating unit applies predetermined voltage (hereinafter, referred to as the tube voltage) to the X-ray generator 106, the X-ray generator 106 may generate X-rays having a plurality of energy spectra that correspond to the tube voltage.

The X-ray generated by the X-ray generator 106 may be emitted in a predetermined form due to a collimator 112.

The X-ray detector 108 may be positioned to face the X-ray generator 106. The X-ray detector 108 may include a plurality of X-ray detecting devices. Each of the plurality of X-ray detecting devices may establish one channel but one or more embodiments of the present invention are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. The electrical signal generated by the X-ray detector 108 may be wired or wirelessly collected by the DAS 116. Also, the electrical signal generated by the X-ray detector 108 may be provided to an analog-to-digital converter (not shown) via an amplifier (not shown).

According to a slice thickness or the number of slices, only part of data collected by the X-ray detector 108 may be provided to the image processing unit 126 via the data transmitting unit 120, or the image processing unit 126 may select only part of data.

The digital signal may be provided to the image processing unit 126 via the data transmitting unit 120. The digital signal may be wired or wirelessly provided to the image processing unit 126.

The control unit 118 may control an operation of each of modules in the tomography system 100. For example, the control unit 118 may control operations of the table 105, the rotation driving unit 110, the collimator 112, the DAS 116, the memory 124, the image processing unit 126, the input unit 128, the display 130, the communicator 132, etc.

The image processing unit 126 may receive data, for example, pure data before processing, which is obtained from the DAS 116, via the data transmitting unit 120, and may perform pre-processing.

The pre-processing may include a process of correcting sensitivity irregularity between channels and a process of correcting a signal loss due to a rapid decrease of a signal strength or due to an X-ray absorbing material such as metal, etc.

Data output from the image processing unit 126 may be referred to as raw data or projection data. The projection data may be stored in the memory 124 with imaging conditions, for example, the tube voltage, an imaging angle, etc., during the acquisition of data.

The projection data may be a group of data values that correspond to the intensity of the X-ray that passes through the object 10. For convenience of description, it is assumed that a group of a plurality of pieces of projection data that are simultaneously obtained from all channels at the same imaging degree is referred to as a projection data set.

The memory 124 may include at least one storage medium from among a flash memory-type storage medium, a hard disk-type storage medium, a multimedia card micro-type storage medium, card-type memories such as an SD card, an XD memory, etc., random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may reconstruct a cross-sectional image with respect to the object 10 by using the acquired projection data set. The cross-sectional image may be a 3D image. In other words, the image processing unit 126 may reconstruct a 3D image of the object 10 by using a cone beam reconstruction method etc., based on the acquired projection data set.

The input unit 128 may receive an external input with respect to an X-ray tomography imaging condition, an image processing condition, etc. For example, the X-ray tomography imaging condition may include tube voltages, energy value setting with respect to a plurality of X-ray beams, selection of an imaging protocol, selection of an image reconstruction method, setting of a FOV area, the number of slices, a slice thickness, parameter setting with respect to image post-processing, etc. Also, the image processing condition may include a resolution of an image, attenuation coefficient setting with respect to the image, setting of an image combining ratio, etc.

The input unit 128 may include a device for receiving a predetermined input from an external source. For example, the input unit 128 may include a microphone, a keyboard, a mouse, a joystick, a touchpad, a touch pen, a voice recognition device, a gesture recognition device, etc.

The display 130 may display an X-ray image reconstructed by the image processing unit 126.

Exchanges of data, power, etc. between the aforementioned elements may be performed by using at least one of wired communication, wireless communication, and optical communication.

The communicator 132 may perform communication with an external device, an external medical apparatus, etc. via a server 134, etc. The communication will now be described with reference to FIG. 4.

Figure 5:
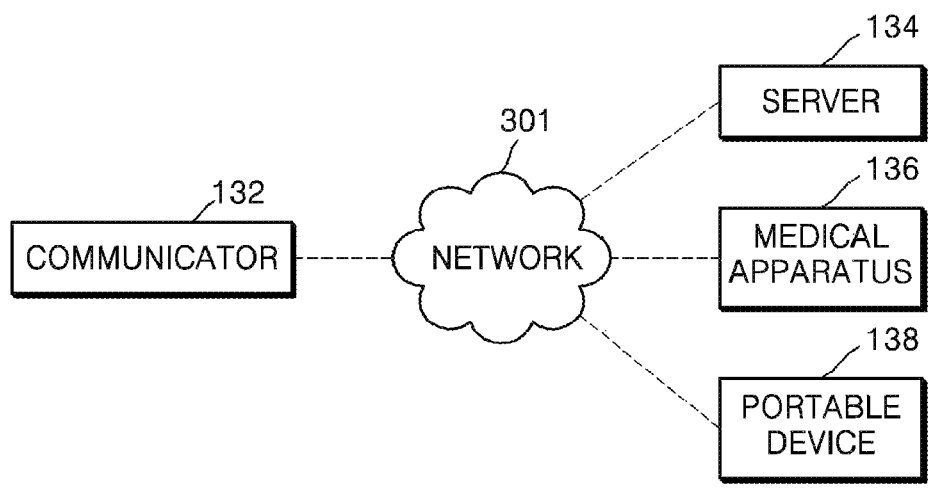
FIG. 5 is a block diagram illustrating a structure of a communicator.

FIG. 5 is a diagram illustrating a structure of the communicator 132.

The communicator 132 may be wired or wirelessly connected to a network 301 and therefore may perform communication with the server 134, an external medical apparatus 136, or an external portable device 138. The communicator 132 may exchange data with a hospital server or other medical apparatuses in a hospital connected via a picture archiving and communication system (PACS).

Also, the communicator 132 may perform data communication with an external device, etc., according to a digital imaging and communications in medicine (DICOM) standard.

The communicator 132 may transmit and receive data related to diagnosing the object 10, via the network 301. Also, the communicator 132 may transmit and receive a medical image obtained from the medical apparatus 136 such as a magnetic resonance imaging (MRI) apparatus, an X-ray apparatus, etc.

Furthermore, the communicator 132 may receive a diagnosis history or a medical treatment schedule about a patient from the server 134 and may use the diagnosis history or the medical treatment schedule in a clinical diagnosis for the patient. Also, the communicator 132 may perform data communication not only with the server 134 or the medical apparatus 136 in a hospital but also with the portable device 138 of a user or patient.

Also, the communicator 132 may transmit information about a device error, information about a quality control status, etc. to a system manager or a service manager via the network 301, and may receive a feedback corresponding to the information.

Figure 6:
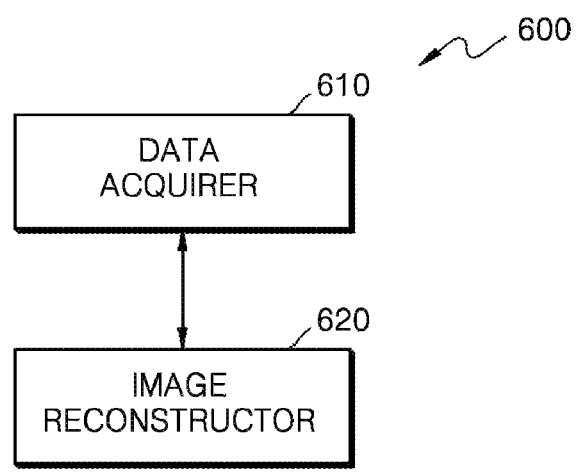
FIG. 6 is a block diagram illustrating a tomography apparatus according to an embodiment of the present invention.

FIG. 6 is a block diagram illustrating a tomography apparatus 600 according to an embodiment of the present invention.

Referring to FIG. 6, the tomography apparatus 600 according to the present embodiment includes a data acquirer 610 and an image reconstructor 620.

The tomography apparatus 600 may be included in the tomography system 100 that is described with reference to FIGS. 3 and 4. Also, the tomography apparatus 600 may be included in the medical apparatus 136 or the portable device 138 and may operate by being connected to the tomography system 100.

In detail, the tomography apparatus 600 may be all medical imaging apparatuses that reconstruct images by using data obtained by using a light beam passing through an object. In other words, the tomography apparatus 600 may be all medical imaging apparatuses that reconstruct images by using projection data obtained by using a light beam passing through an object. In detail, the tomography apparatus 600 may be a computed Tomography (CT) apparatus, an optical coherence tomography (OCT), or a positron emission tomography (PET)-CT apparatus. Accordingly, the tomography image obtained by the tomography apparatus 600 according to the present embodiment may be a CT image, an OCT image, or a PET image. In the drawings referred to the following descriptions, a CT image is exemplified as the tomography image. Also, the tomography apparatus 500 may be an MRI apparatus.

Also, when the tomography apparatus 600 is included in the tomography system 100 described with reference to FIG. 1, the data acquirer 610 and the image reconstructor 620 illustrated in FIG. 6 may be included in the image processing unit 126 of FIG. 4.

The data acquirer 610 acquires first information indicating motion of the object according to the lapse of time, by performing a tomography scan on an object 10. The object may be a predetermined organ. In detail, examples of the object may include at least one of a heart, abdomen, womb, brain, breast, and liver. For example, the object may be a heart that is expressed by a surface thereof. A heart may include at least one of tissues having different brightness values in a predetermined area.

Also, the data acquirer 610 may acquire raw data by performing a tomography scan while rotating around the object less than one turn. The raw data may be projection data acquired by projecting radiation, such as X-rays, toward the object, or a sinogram that is a group of the projection data. Also, raw data may be an image that is generated by performing filtered back-projection on the projection data or the sinogram. In detail, when the X-ray generator 106 at a predetermined position projects X-rays toward the object, a viewpoint or a direction in which the X-ray generator 106 faces the object is referred to as a view. The projection data denotes raw data acquired corresponding to a view and the sinogram denotes raw data acquired by sequentially listing a plurality of pieces of projection data.

In detail, when the X-ray generator 106 emits a cone beam while rotating around the object that is moving, the data acquirer 610 may acquire raw data corresponding to the cone beam and may convert the acquired raw data to raw data corresponding to a parallel beam by rearranging the acquired raw data. First information may be acquired by using the raw data corresponding to a parallel beam. In doing so, the cone beam is converted into the parallel beam, which is referred to as rebinning, and the first information may be acquired by using the raw data corresponding to the parallel beam. The rebinning of the cone beam is described below in detail with reference to FIG. 10.

In detail, the data acquirer 610 acquires data in a first angular section corresponding to a first time and a second angular section corresponding to a second time and facing the first angular section, by performing a tomography scan on the object that is moving, and acquires a first image and a second image by using the data acquired in each of the first and second angular sections.

The image reconstructor 620 reconstructs a target image representing the object at a target time, based on the first information.

The first information denotes a motion amount of the object according to the lapse of time. In detail, the first information may denote motion of a surface forming the object at a time point. The first information is described below in detail with reference to FIG. 13.

In detail, the data acquirer 610 acquires the first image by using raw data acquired during the first angular section corresponding to the first time, and the second image by using raw data acquired during the second angular section that corresponds to the second time and has a conjugate-angle relationship with the first angular section (i.e., the angle of the second angular section and the angle of the first angular section are conjugate angles). In this description, the term "the first angular section" or "the second angular section" denotes a partial angular section included in a one-cycle angular section that is less than one turn. In detail, the first and second angular sections each may have a value less than 180°. Also, the first and second images are partial images. The data acquirer 610 acquires information indicating motion of the object by using the first and second images. In detail, the data acquirer 610 acquires the first information indicating a motion amount of the object during a period between the first time to the second time. The motion amount may be a difference in at least one of the shape, size, and position between a predetermined object included in the first image and a predetermined object included in the second image, which is generated due to the motion of the object.

The first information is described below in detail with reference to FIGS. 12 and 13.

The image reconstructor 620 may reconstruct the target image indicating the object at the target time. The target time may be set directly by the image reconstructor 620 or based on a predetermined value input by a user. Also, the target time may be a time between the first and second times. The setting of the target time by a user is described below in detail with reference to FIG. 30.

A detailed operation of the tomography apparatus 600 is described below in detail with reference to FIGS. 7 to 19.

Figure 7:
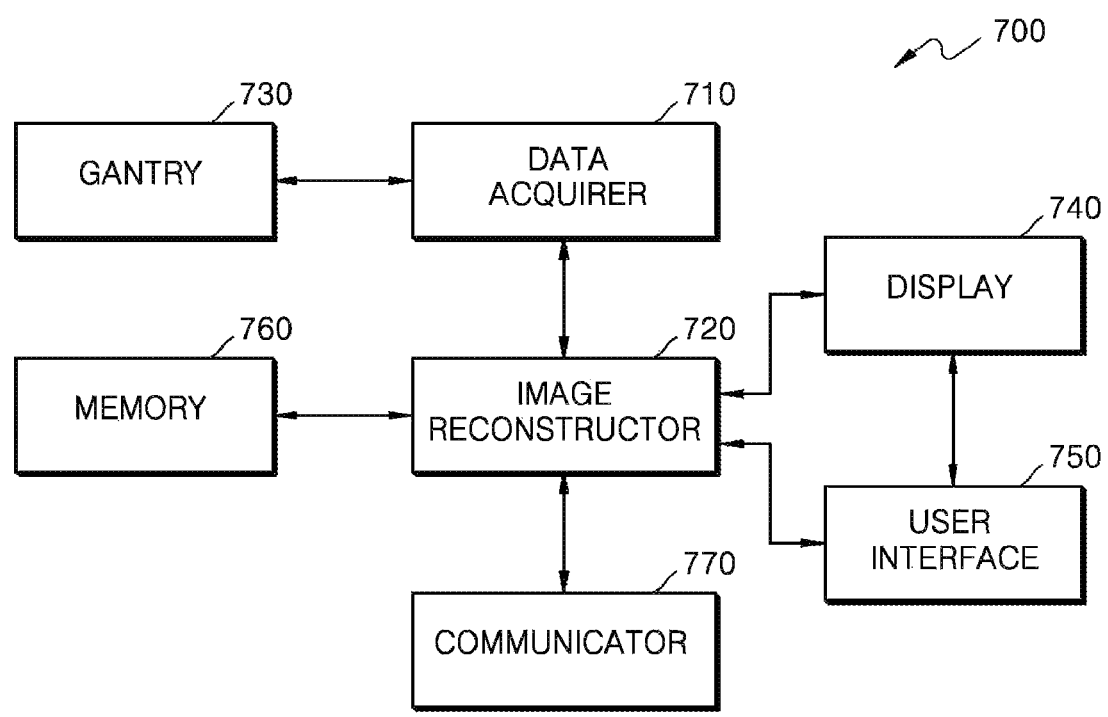
FIG. 7 is a block diagram illustrating a tomography apparatus according to another embodiment of the present invention.

FIG. 7 is a block diagram illustrating a tomography apparatus 700 according to another embodiment of the present invention;

Since a data acquirer 710 and an image reconstructor 720 of FIG. 7 identically correspond to the data acquirer 610 and the image reconstructor 620 of FIG. 6, redundant descriptions thereof are omitted.

Referring to FIG. 7, the tomography apparatus 700 may include the data acquirer 710 and the image reconstructor 720. Also, the tomography apparatus 700 may further include at least one of a gantry 730, a display 740, a user interface 750, a memory 760, and a communicator 770. Since the gantry 730, the display 740, the user interface 750, the memory 760, and the communicator 770, which are included in the tomography apparatus 700, respectively have the same operations and structures as the gantry 102, the display 130, the input unit 128, the memory 124, and the communicator 132 of the tomography system 100 of FIG. 4, redundant descriptions thereof are omitted.

The data acquirer 710 performs a tomography scan on the object and acquires the first information indicating motion of the object according to the lapse of time.

In detail, the data acquirer 710 performs a tomography scan on the object and acquires the first image corresponding to the first time and the second image corresponding to the second time. The data acquirer 710 acquires the first information indicating a relationship between the motion amount of the object and time based on the motion amount between the first image and the second image. The first image and the second image may be images that are reconstructed according to a partial angle reconstruction (PAR) method. In detail, since the first image and the second image are images reconstructed by using only the raw data acquired in an angular section, the first image and the second image are not complete images showing the entire object, but incomplete images showing only a part of the object. Also, an incomplete image showing a part of the object, such as the first and second images, may be referred to as a "partial image" or a "partial angle image".

The first time corresponds to a time point when raw data is acquired to reconstruct the first image and the second time corresponds to a time when raw data is acquired to reconstruct the second image. For example, when the first image is reconstructed by using the raw data that is acquired to reconstruct the first image during a time cycle from 0 to a time "a", the first time may be a time "a/2" that corresponds to the middle of the time cycle from 0 to the time "a". Also, when the second image is reconstructed by using the raw data that is acquired to reconstruct the second image during a time cycle from a time "b" to a time "c", the second time may be a time "(c+b)/2" that corresponds to the middle of the time cycle from the time "b" to the time "c".

Also, the first image indicates the object at the first time and the second image indicates the object at the second time.

The image reconstructor 720 reconstructs the target image showing the object at the target time, based on the first information. In detail, the image reconstructor 720 reconstructs the target image through motion correction of the object, based on the first information. In detail, the image reconstructor 720 may reconstruct the target image by warping an image indicating the object, an image grid for imaging the object, or a voxel indicating the object.

The term "warping" signifies adjustment of the object included in the image to fit to a state of an expected object through a change of the state of the object included in the image, such as, expanding, contracting, moving, and/or deshaping. An image reconstruction operation of the image reconstructor 720 is described below in detail with reference to FIGS. 13 to 31.

The gantry 730 may include the X-ray generator 106 of FIG. 4, the X-ray detector 108 of FIG. 4, and the DAS 116 of FIG. 4. The gantry 730 projects X-rays toward the object, detects the X-ray beam transmitting through the object, and generates raw data corresponding to the detected X-ray beam.

In detail, the X-ray generator 106 generates and projects X-rays toward the object while rotating around the object. Then, the X-ray detector 106 detects the X-ray beam that transmits through the object. The DAS 116 generates raw data corresponding to the detected X-ray beam.

In the following description, reconstructing one cross-sectional tomography image by using the raw data acquired as the X-ray generator 106 rotates a half turn or more and less than one turn is referred to as a half reconstruction method, and reconstructing one cross-sectional tomography image by using the raw data acquired as the X-ray generator 106 rotates one turn is referred to as a full reconstruction method. Also, in the following description, a rotation time, angle, or phase of the X-ray generator 106 that rotates to acquire raw data needed to reconstruct one cross-sectional tomography image is referred to as "one cycle". Also, the term "one-cycle angular section" may denote an angular section during which the X-ray generator 106 rotates to acquire raw data needed for the reconstruction of one cross-sectional tomography image. Also, the one-cycle angular section may denote a section of projection data needed to reconstruct one cross-sectional tomography image. In this case, it may be referred to as a one-cycle angular section of projection data.

For example, one cycle in the half reconstruction method may be 180° or more and one cycle in the full reconstruction method may be 360°. For example, the one-cycle angular section of projection data in the half reconstruction method that uses the rebinned parallel beam may be an angle of 180°+fan angle by adding a fan angle to 180°. For example, when the fan angle is about 60°, the one-cycle angular section of projection data in the half reconstruction method may be about 240° (180°+60°). Also, the one-cycle angular section in the full reconstruction method may be 420° (360°+60°) by adding the fan angle to 360°.

In detail, the first time and the second time may be times or angular positions included in one cycle. Also, the first image and the second image may be images that are respectively reconstructed by using the raw data acquired in the first angular section and the second angular section different from the first angular section which are included in the one-cycle angular section.

The display 740 displays a predetermined screen. In detail, the display 740 may display a user interface screen needed to perform a tomography scan or a reconstructed tomography image. The user interface screen displayed on the display 740 is described below in detail with reference to FIGS. 29 to 31.

The user interface 750 generates and outputs a user interface and receives an input of a predetermined command or data from a user through the user interface screen. Also, the user interface screen output from the user interface 750 is output to the display 740. Then, the display 740 may display the user interface screen. A user may recognize predetermined information or input a predetermined command or data via the user interface screen being displayed on the display 740.

For example, the user interface 750 may include an input device such as a mouse, a keyboard, or hard keys for inputting predetermined data. For example, a user may input a predetermined command or data by manipulating at least one of the mouse, the keyboard, or other input devices includes in the user interface 750.

Also, the user interface 750 may be formed as a touchpad. In detail, the user interface 750 may include a touchpad (not shown) that is coupled to a display panel (not shown) included in the display 740, and may output the user interface screen on the display panel. Then, when a predetermined command is input through the user interface screen, the touchpad senses the input and may recognize the predetermined commanded input by the user.

In detail, when the user interface 750 is formed as a touchpad, as a user touches a predetermined position on the user interface screen, the user interface 750 senses the touch position and may transmit information about the touch position to the image reconstructor 720. Then, the image reconstructor 720 may recognize a user's request or command corresponding to a menu displayed on the sensed position and may perform a tomography image reconstruction operation according to the recognized request or command.

The memory 760 may store the data acquired according to the tomography scan. In detail, the memory 760 may store at least one of projection data that is raw data and a sinogram. Also, the memory 760 may store various pieces of data or programs needed for reconstruction of a tomography image and may store a finally reconstructed tomography image. Also, the memory 760 may store various pieces of data needed for acquisition of the first information and the acquired first information.

Also, the memory 760 may include at least one storage medium from among a flash memory-type storage medium, a hard disk-type storage medium, a multimedia card microtype storage medium, card-type memories such as an SD card, an XD memory, etc., random access memory (RAM), static random access memory (SRAM), read-only memory (ROM), electrically erasable programmable ROM (EEPROM), programmable ROM (PROM), magnetic memory, a magnetic disc, and an optical disc.

The communicator 770 may communicate with an external device or an external medical apparatus. For example, the communicator 770 is connected to an external tomography system or tomography apparatus and may receive the first image and the second image. Alternatively, the communicator 770 may receive raw data to reconstruct the first image and the second image. In this case, the data acquirer 710 may receive the first image and the second image or the raw data to reconstruct the first image and the second image, via the communicator 770, and may acquire the first information based on the received data.

The tomography apparatuses 600 and 700 according to the embodiments of the present invention may be employed for all of the PAR method, the full reconstruction method, and the half reconstruction method. Also, in the tomography apparatuses 600 and 700 according to the embodiments of the present invention, a variety of scan modes are used to acquire the first image and the second image. Also, in the tomography apparatuses 600 and 700 according to the present embodiments, tomography according to both of an axial scanning method and a helical scanning method may be adopted. Also, in the tomography apparatuses 600 and 700 according to the embodiments of the present invention, the X-ray generator 106 that generates X-rays having a variety of shapes such as cone shape or parallel shape may be employed.

When the object is an object that moves, such as a heart, motion artifacts existing in a reconstructed tomography image may be reduced by acquiring raw data by reducing a time or angle corresponding to one cycle. Accordingly, the half reconstruction method may reduce motion artifacts better than the full reconstruction method. Accordingly, in the following description, a case in which the half reconstruction method is used to reconstruct the target image is described.

The image reconstruction method, the scan mode, and the shape of X-rays being projected to the object which are applicable to the tomography apparatuses 600 and 700 according to an embodiment of the present invention are described below with reference to FIGS. 8 to 10.

Figure 8A:
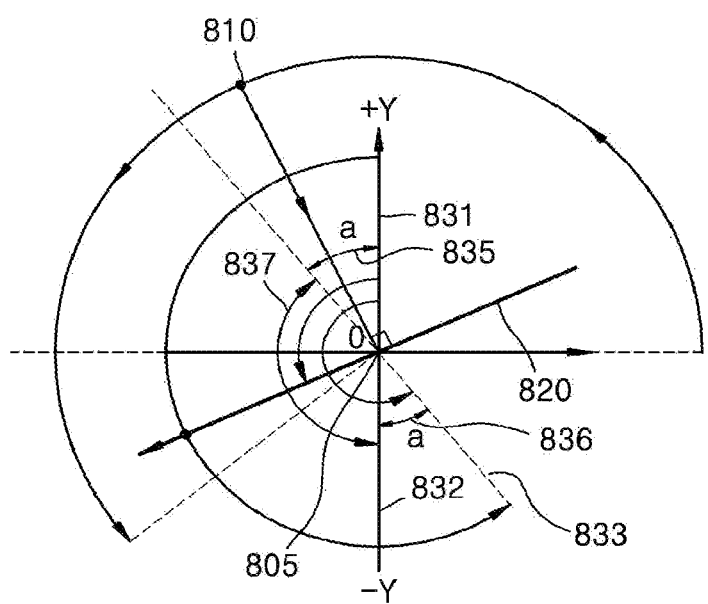
FIGS. 8A and 8B are views for describing reconstruction of a tomography image according to a half reconstruction method.
Figure 8B:
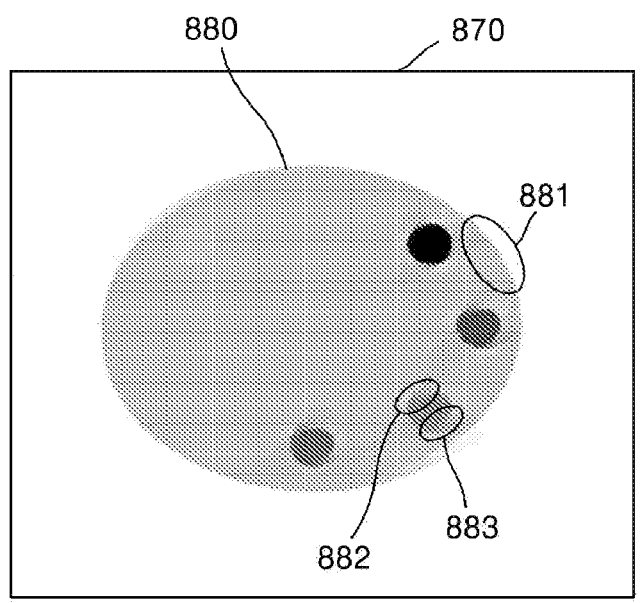

FIGS. 8A and 8B are views for describing reconstruction of a tomography image according to the half reconstruction method. In detail, FIG. 8A illustrates rotation of the X-ray generator 106. FIG. 8B is a tomography image reconstructed by the half reconstruction method.

When the X-ray generator 106 projects a cone beam having a fan shape at a predetermined position, the X-ray generator 106 performs a tomography scan while rotating by an angle equivalent to an angle of 180°+(fan angle×2) in the half reconstruction method and may reconstruct a tomography image by using raw data acquired at the angle of 180°+(fan angle×2). Also, when a reconstruction operation is performed by converting the fan beam to a parallel beam or the X-ray generator 106 projects a parallel beam, a tomography image may be reconstructed by using raw data corresponding to the angular section having an angle of 180°+fan angle in the half reconstruction method. In other words, when a cone beam is used, the amount of raw data required increases as the fan angle increases, compared to a case of reconstructing a tomography image using the raw data acquired by using the parallel beam.

Figure 10A:
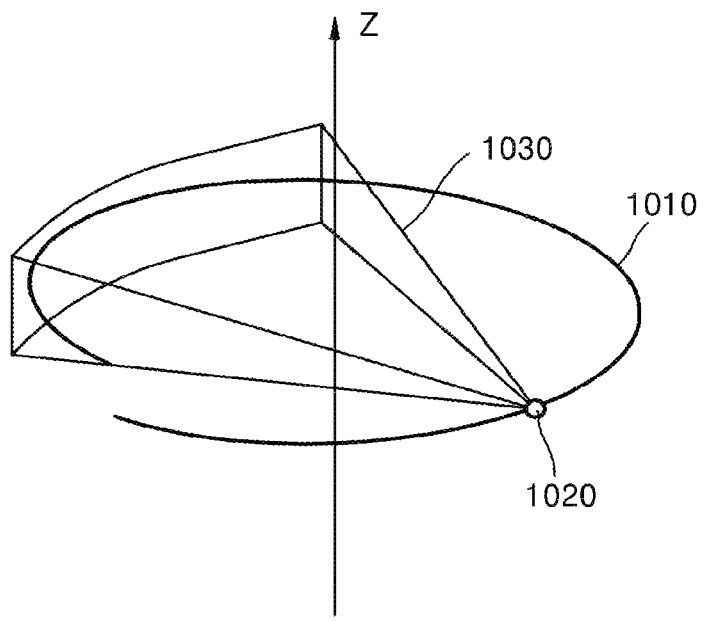
FIGS. 10A and 10B are views for describing a shape of an X-ray beam projected toward an object.
Figure 10B:
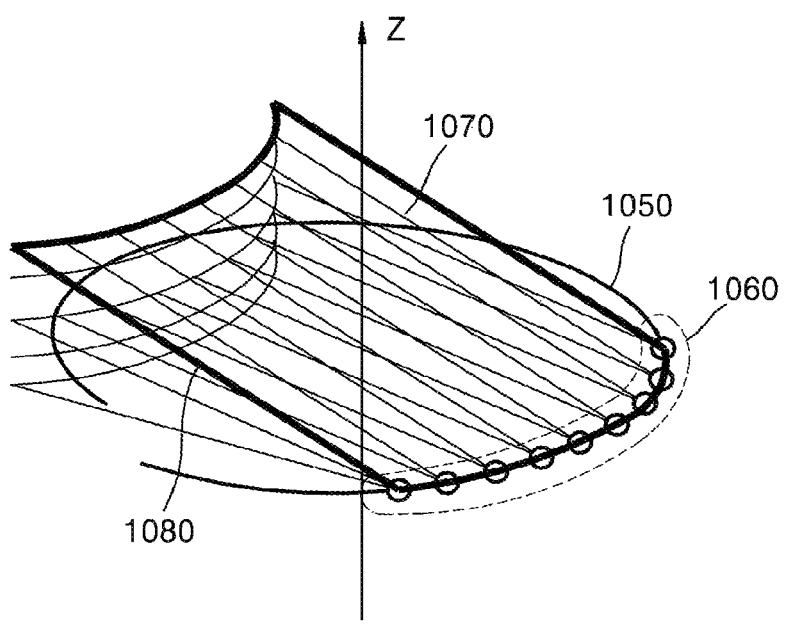

In detail, when a beam is not a cone beam but a parallel beam as described in FIG. 10B, the angle for additional rotation is decreased to be less than the fan angle "a" for the case of a cone beam and the X-ray generator 106 rotates by an angle of 180°+a as one cycle. For example, when the fan angle is 60°, the raw data acquired in the angular section of 300° (180°+2a) is needed for a case of using a cone beam and the raw data acquired in the angular section of 240° (180°+a) is needed for a case of using a parallel beam. Accordingly, when a parallel beam is used, the half reconstruction method may be performed at an angle 240° (180°+a) as one cycle.

FIG. 8A illustrates a case of using a parallel beam, in which the half reconstruction method is performed by using raw data acquired in the angular section of, for example, 180°+fan angle.

Referring to FIG. 8A, when the X-ray generator 106 at a beam position 810 projects X-rays toward an object 805, the X-ray detector 106 detects the X-rays on a detection plane 820. The beam position 810 rotates around the object 805 as a center by an angle of 180°+a, which is one cycle. Also, the detection plane 820 rotates corresponding to the beam position 810. In detail, the beam position 810 moves by 180° from a +Y axis to a −Y axis and further moves by the fan angle equivalent to "a", to a position 833.

In the half reconstruction method, one cross-sectional tomography image is reconstructed by using pieces of projection data acquired in a first "a" angular section 835, an intermediate angular section 837, and a last "a" angular section 836.

Referring to FIG. 8B, a tomography image 870 that is reconstructed by using raw data acquired by the half reconstruction method is illustrated.

Since X-rays are projected in the faced direction toward the object in the first "a" angular section 835 and the last "a" angular section 836, the first "a" angular section 835 and the last "a" angular section 836 have the same view. Accordingly, a portion of the object reconstructed by using the projection data acquired in the first "a" angular section 835 and a portion of the object reconstructed by using the projection data acquired in the last "a" angular section 836 are identical to each other.

For a moving object, when data is acquired at different times even if the data is acquired for the same portion of the object, different pieces of data are acquired due to the motion of the object. A state of the object in the first "a" angular section 835 and a state of the object in the last "a" angular section 836 are different from each other. Accordingly, motion artifacts may be generated most severely in a portion of the object that is imaged by using the projection data acquired in the first "a" angular section 835 and the projection data acquired in the last "a" angular section 836 in which the portion of the object which is the same as that of the object in the first "a" angular section 835 is imaged.

Referring to FIG. 8B, it may be seen that motion artifacts are generated in surface portions 882 and 883 indicating the object in the tomography image 870 reconstructed in the half reconstruction method.

However, compared to the full reconstruction method, the half reconstruction method has a small angular section for acquiring projection data. Accordingly, in the tomography image 870 reconstructed by the half reconstruction method, motion artifacts may be reduced compared to the tomography image acquired by the full reconstruction method. For example, compared to the outermost surface 230 of the object 210, which is in the tomography image 200 illustrated in FIG. 2 and is blurred, an outermost surface 881 of an object 880 in the tomography image 870 of FIG. 8B is less blurred.

Figure 2:
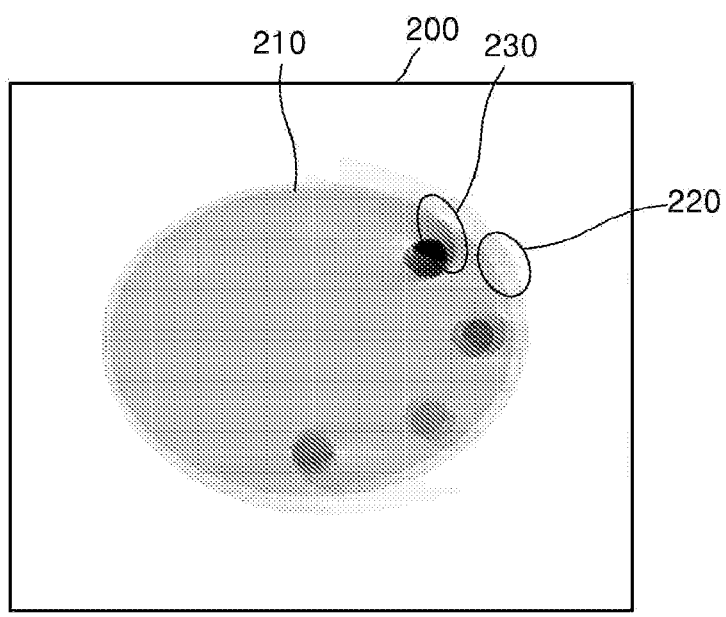
FIG. 2 is a view for describing motion artifacts existing in a reconstructed tomography image.

Also, it may be seen that blurring is reduced in inner surfaces 882 and 883 compared to the tomography image 200 of FIG. 2 and thus motion artifacts are generally reduced in the reconstructed tomography image 870.

As described above, in the tomography image 870 reconstructed in the half reconstruction method, motion artifacts may be reduced compared to the tomography image reconstructed in the full reconstruction method. In other words, as the time for acquiring raw data needed to reconstruct a cross-sectional tomography image decreases, an image having reduced motion artifacts may be reconstructed. In other words, as the time for acquiring raw data needed to reconstruct one cross-sectional tomography image decreases, a temporal resolution may be increased and a dose of radiation exposed to a patient may be reduced. The tomography apparatus according to the present embodiment and the method for reconstructing a tomography image thereof may employ the above-described full reconstruction method or half reconstruction method.

Accordingly, in order to increase a temporal resolution in the present embodiment, the first image corresponding to the first time and the second image corresponding to the second time are acquired by using the PAR method in which an image is reconstructed by acquiring raw data at a partial angle. The first image and the second image are described below in detail with reference to FIG. 11.

Also, the tomography apparatuses 600 and 700 according to the embodiments of the present invention may acquire the first image and the second image by performing a tomography scan according to a variety of scan modes. A scan mode used for a tomography scan may include a prospective mode and a retrospective mode, which is described below in detail with reference to FIGS. 9A and 9B. Also, the tomography apparatuses 600 and 700 according to the present embodiments may perform a tomography scan according to a variety of scanning methods. The scanning method used for tomography includes an axial scanning method and a helical scanning method, which is described in detail with reference to FIG. 9.

Figure 9A:
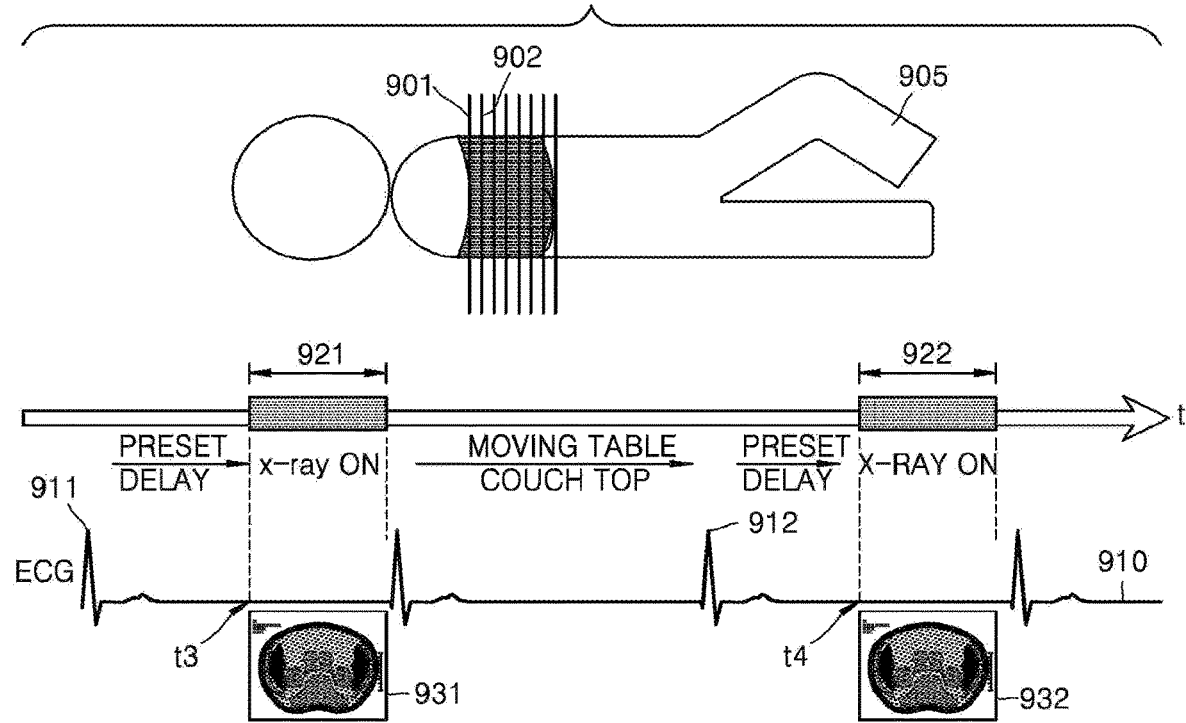
FIGS. 9A and 9B are views for describing a scan mode for a tomography scan.
Figure 9B:
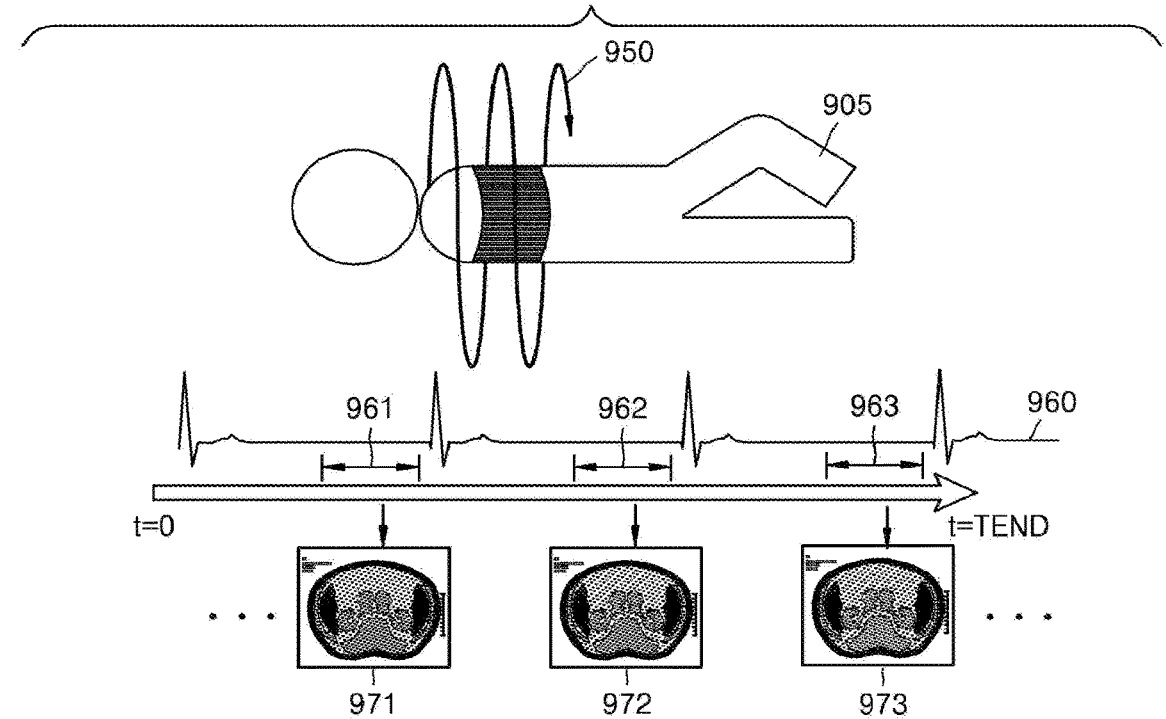

FIGS. 9A and 9B are views for describing a scan mode and a scanning method applied to a tomography scan. In detail, FIG. 9A is a view for describing a tomography scan according to an axial scanning method. Additionally, FIG. 9A is a view for describing a tomography scan according to a prospective mode. FIG. 9B is a view for describing a tomography scan according to a helical scanning method. Additionally, FIG. 9B is a view for describing a tomography scan according to a retrospective mode. The scan mode may be determined according to whether a heartbeat rate of a patient that is subject to imaging is constant or not. Also, electrocardiographic (ECG) gating may be used to acquire raw data that is used for reconstruction of an image. In FIGS. 9A and 9B, while a tomography scan is performed, the table 105 of FIG. 4 is moved in an axial direction of a patient 905.

Referring to FIG. 9A, the axial scanning method is a tomography method in which X-rays are projected for scanning while the table 105 of FIG. 4 is stopped, the table 105 is moved by a predetermined interval from 901 to 902, and X-rays are projected for a predetermined section 922, thereby obtaining raw data. The tomography apparatuses 600 and 700 according to the present embodiments perform a tomography scan by using the axial scanning method and thus at least one of the first image, the second image, and the target image may be obtained.

Referring to FIG. 9A, for a person having a constant heart beat rate, an ECG signal 910 is regularly gated by employing a prospective mode. In the prospective mode, a predetermined section 921 is automatically selected at a time t3 that is spaced apart from an R peak 911 by a predetermined time. X-rays are applied to the object during the gated predetermined section 921 to acquire raw data. A predetermined section 922 is automatically selected at a time t4 that is spaced apart from a subsequent R peak 912 by a predetermined time. The X-rays are projected in order to scan the object while the table 105 of FIG. 4 is stopped. After the table 105 is moved at a predetermined interval from 901 to 902, X-rays are projected during the predetermined section 922 to acquire raw data. Of the half reconstruction method, a method of performing a tomography scan by moving in an axial direction of the object as illustrated in FIG. 9A is referred to as an axial half reconstruction method. The tomography apparatuses 600 and 700 according to the present embodiments may employ the axial scanning method.

The data acquirer 710 reconstructs tomography images 931 and 932 acquired in the gated sections 921 and 922.

Referring to FIG. 9B, the helical scanning method is a tomography method in which X-rays are continuously projected for tomography while the table 105 of FIG. 4 is moved at a predetermined time from t=0 to t=end. In detail, a tomography scan is performed by continuously projecting X-rays to an object while the table 105 of FIG. 4 on which the patient 905 including the object is laid is moved for a predetermined time at a predetermined speed. Accordingly, a motion trajectory 950 of the X-ray source may be a helix form.

Referring to FIG. 9B, when a heartbeat rate of a patient is irregular, as in the case of an arrhythmia patient, regularity of a heart beat rate is degraded and thus it is impossible to uniformly detect the cycle as in the prospective mode. In this case, an ECG signal 960 is irregularly gated in the retrospective mode. In the retrospective mode, X-rays are projected toward the object in all cycles of ECG signals or in a consecutive predetermined range of ECG signals to acquire raw data, and then partial cycles for reconstruction of a tomography image are selected. In other words, in the retrospective mode, partial cycles used by a user for image reconstruction are individually set to detect partial cycles 961, 962, and 963, and then the raw data acquired during the detected cycles are used for reconstruction of a tomography image.

In the retrospective mode, X-rays are continuously projected from a certain time t=0 to t=end, thereby performing a tomography scan. Also, since the table 105 of FIG. 4 continuously moves at a predetermined speed for a predetermined time, the motion trajectory 950 of an X-ray light source (not shown) is in a helix form. Among the half reconstruction method, the method of performing an X-ray scan by continuously projecting X-rays while the table is moved as illustrated in FIG. 9B is referred to as a helical half reconstruction method. The tomography apparatuses 600 and 700 according to the present embodiments may employ a helical half reconstruction method.

In a detailed example, for a patient having an irregular heartbeat rate, a tomography scan may be performed by applying a retrospective mode to the helix scanning method. Also, for a patient having a regular heart beat rate, a tomography scan may be performed by applying a prospective mode to the axial scanning method. However, the present invention is not limited thereto and a tomography scan may be performed by applying the prospective mode to the helical scanning method and the retrospective mode to the axial scanning method.

FIGS. 10A and 10B are views for describing a shape of an X-ray beam projected toward the object. In detail, FIG. 10A illustrates an example in which the X-ray generator 106 projects X-rays in the form of a cone beam. FIG. 10B illustrates an example in which the X-ray generator 106 projects X-rays in the form of a parallel beam.

Referring to FIG. 10A, when the X-ray generator 106 moves along a trajectory 1010 and projects X-rays at a predetermined position 1020, the X-rays are projected toward the object in a cone shape 1030, as illustrated in FIG. 10A.

Referring to FIG. 10B, when the X-ray generator 106 moves along a trajectory 1050 and projects an X-ray at predetermined positions 1060, the X-rays are projected toward the object in a parallel plane shape 1070, as illustrated in FIG. 10B.

Referring to FIG. 10B, when the X-ray generator 106 projects X-rays in the form of a cone beam, the beams projected in the form of a cone are rearranged and thus the beams may be rearranged in parallel on a plane 1080 that is formed by connecting the row of the X-ray detector 108 and the trajectory 1060 at which the X-ray generator 106 is positioned. In other words, the cone beam may be converted into a pseudo parallel-beam for use. Also, when the cone beam is converted into a parallel beam for use, in the cone beam, raw data is acquired as the X-ray generator 106 further rotates the fan angle "a", compared to the parallel beam. In detail, when the fan angle is "a", the X-ray generator 106 that projects a cone beam uses the raw data acquired in the angular section having an angle of 180°+2a to acquire raw data corresponding to the angular section having an angle of 180°+a corresponding to the rebinned parallel beam.

As described with reference to FIG. 10, the tomography apparatuses 600 and 700 according to the present embodiments may be applied to both of the CT apparatus irradiating a cone beam and a CT apparatus irradiating a parallel beam.

In the following description, for convenience of explanation, in the one-cycle angular section that is an angular section that the X-ray generator 106 rotates to acquire projection data needed for acquiring one cross-sectional tomography image, an angular section except for 180° may be referred to as an additional angle. In the above-described example, when the parallel beam obtained by rebinning the cone beam projected from the X-ray generator 106 is used, the additional angle may be "2a". When the parallel beam is used, the additional angle may be "a". When the rebinned parallel beam is used, the projection data corresponding to the angular section having an angle of 180°+a is acquired by using the raw data acquired as the X-ray generator 106 which projects X-rays in the form of a cone beam rotates angular section having an angle of 180°+2a.

Also, assuming a section of the projection data acquired to reconstruct one cross-sectional tomography image to be the one-cycle angular section, the additional angle may signify an angular section obtained by subtracting 180° from the one-cycle angular section of the projection data. In the above-described example, when the X-ray generator 106 rotates the angular section having an angle of 180°+2a projecting a cone beam and the projection data corresponding to the angular section having an angle of 180°+a is acquired by using the rebinned parallel beam, the one-cycle angular section of the projection data may be 180°+a and the additional angle in the one-cycle angular section of the projection data may be "a".

In the tomography apparatus 700 according to the present embodiment, the PAR method of reconstructing an image by using raw data acquired in the partial angle section is used to acquire the first image and the second image. In detail, the first image and the second image may be images reconstructed by using the raw data acquired in the first angular section and the second angular section which are included in one-cycle angular section and are different sections from each other. The acquisition of the first image and the second image according to partial reconstruction is described below in detail with reference to FIGS. 11 and 12.

Since the X-ray generator 106 rotates at a constant speed and performs a tomography scan, an angular value is proportional to a time value. Accordingly, as a value of a predetermined angular section decreases, a time spent to acquire raw data in the predetermined angular section decreases. Thus, in the PAR method, as the angular section used to reconstruct a partial angular image decreases, the temporal resolution may be increased. Thus, the first and second images that are partial angular images are images having a high temporal resolution, in which motion artifacts hardly exist. The first and second images may accurately show a part of the object without blurring.

Figure 11:
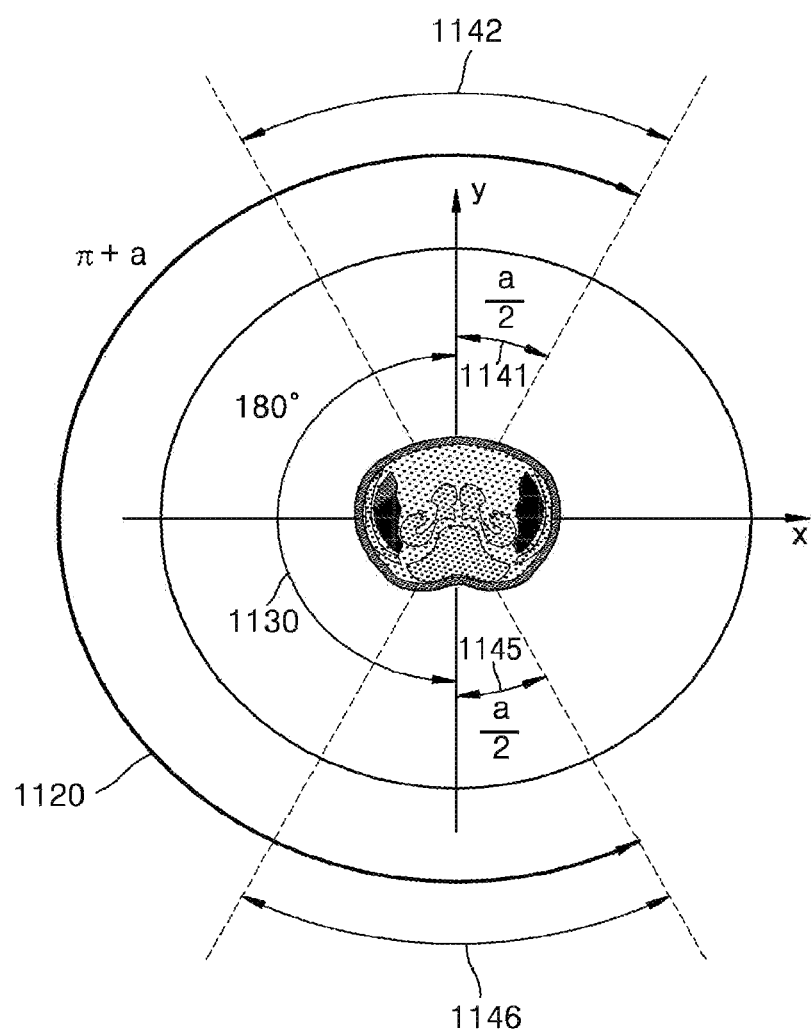
FIG. 11 is a view for describing an operation of a tomography apparatus according to an embodiment of the present invention.

FIG. 11 is a view for describing an operation of the tomography apparatus 700 according to an embodiment of the present invention.

In the following description, a case of performing a tomography scan as the X-ray generator 106 rotates by an angle of 180°+an additional angle as the one-cycle angular section by employing the half reconstruction method described in FIG. 8, is described as an example. As described above, in the half reconstruction method, the additional angle that is an angular section except for 180° may vary according to at least one of the shape of a beam, specification of a tomography system, and the product specification of the X-ray generator 106.

In the following description, a case of using the rebinned parallel beam is described as an example. Accordingly, a case in which the X-ray generator 106 rotates the angular section having an angle of 180°+2a and projects a cone beam, the data acquirer 710 acquires raw data, for example, projection data, corresponding to the angular section having an angle of 180°+a by using the data acquired as the X-ray generator 106 rotates the angular section having an angle of 180°+2a, is described as an example. Also, in the drawings and the detailed descriptions to be referred to, a case in which the one-cycle angular section has an angle of 180°+ fan angle, that is, 180°+a and the additional angle is the fan angle, that is, "a", according to the angular section of the projection data acquired by using the rebinned parallel beam, is described and illustrated as an example.

Referring to FIG. 11, an one-cycle angular section 1120 may have angle of 180°+an additional angle which is a sum of 180° 1130, (a/2)° 1141, and (a/2)° 1145. Also, a detailed value of the fan angle "a" may vary according to a tomography system or the product specification of the X-ray generator 106 and may be, for example, about 50°-60°.

In detail, the first angular section 1142 and the second angular section 1146 are angular sections included in the one-cycle angular section 1120 and may be conjugate angles that are angles facing each other. A difference in angle between the first angular section 1142 and the second angular section 1146 in the conjugate-angle relationship is 180°.

In detail, as illustrated in FIG. 11, the first angular section 1142 may be a start section of the one-cycle angular section 1120 and the second angular section 1146 may be the last section of the one-cycle angular section 1120.

When the first angular section 1142 and the second angular section 1146 have the conjugate-angle relationship, since views according to the first angular section 1142 and the second angular section 1146 are identical with each other, a surface of the object 1110 detected when an image of the object 1110 is captured in the first angular section 1142 and a surface of the object 1110 detected when an image of the object 1110 is captured in the second angular section 1146 are identical with each other.

For example, the "a" in FIG. 11 may be 60° (a=60°), and raw data corresponding to a 60° angular section is acquired as the X-ray generator 106 rotates. Accordingly, the first image and the second image are acquired by using the raw data acquired in the first angular section 1142 that is a first 60° section and the second angular section 1146 that is a last 60° section.

Since the X-ray generator 106 rotates at a constant speed and performs a tomography scan, an angular value is proportional to a time value. Accordingly, as a value of a predetermined angular section decreases, the time consumed to acquire the raw data in a predetermined angular section is decreased.

As described above, the tomography apparatus 700 uses the PAR method in which the first image and the second image are acquired by using the raw data acquired in the first angular section 1142 and the second angular section 1146 that are partial sections included in the one-cycle angular section. In other words, since the tomography apparatus 700 reconstructs an image by using a relatively small angular section compared to the half reconstruction method or the full reconstruction method, the temporal resolution may be increased and motion artifacts may be reduced. Also, in the present embodiment, since a motion amount of the object is measured by using the first image and the second image that are partial angle images, the motion amount of the object may be measured more accurately.

Since the target image is generated by performing motion correction on the object at the target time by using the first information that is motion information including the accurately measured motion amount, the target image which is reconstructed may have a high temporal resolution and reduced motion artifacts. The tomography apparatus according to the present embodiment and the tomography image reconstruction method thereof, which may reduce motion artifacts and increase the temporal resolution, are described below in detail with reference to FIGS. 12 to 25.

FIG. 12 is a view for describing the operation of the tomography apparatus 700 according to an embodiment of the present invention.

Referring to FIG. 12, an angle of 180°+a is set to be a one-cycle angular section 1210 and raw data needed for reconstruction of the first image and the second image is acquired in a first angular section 1211 and a second angular section 1212 which are included in the one-cycle angular section 1210 and have a conjugate-angle relationship. In detail, the first angular section 1211 may be a start section in the one-cycle angular section 1210 and the second angular section 1212 may be the last section in the one-cycle angular section 1210.

In detail, the X-ray generator 106 performs a tomography scan while rotating around an object 1201, thereby acquiring projection data, a sinogram, etc., which is raw data corresponding to the first angular section 1211. Accordingly, a tomography image 1231 is reconstructed by using the acquired raw data.

The raw data acquired in the first angular section 1211 and the second angular section 1212 may be data that is acquired by detecting the X-rays projected to the object from a single source or a dual source. For example, when a tomography scan is performed by using a single source, the tomography scan may be performed by moving the single source in the first angular section 1211 and the second angular section 1212.

In another example, when a tomography scan is performed by using a dual source, the tomography scan may be performed by moving at least one of a first source and a second source included in the dual source in at least one of the first angular section 1211 and the second angular section 1212. In detail, raw data may be acquired as the first source rotates in the first angular section 1211, and raw data may be acquired as the second source rotates in the second angular section 1212. Also, raw data may be acquired as the first source rotates in the first angular section 1211 or a first angular section 2001 of FIG. 20A, and the second angular section 1212 or a second angular section 2005 of FIG. 10A. Also, raw data may be acquired as the second source rotates in an at least partial angular section of the one-cycle angular section 1120, except for the first angular section 1211 and the second angular section 1212, for example, at least one of a third angular section 2002, a fourth angular section 2003, and a fifth angular section 2004 which are described below with reference to FIG. 20A.

In doing so, various reconstruction methods may be used for reconstruction of a tomography image. For example, as a method of reconstructing a tomography image in the tomography apparatuses 600 and 700, a filtered back-projection method, an iterative method, etc. may be used.

According to the back-projection method, an image is reconstructed by back-projecting projection data acquired in a plurality of views to a pixel plane and summing the back-projected data. In detail, the back-projection method may acquire an image similar to a real image by using multiple pieces of projection data in a plurality of directions. Also, filtering may be additionally performed to remove artifacts existing in a reconstructed image and to improve image quality.

The filtered back-projection method is an improvement to the back-projection method and removes blurring or artifacts that may occur in the back-projection method. According to the filtered back-projection method, raw data is filtered before back-projection is performed and the filtered raw data is back-projected, thereby reconstructing a tomography image.

The filtered back-projection method is generally widely used for reconstruction of a tomography image, is a method that may be simply embodied, and is effective in terms of a calculation amount for image reconstruction. The filtered back-projection method is a method that mathematically induces a reverse transformation from a Radon transformation, which is a process of acquiring a sinogram from a 2D image. According to the filtered back-projection method, it is relatively simple to extend a 2D image to a 3D image. In detail, in the filtered back-projection method, an image is reconstructed by performing back-projection after filtering projection data by using a Shepp-Logan filter that is a type of high pass filter. In the following description, a case of reconstructing a tomography image by using a filtered back-projection method is described as an example.

Referring to FIG. 12, the data acquirer 710 acquirers the tomography image 1231 by performing filtered back-projection on the raw data acquired in the first angular section 1211. In detail, the first and second angular sections 1211 and 1212 each have a value less than 180°. In order to further clarify images of surfaces 1235 and 1236 in the tomography image 1231, the tomography image 1231 is filtered and thus a first image 1232 that is finally reconstructed may be acquired. In detail, the first image 1232 may be an incomplete image that is reconstructed by the PAR method.

In detail, when the rebinned parallel beam is used and the one-cycle angular section of projection data is 180°+a, the additional angle "a" may be set to be a fan angle. In detail, the first angular section 1211 and the second angular section 1212 having the additional angle "a" may be set to be about 30°-70°.

In detail, the first angular section 1211 and the second angular section 1212 may be set to be an experimentally optimized value to obtain the first and second images having a high temporal resolution, and may be set considering the temporal resolution of the first and second images, product specifications of the tomography apparatus 700, and/or an environment for imaging. The angular values of the first angular section 1211 and the second angular section 1212 and the temporal resolutions of the first image 1232 and the second image 1242 may be in a trade-off relationship. In detail, as the angular values of the first angular section 1211 and the second angular section 1212 decrease, the temporal resolutions of the first image 1232 and the second image 1242 increase. However, when the angular values of the first angular section 1211 and the second angular section 1212 decrease, a surface portion of the object to be imaged decreases. Accordingly, as the angular values of the first angular section 1211 and the second angular section 1212 decrease, the surface portion of the object to extract a motion amount of the object decreases and thus information about motion may become relatively inaccurate.

Accordingly, considering the temporal resolutions of the first image 1232 and the second image 1242 and accuracy in the motion information obtained through the first image 1232 and the second image 1242, the angular values of the first angular section 1211 and the second angular section 1212 may be set to be optimal.

The data acquirer 710 acquires a tomography image 1241 by performing filtered back-projection on the raw data acquired in the second angular section 1212. In order to further clarify images of surfaces 1245 and 1246 in the tomography image 1241, the tomography image 1241 is filtered and thus a second image 1242 that is finally reconstructed may be acquired. In detail, the second image 1242 may be an incomplete image that is reconstructed by the PAR method.

In FIG. 12, a case of reconstructing a 2D tomography image, for example, the first and second images 1232 and 1242 is illustrated as an example. An object that is presented as a surface in a 3D tomography image may be presented as an edge, for example, the edges 1235 and 1236, as in the first and second images 1232 and 1242 illustrated in the 2D tomography image.

As illustrated in FIG. 12, when first information is acquired by using only the first and second images 1241 and 1242 that are 2D tomography images, a degree of motion of the object may be identified by comparing a difference in the edge. For example, the surfaces 1235 and 1245, which are respectively included in the first and second images 1241 and 1242 and show the same surface of the object, are compared to acquire first information.

Also, a 3D tomography image is reconstructed and first and second images that are 3D tomography images may be used. When a 3D tomography image is reconstructed from the first and second images, a motion amount of an object may be identified by comparing a difference in the edge as shown in each of the first and second images and showing the same surface.

The data acquirer 710 may acquire the first image 1241 and the second image 1242 by using the raw data that is acquired by using tomography according to the axial scanning method or the helical scanning method described in FIG. 9A.

Also, the first image 1241 and the second image 1242 may be referred to as one partial image pair.

The data acquirer 710 may acquire the first image 1241 and the second image 1242 by using the helical scanning method described with reference to FIG. 9B. When the helical scanning method is used, projection data of a plurality of views that project the same portion of the object are divided into conjugate view sectors and thus the first image and the second image may be acquired.

Also, when the first image 1241 and the second image 1242 are referred to as one partial image pair, the first information may be acquired by using a plurality of partial image pairs.

In detail, since the pieces of projection data corresponding to the entire view are acquired in the helical scanning method, the pieces of projection data of the entire view are divided into a plurality of conjugate view sectors, and thus the first image and the second image may be acquired in each of the conjugate view sectors. Accordingly, a plurality of partial image pairs corresponding to the conjugate view sectors may be obtained. Accordingly, the data acquirer 710 may obtained the first information by using the partial image pairs. In this case, the motion of the object may be more accurately predicted for each of the conjugate view sectors included in the one-cycle angular section of the first information by using the partial image pairs.

Also, the X-ray detector 108 of FIG. 4 including a 2D detector array acquires projection data corresponding to a plurality of rows at a time and a tomography scan is performed by using the helical scanning method, a plurality of pieces of raw data to acquire the partial image pairs in the same conjugate view sector for imaging the same position or same portion of the object may be acquired. For example, when the table moves in the z-axis direction and a tomography scan is performed on an axial section, the partial image pairs may be acquired at the same z-axis position of the object.

In the following direction, a case in which the table is moved in the z-axis direction and a tomography scan is performed on the axial section, as illustrated in FIG. 9B, is described as an example. In detail, when a tomography scan is performed by the helical scanning method, a plurality of raw data sets may be acquired with respect to the same axial position on the z axis (hereinafter, referred to as the same z-position) due to the motion of the table. For example, a value of a helical pitch that is a movement interval of the table in the helical scanning method is set and thus the table is moved by an interval of k-number of rows of the detector. In this case, the projection data obtained in the i-th row of the detector at the first rotation may be the same as the projection data obtained in the (i+k)th row of the detector at the second rotation after the table is moved by the helical pitch. The second rotation may be a rotation following the first rotation. Accordingly, a pair of partial images may be acquired by using the projection data obtained in the i-th row at the first rotation, and at least one pair of partial images may be acquired by using the projection data obtained in the (i+k)th row at the second rotation following the first rotation.

Alternatively, in the helical scanning method, a pair of partial images may be acquired by using the projection data obtained in the i-th row, and at least one pair of partial images may be acquired by interpolating pieces of projection data obtained in rows neighboring the i-th row.

Accordingly, the data acquirer 710 may acquire a plurality of partial image pairs corresponding to the same z-position by performing the tomography scan in the helical scanning method. Then, the first information may be acquired by using the partial image pairs. In detail, when a motion amount of the object is measured by using the partial image pairs, the motion amount of the object may be more accurately measured compared to a case of measuring the motion amount of the object by using one partial image pair and accordingly the first information that is more accurate may be acquired.

In the following description, a case in which the first and second images 1232 and 1242 are 2D tomography images as illustrated in FIG. 12 and the surface of an object is illustrated as the edge shown in the first and second images is described as an example.

Referring to FIG. 12, the first image 1232 and the second image 1242 identically express an edge included in a predetermined portion of the object.

As described above, since the first angular section 1211 and the second angular section 1212 have a conjugate-angle relationship, the first image 1232 and the second image 1242 both display the same edge of the same portion of the object. Accordingly, when the first image 1232 and the second image 1242 are compared with each other, a difference between the surfaces of the same portions of the object included in the first image 1232 and the second image 1242 may be seen and a degree of motion of the object may be recognized. When a moving object is to be tomography scanned, at least one of the size, position, and shape of the object included in the first image 1232 is different from that of the object included in the second image 1242 due to motion of the object.

Also, in detail, motion of the object in a direction, for example, an x-axis direction, perpendicular to a direction, for example, a direction 1215, in which X-rays are projected toward the object in the first angular section 1211 and the second angular section 1212, may be more accurately identified than in a different direction (view?).

Also, when the raw data acquired in an angular section having a relatively small angle, for example, a=60°, compared to the half reconstruction method or the full reconstruction method, is used, since information about motion of the object is acquired by using the first image 1232 and the second image 1242 having a high temporal resolution and less motion artifacts, the amount of the motion of the object between the first time and the second time may be accurately measured.

The data acquirer 710 acquires first information indicating motion of the object according to the lapse of time based on the motion amount between the first image 1232 and the second image 1242. The operation of acquiring the first information is described below in detail with reference to FIG. 13.

Figure 13A:
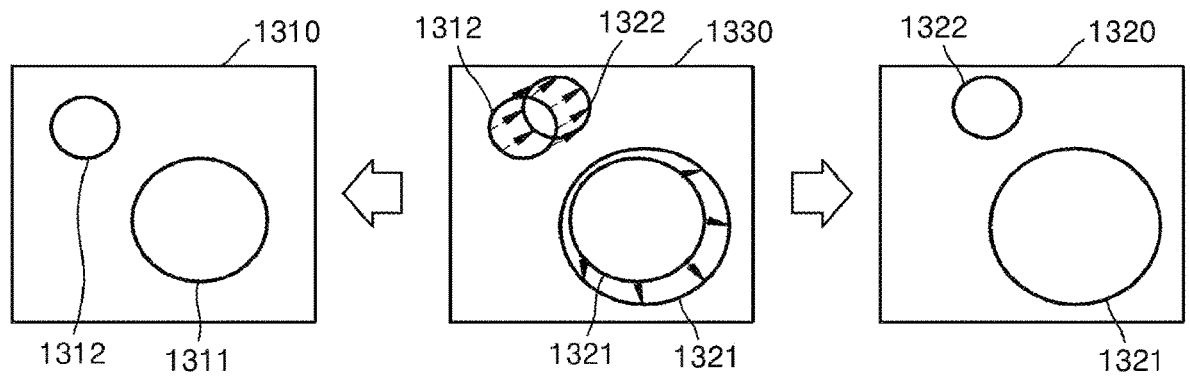
FIGS. 13A, 13B, and 13C are views for describing motion of an object.
Figure 13B:
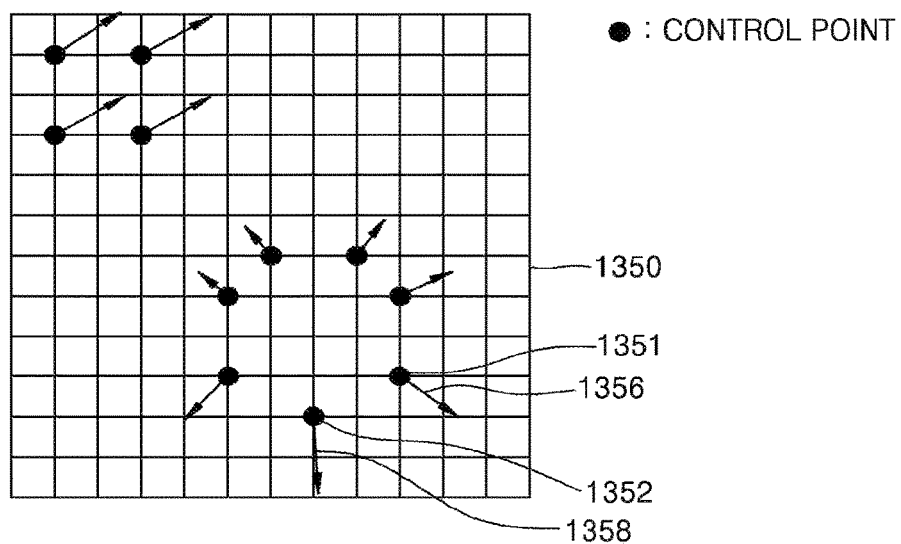
Figure 13C:
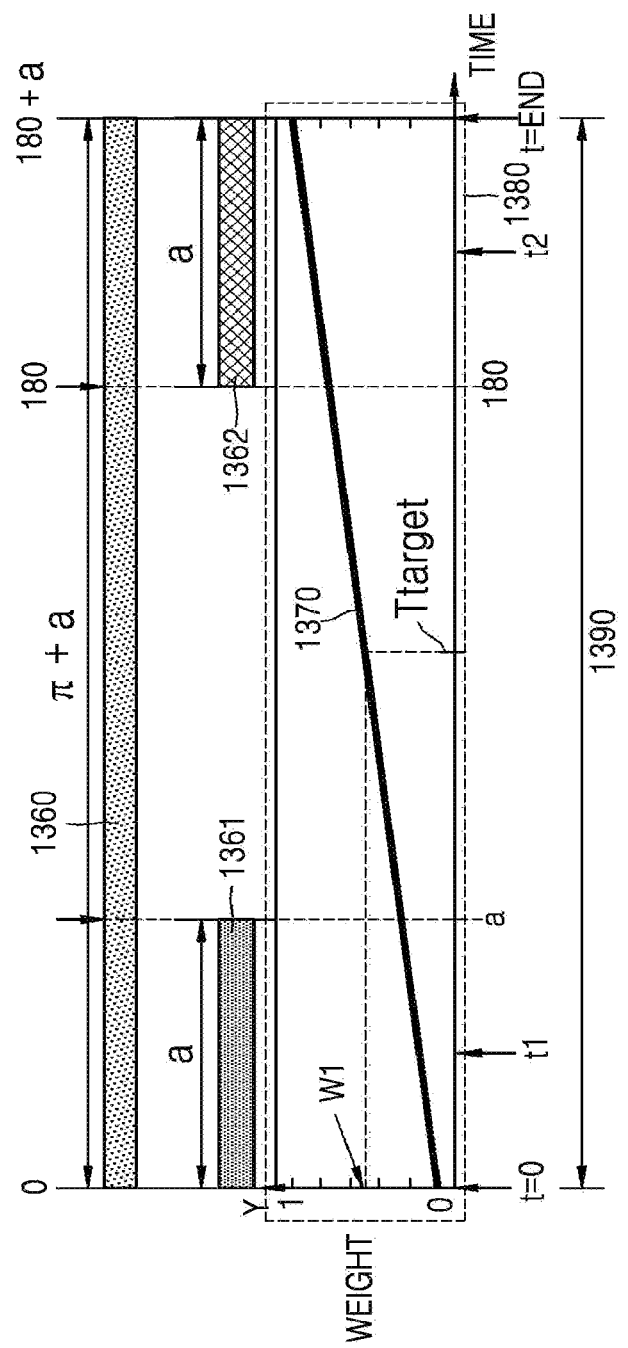

FIGS. 13A, 13B, and 13C are views for describing motion of an object. In detail, FIG. 13A is a view for\ describing comparison of motion between the first image and the second image. FIG. 13B is a view for describing a motion amount between the first image and the second image. FIG. 13C is a view for describing the first information.

Referring to FIG. 13A, a first image 1310 and a second image 1320 are partial images that identically correspond to the first image 1232 and the second image 1242 of FIG. 12. However, for convenience of explanation, a case in which the first image 1310 and the second image 1320 are complete images is described as an example.

The first image 1310 and the second image 1320 are tomography images that schematically illustrate a moving object by capturing images thereof. Also, in FIG. 13A, at least one of objects 1311 and 1312, or 1321 and 1322 included in one image is expressed as a circular object.

In detail, in order to compare the amounts of motions of the objects, objects 1311 and 1312 included in the first image 1310 are compared with objects 1321 and 1322 included in the second image 1320. According to a result of the comparison, the motion amount of each of the objects may be obtained as illustrated in a comparative image 1330.

Referring to FIG. 13B, the surfaces indicating the same portions of the objects included in the first and second images 1310 and 1320 are compared with each other and thus motion vectors indicating positional difference values and directions between the compared surfaces may be obtained. The motion vector may be used as the amount of the motion of the object. Information that includes motion vectors and indicates a motion amount of a predetermined portion of the object may be a motion vector field (MVF). In other words, the MVF indicates a motion amount of a surface forming the object.

The MVF is information acquired for extraction of motion of the object and the motion amount of the object may be measured by using non-rigid registration. Also, the motion amount of the object may be measured by using a variety of motion measurement techniques such as rigid registration, an optical flow technique, and a feature matching technique.

In the following description, a case of using the non-rigid registration to acquire the MVF is described as an example.

In detail, a plurality of control points, for example, control points 1351 and 1352, are set in an image grid of the first image 1310 or the second image 1320 and an optimal motion vector, for example, motion vector 1356 and/or 1358 is calculated at each control point. The motion vector is a vector including the direction and size of motion. The motion vectors at the respective control points are interpolated to obtain the MVF indicating motion vectors in all voxels. For example, a B-spline free form deformation method may be used as the motion vector interpolation method. Also, an optimization technique may be used as a method of calculating an optimal motion vector at each control point. In detail, according to the optimization technique, the MVF is updated by repeatedly updating a motion vector at the control points, the first image 1310 or the second image 1320 are warped based on the updated MVF, and the warped first image or the second image are compared with the second image 1320 or the first image 1310 before warping. When a degree of similarity between an image before warping and an image after warping is the highest, the repetition is terminated and a motion vector is calculated. The degree of similarity may be indicated by using a negative value of a sum of squared difference of brightness values of two images to be compared.

In another method, the motion vectors may be obtained by setting a plurality of control points on a surface of the object and comparing the control points indicating the same positions in the objects in the first image 1310 and the second image 1320. In detail, a relative difference between the control points is obtained by matching the control points of the object in the first image 1310 to the control points of the object in the second image 1320. A relative difference value may be used as a motion vector at a current control point. The MVF indicating motion vectors at all voxels is obtained by interpolating the motion vectors at the respective control points. As in the above-described example, the B-spline free form deformation method may be used as the motion vector interpolation method.

Referring to FIG. 13C, since a one-cycle angular section 1360, the first angular section 1361, and the second angular section 1362 identically correspond to the one-cycle angular section 1210, the first angular section 1211, and the second angular section 1212, which are described in FIG. 12, detailed descriptions thereof are omitted here.

Also, in FIG. 13C, which is a graph showing the first information 1380, an x-axis denotes a one-cycle angular section or a time corresponding to one cycle, whereas a y-axis denotes a weighting value W corresponding to a motion amount.

In detail, the first information may be information corresponding to the MVF between the first image 1310 and the second image 1320, that is, information indicating a motion amount of the object corresponding to a time point. In detail, the first information may be information indicating a motion amount of a surface of the object corresponding to time. Each time may be a certain time included in a one-cycle time period corresponding to the one-cycle angular section. Since the one-cycle time is the time taken for the X-ray generator 106 included in the gantry 730 to rotate for one cycle, the rotation angle of the gantry 730 may be used instead of the time in the first information. Also, the gantry 730 may include at least one X-ray generator 106 as described above. In detail, the gantry 730 may include a single source or a dual source.

Also, when a motion amount of the second image 1320 acquired in the second angular section 1362 is measured by using the first image 1310 acquired in the first angular section 1361, which is a start section of the one-cycle angular section 1360, as a reference image, the motion amount of the first image 1310 may be 0% motion value and the motion amount of the second image 1320 may be 100% motion value. In the following description, a value of the motion vector field that is the motion amount between the first image 1310 and the second image 1320 is expressed by a weighting value W. Also, the motion amount may be a sum of absolute values of all motion vectors in the motion vector field. Also, the motion amount may be expressed by being converted by the W.

Also, when a relationship between the time and the weighting value indicating the motion amount of the object has linearity, as illustrated in FIG. 13C, the weighting value W and the time may be displayed as a graph 1370 illustrated in a section 1390. Also, the shape of the graph 1370 corresponding to the first information may be freely defined by a user or set to be optimized considering the object. For example, when the object is a heart, the graph 1370 may have a non-linear shape according to state of heart at a time point in which an image to be reconstruct.

In detail, when the motion amount of the object and the time have a linear relationship, the data acquirer 710 may respectively match a zero MVF and the MVF that indicates a motion amount between the first and second images 1310 and 1320, with a first weighting value and a second weighting value. In detail, the zero MVF may correspond to a start point of the one-cycle angular section and the MVF indicating a motion amount between the first and second images 1310 and 1320 may correspond to an end point of the one-cycle angular section. Referring to FIG. 13C, in the graph 1370 indicating the first information 1380, the weighting value 0 indicating the zero MVF is matched with a start point of 0° of the one-cycle angular section 1360 or a time of t=0, and the weighting value 1 indicating the MVF expressing the motion amount between the first image 1310 and the second image 1320 is matched with an angular point of 180°+a that is an end point of the one-cycle angular section 1360 or a time of t=end. Also, a case in which the time and the weighting value have a linear relationship with each other is described as an example.

A first time t1 corresponds to the first image and a second time t2 corresponds to the second image. For example, if the raw data to reconstruct the first image is acquired in a section from 0 to 0.03 seconds of 0.2 seconds corresponding to the one-cycle angular section 1360, then the first time may be a time point of 0.015 seconds that is a middle time point of the section of 0 to 0.03 seconds. In other words, when a predetermined image is reconstructed by using the raw data acquired in a predetermined time section, a time point corresponding to a predetermined image may be a middle time point of a predetermined time section. Also, the first image 1310 corresponding to the first time t1 may correspond to a view when the X-ray generator 106 faces the object while at a position corresponding to the first time t1. Also, the second image 1320 corresponding to the second time t2 may correspond to a view when the X-ray generator 106 faces the object while at a position corresponding to the second time t2.

Also, in the first information, when the weighting value is between 0 to 1, the minimum weighting value "0" may correspond to the motion amount at a position or time when the size of the object decreases the most in the one-cycle angular section 1360, and the maximum weighting value "1" may correspond to the motion amount at a position or time when the size of the object is the largest in the one-cycle angular section 1360.

Also, in the first information, the relationship between the motion amount and the time may be determined according to a relationship that is modeled by a quadratic equation or a relationship that is modeled by statistical information.

For example, a motion pattern of the object may be statistically modeled. In detail, when the object is a heart, motion of the heart is statistically modeled and the shape of the graph 1370 in the section 1390 in the first information may be set to correspond to the modeled motion of the heart.

Also, in the first information, the shape of a graph indicating a motion pattern of the object may vary according to the object. For example, when the object is the entire heart, the shape of a graph in the first information may reflect the motion pattern of the entire heart. Also, when the object is a coronary artery that is included in the heart, the shape of the graph of the first information may reflect the motion pattern of the coronary artery. Also, even when the object is the coronary artery included in the heart, the motion pattern may vary according to the position of the coronary artery in the heart and thus the shape of the graph of the first information may be set to be different according to the position of the coronary artery. Also, when the object is a mitral valve (MV) that is included in the heart, the shape of the graph of the first information may reflect the motion pattern of the MV.

Also, the motion pattern may vary according to a partial area of the object to be tomography scanned. In this case, the first information may be acquired for each partial area to reflect a different motion pattern for each partial area. A target image indicating the entire object may be reconstructed by performing motion correction for each partial area by using the first information that is acquired and is different for each partial area. For example, when the object is a heart, the motion pattern may vary in each of the left ventricle, the right ventricle, the left atrium, and the right atrium. In this case, the first information may be individually acquired in each of the left ventricle, the right ventricle, the left atrium, and the right atrium, motion correction is performed on a partial image of each of the left ventricle, the right ventricle, the left atrium, and the right atrium, and the motion-corrected partial images are synthesized to reconstruct the target image indicating the heart.

Also, in the first information, the relationship between the motion amount and the time may be set by a user. For example, a user may set the shape of the graph 1370 in the section 1390 through the user interface 750. The setting of the first information through the user interface 750 is described below in detail with reference to FIG. 28.

Also, in order for the first information 1380 to more accurately reflect a change in the motion between the first image 1310 and the second image 1320, in the acquisition of the first information 1380, a change in the motion of the object in an angular section between the first angular section 1361 and the second angular section 1362 may be estimated by using the raw data acquired in the entire one-cycle angular section 1360.

For example, the data acquirer 710 compares estimated projection data acquired by forward projecting the target image reconstructed by using the first information 1380 at a target time with measured projection data acquired through a tomography scan at the target time. To reduce an error between the estimated projection data and the measured projection data, the data acquirer 710 may correct the first information 1380. As described above, the data acquirer 710 may repeatedly correct the first information 1380 so that the first information 1380 may accurately reflect the motion of the object.

The image reconstructor 720 reconstructs the target image corresponding to the target time based on the first information.

Figure 14:
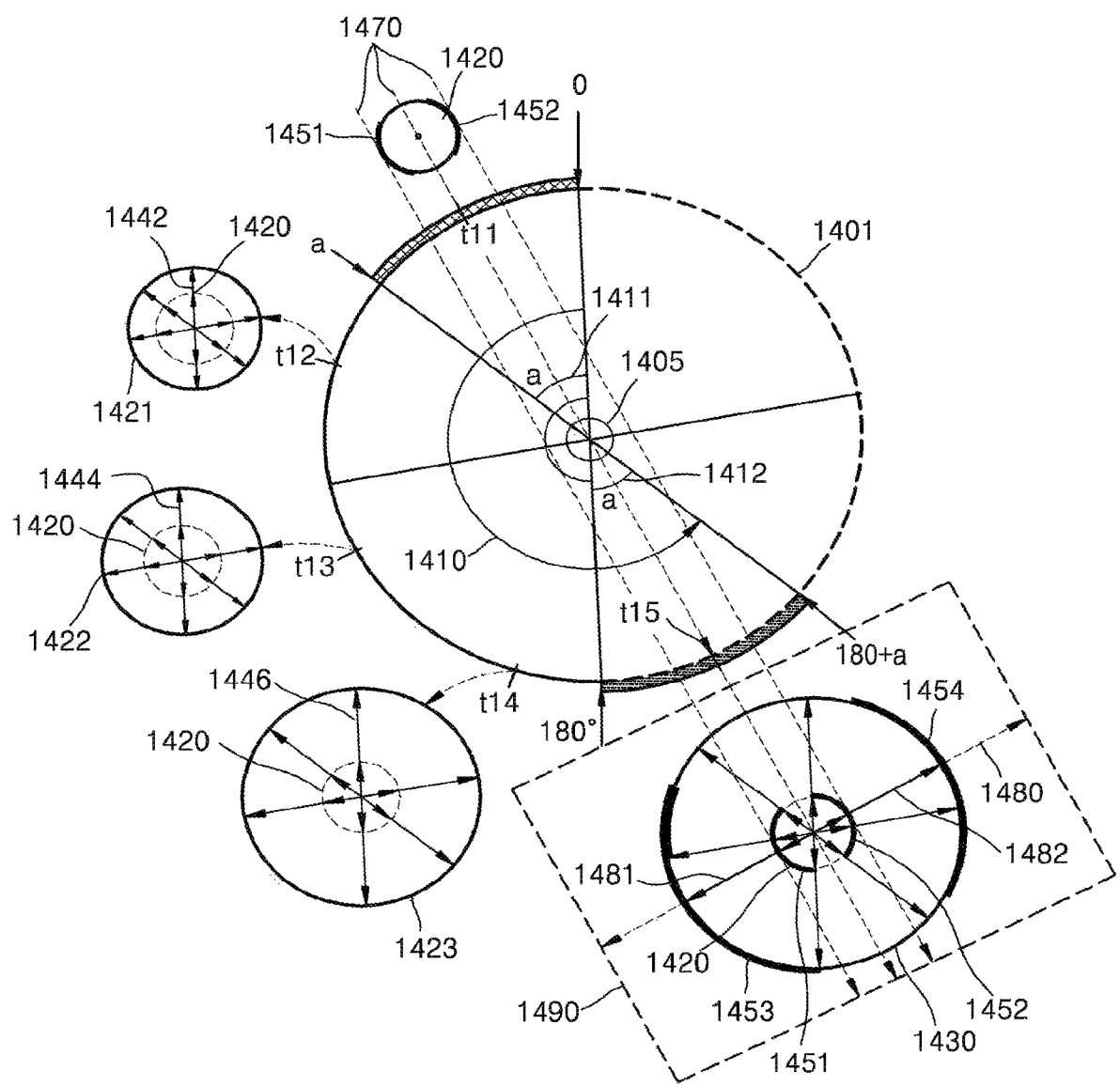
FIG. 14 is a view for describing the motion of an object.

FIG. 14 is a view for describing the motion of the object. Although the X-ray generator 106 projects X-rays in the form of a cone beam as illustrated in FIG. 4 described above, an example in which the cone beam is rebinned to be converted to a parallel beam for use is described in FIG. 14. Accordingly, a case in which the beam projected in a first angular section 1411 and a second angular section 1412 is illustrated as a parallel beam and the one-cycle angular section is an angle of 180°+a is described as an example.

Referring to FIG. 14, when the X-ray generator 106 performs a tomography scan while rotating around an object 1405, the X-ray generator 106 travels along a circular trajectory 1041 and projects X-rays toward the object 1405. In detail, the X-ray generator 106 performs a tomography scan while rotating around the object 1405 according to the half reconstruction method. The first angular section 1411 and the second angular section 1412 of FIG. 14 identically correspond to the first angular section 1361 and the second angular section 1362 of FIG. 13, respectively. Also, the object 1405 of FIG. 14 may identically correspond to the object, for example, the objects 1311 and 1321, illustrated in FIG. 13A.

When an object included in the first image acquired in the first angular section 1411 that corresponds to a first time t11 and an object included in the second image acquired in the second angular section 1412 that corresponds to a second time t15 are compared with each other, a motion amount of the object and the first information is thereby acquired, and a change in the size of the object in the one-cycle angular section 1410 can be predicted by using the first information.

For example, the object 1405 at the first time t11 corresponding to the first angular section 1411 has a first size 1420. As the size of the object 1405 gradually increases according to the lapse of time, the object 1405 may have a second size 1430 at the second time t15 corresponding to the second angular section 1412.

When the X-ray generator 106 projects X-rays toward the object 1405 while rotating during the first angular section 1411, the X-rays are projected in an X-ray projection direction 1470 and thus a surface, for example, surfaces 1451, 1452, 1453, and 1454, of the object 1405 existing in directions parallel to the X-ray projection direction 1470 are clearly sampled and imaged.

Accordingly, in the first image, the surfaces 1451 and 1452 of the object 1405 having the first size 1420 are illustrated, and in the second image, the surfaces 1453 and 1454 of the object 1405 having the second size 1430 are illustrated.

The data acquirer 710 acquires the first information by comparing the first image and the second image. Referring to a portion 1490 of FIG. 14, the first information indicating motion of the object 1405 may be acquired by comparing the surfaces 1451 and 1452 of the object 1405 having the first size 1420 and the surfaces 1453 and 1454 of the object 1405 having the second size.

In detail, the first information indicates motion of the object according to time and includes information indicating motions in all directions at an edge or on a surface of a component parallel to a projection direction of x-rays projected toward the object 1405 in the first angular section 1411 or the second angular section 1412. In detail, the surfaces 1451, 1452, 1453, and 1454 that are clearly imaged in the first image and the second image are surfaces that are arranged in directions parallel to the X-ray projection direction 1470 of the X-rays projected at the first time and the second time, or in the first angular section 1411 and the second angular section 1412. Accordingly, the first information may include information about motions in all directions of the surfaces 1451, 1452, 1453, and 1454 clearly imaged in the first and second images.

Also, the first information may indicate motion of the object 1405 in a first direction 1480 perpendicular to the X-ray projection directions 1470 so that the motion of the object 1405 may be more clearly compared to motion of the object 1405 in a direction other than the first direction 1480. In detail, the surface 1453 in the second image is a part of the object 1405 corresponding to the surface 1451 in the first image. It may be seen that the surface 1451 is moved by a first value 1481 in the first direction 1480 so as to have a positional change similar to the surface 1453. Also, the surface 1454 in the second image is a part of the object 1405 corresponding to the surface 1452 in the first image. It may be seen that the surface 1452 is moved by a second value 1482 in the first direction 1480 so as to have a positional change similar to the surface 1454.

Also, although in FIG. 14 the X-ray projection direction 1470 in the first angular section 1411 and the second angular section 1412 is illustrated in one direction, since the X-ray generator 106 projects X-rays toward the object 1405 at a plurality of positions while rotating in the first angular section 1411, the X-ray projection direction 1470 in the first section may be at least one of X-ray projection directions from 0° to a°. Accordingly, the first direction 1480 perpendicular to the X-ray projection direction 1470 in the first angular section 1411 and the second angular section 1412 may be within a predetermined range corresponding to the X-ray projection direction 1470 in the first angular section 1411 and the second angular section 1412.

In FIG. 14, the direction in which X-rays are projected toward the object 1405 when the X-ray generator 106 is located at the center of the first angular section 1411 or the second angular section 1412 is illustrated, as an example, as the X-ray projection direction 1470 in the first angular section 1411 or the second angular section 1412. The first direction 1480 is illustrated with an example in which the first direction 1480 is perpendicular to the direction 1470.

For example, when the weighting value and the time corresponding to the motion amount of the object in the first information are in a linear relationship as illustrated in FIG. 13C, the size of the object 1405 may increase linearly.

Accordingly, as illustrated in FIG. 14, it may be expected that the size of the object 1405 at a third position t12 is changed by a first change amount 1442 to be larger than the first size 1420. Accordingly, it may be expected that the size of the object 1405 at the third time t12 may have the third size 1421.

Also, it may be expected that the size of the object 1405 at a fourth time t13 is changed by a second change amount 1444 to be larger than the first size 1420. Accordingly, it may be expected that the size of the object 1405 at the fourth time t13 may have the size of a fourth size 1422. It may be expected that the size of the object 1405 at a fifth time t14 is changed by a third change amount 1446 to be larger than the first size 1420. Accordingly, it may be expected that the size of the object 1405 at the fifth time t14 may have the size of a fifth size 1423.

Also, the size of the object 1405 at the third time t12, the fourth time t13, and the fifth time t14 may be estimated by contracting the object 1405 having the second size 1430 based on the first information.

In detail, the size, shape, and/or position of the object 1405 at a target time may be estimated by using the first information. In an example of motion of the object illustrated in FIG. 14, the image reconstructor 720 may estimate an amount of a change in the size of the object 1405 at the target time by using the first information and may generate the target image by warping the object 1405 based on an estimated size change amount. In detail, the warping of an object signifies motion correction of the object. That is, a state, for example, at least one of the size, shape, and position, of the object at the target time is estimated by using the first information and thus a target image is reconstructed by correcting the motion of the object according to the estimated state.

Figure 15:
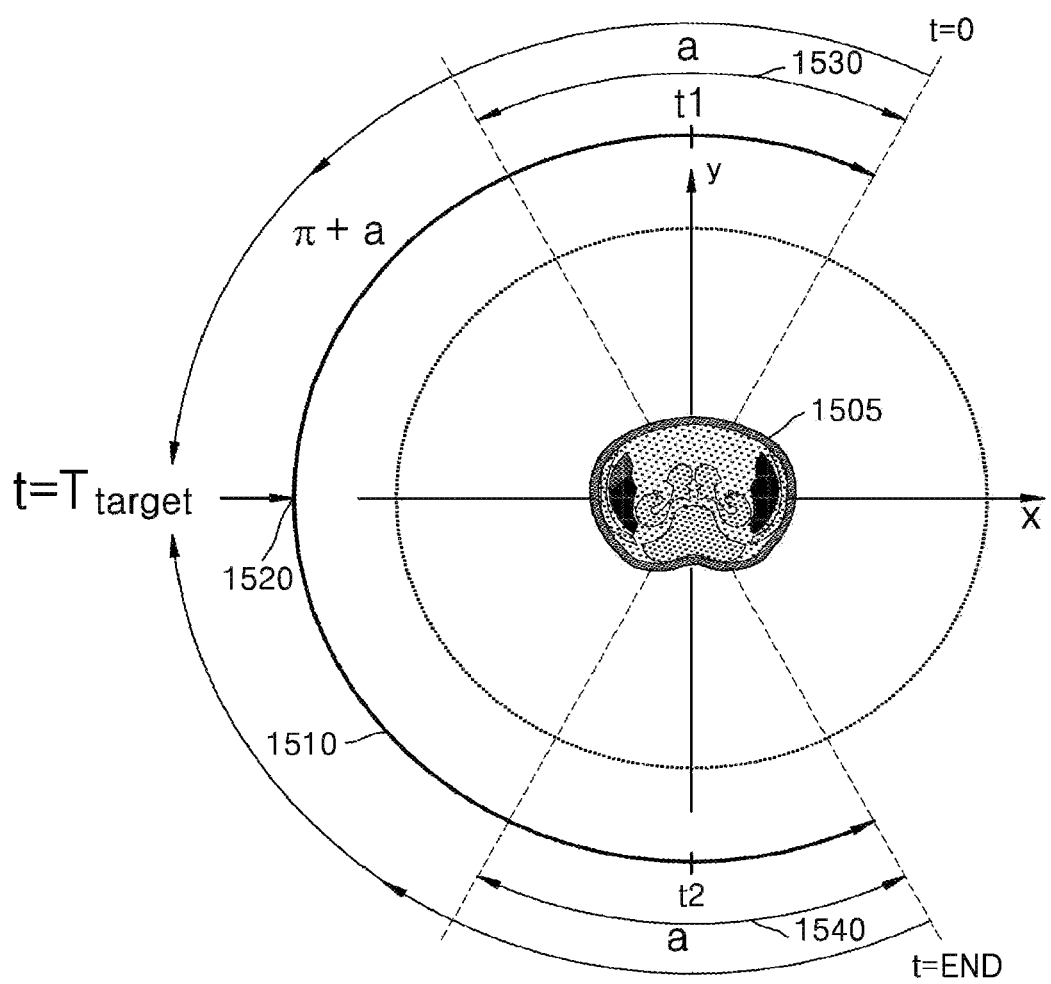
FIG. 15 is a view for describing an operation of reconstructing a target image.

FIG. 15 is a view for describing an operation of reconstructing a target image.

When the first information is acquired, the image reconstructor 720 reconstructs a target image indicating the object at the target time based on the first information. In detail, the image reconstructor 720 may estimate a motion amount of the object at the target time based on the first information and may reconstruct the target image based on the estimated amount of motion.

In detail, the image reconstructor 720 may reconstruct the target image by using the first information and at least one of a plurality of partial angular images including the first image and the second image.

In detail, the image reconstructor 720 may reconstruct the target image by warping the partial images indicating parts of the object, based on the first information.

The partial angular image used for reconstructing the target image may be an image that is reconstructed by using pieces of projection data acquired in the partial angular section such as the first and second images. Also, the partial angular image may be an image that is generated by performing filtered back-projection on a plurality of pieces of projection data corresponding to a plurality of sequentially adjoining views, or an image that is generated by performing filtered back-projection on a piece of projection data corresponding to a single view.

For example, the image reconstructor 720 may reconstruct the target image at a target time Ttarget by warping an object 1505 based on the first information. In detail, since the size of the object 1505 at the target time Ttarget may be accurately estimated by using the first information, the image reconstructor 720 warps a reconstructed tomography image to fit to an estimated object size by using the projection data acquired during a one-cycle angular section 1510, thereby reconstructing the target image.

Also, the image reconstructor 720 may reconstruct the target image by warping the first image acquired in a first angular section 1530, the second image acquired in a second angular section 1540, and at least one partial image according to the size of the object 1505 at the target time Ttarget (t=Ttarget). Surfaces of the object 1505 that are not displayed in at least one of the first image and the second image may be acquired by warping at least one of the partial angular images reconstructed corresponding to pieces of projection data acquired in at least one of the angular sections, except for the first angular section 1530 and the second angular section 1540, of the one-cycle angular section 1510.

In the following description, an operation of reconstructing a target image by using the first information 1380 described in FIG. 13C is described in detail.

Also, in FIG. 15, an abdomen of a patient is exemplarily illustrated as the object and a case of reconstructing a plurality of axial planes is illustrated.

In detail, the image reconstructor 720 may reconstruct the target image by using a plurality of pieces of projection data corresponding to a plurality of views that are raw data acquired as the X-ray generator 106 performs a tomography scan while rotating. In detail, the image reconstructor 720 may acquire the target image by performing motion correction based on the first information on an image acquired by performing filtered back-projection on the projection data corresponding to the views.

In detail, in order to reconstruct the target image at the target time Ttarget corresponding to a predetermined angular point 1520 in the one-cycle angular section 1510, a weighting value is used which corresponds to the target time Ttarget and is acquired from the first information 1380.

For example, referring to FIG. 13C, a target weighting value W1 corresponding to the target time Ttarget is acquired from the first information. A plurality of filtered back-projected images acquired by performing filtered back-projection on each of the pieces of projection data corresponding to each of the views acquired in the one-cycle angular section 1510 have a motion amount corresponding to a weighting value at each view (or viewpoint). Accordingly, to allow each filtered back-projected image to have a motion state of the object at the target time, a motion amount corresponding to a difference between the target weighting value W1 and a weighting value with respect to a view (or viewpoint) corresponding to each filtered back-projected image is applied to each filtered back-projected image for warping. The target image may be reconstructed by using a plurality of warped filtered back-projected images. In detail, in the process of performing filtered back-projection on the projection data acquired in the one-cycle angular section 1510, a pixel that is filtered by back-projection is warped by using the first information, and the target image is reconstructed thereby.

Alternatively, the image reconstructor 720 may acquire an image by performing filtered back-projection on the pieces of projection data acquired in the one-cycle angular section 1510 and then warp the acquired image by using the first information, thereby performing reconstruction of a target image.

In detail, the image reconstructor 720 reconstructs an initial image by performing filtered back-projection on a plurality of pieces of projection data that are raw data acquired through a tomography scan with a rotation of less than one turn. Motion of the object 1505 at the target time Ttarget is estimated based on the first information and may warp the initial image based on the estimated motion, thereby reconstructing the target image.

Also, the image reconstructor 720 may warp an image grid formed of a plurality of pixels to image the object 1505 based on the first information and may reconstruct the target image by using a warped image grid. The image reconstructor 720 may perform filtered back-projection on the projection data acquired through a tomography scan with a rotation of less than one turn, by using the warped image grid, and may reconstruct the target image. The reconstruction of the target image using image grid warping is described below in detail with reference to FIGS. 23A and 23B.

Also, the image reconstructor 720 may warp the center of a voxel indicating the object 1505 based on the first information and may reconstruct the target image by using the warped voxel. The reconstruction of the target image using voxel warping is described below in detail with reference to FIGS. 24A and 24B.

Also, the target time Ttarget may be set to be a time between the first time t1 and the second time t2. In detail, the target time Ttarget may be set to be a middle time between the first time t1 and the second time t2, which is described below in detail with reference to FIGS. 16 to 18.

Also, the reconstruction of the target image using warping is described below in detail with reference to FIGS. 20 to 24.

Figure 16A:
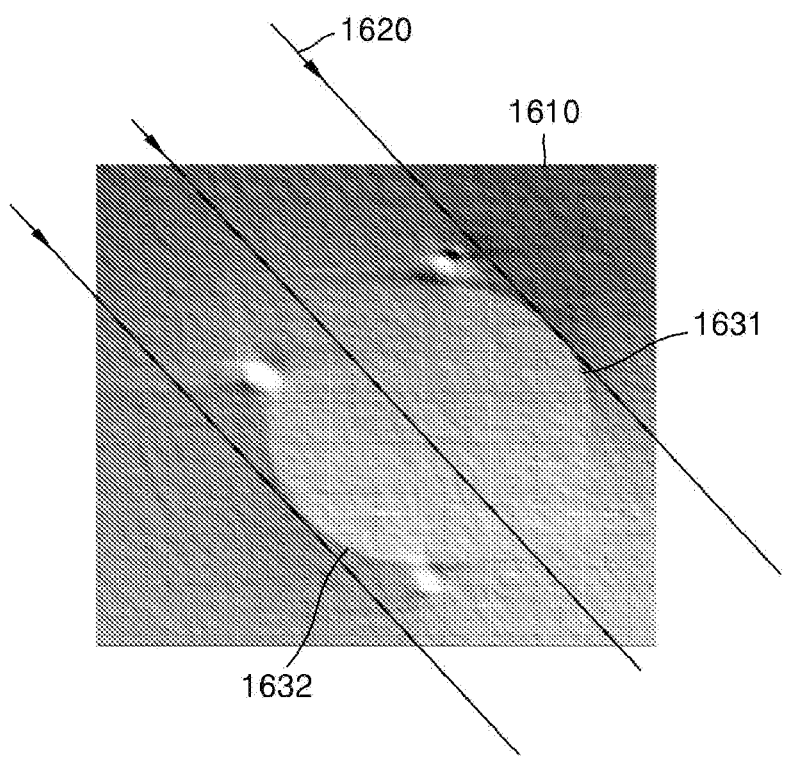
FIGS. 16A and 16B are views for describing setting of a target time.
Figure 16B:
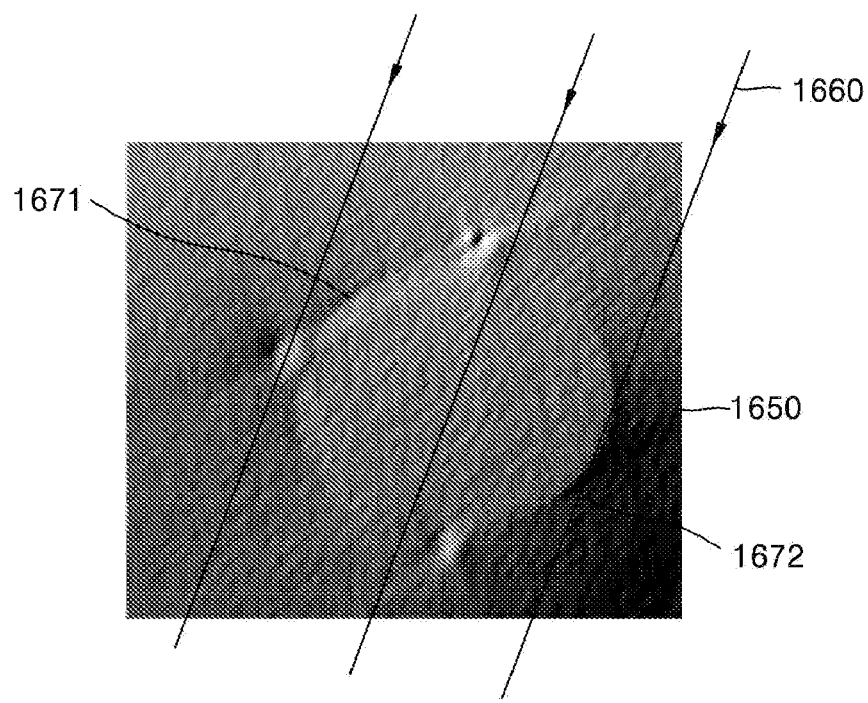

FIGS. 16A and 16B are views for describing setting of a target time.

Referring to FIG. 16, in the PAR method, a clearly imaged part of a reconstructed image appears to differ according to a view angle at which X-rays are projected. In detail, regarding surface areas of an object imaged in a reconstructed image, a surface area that is sampled relatively more and a surface area that is sampled relatively less exist according to a view angle.

In detail, referring to FIG. 16A, when X-rays are projected toward the object approximately in an 5 O'clock direction 1620, a reconstructed image 1610 is illustrated by using the raw data generated by the detected X-rays. Surfaces 1631 and 1632 that extend in a direction parallel to the 5 O'clock direction 1620 as illustrated in FIG. 16A clearly appear in the reconstructed image 1610, whereas a surface that extends in a direction perpendicular to the 5 O'clock direction 1620 does not clearly appear.

Referring to FIG. 16B, when X-rays are projected toward the object approximately in a 7 O'clock direction 1660, a reconstructed image 1650 is illustrated by using the raw data generated by the detected X-rays. Surfaces 1671 and 1672 that extend in a direction parallel to the 7 O'clock direction 1660 as illustrated in FIG. 16B clearly appear in the reconstructed image 1650, whereas a surface that extends in a direction perpendicular to the 7 O'clock direction 1660 does not clearly appear.

In other words, the surface portion that is clearly imaged differs according to an X-ray beam direction. In detail, the surface portion that extends in a direction similar to the X-ray beam direction may be clearly imaged rather than a surface portion of other area.

Accordingly, as described above, when the target time Ttarget is set to be a middle time between the first time t1 and the second time t2, the target image corresponding to the target time Ttarget may be more accurately reconstructed. In detail, when the target time Ttarget is set to be a middle time between the first time t1 and the second time t2, a portion of a surface of the object that is not clearly imaged by the projection data acquired at the target time Ttarget is imaged by warping a portion of a surface of the image that is clearly imaged by the projection data acquired at at least one of the first time t1 and the second time t2, and thus the object at the target time Ttarget may be more clearly imaged.

Figure 17:
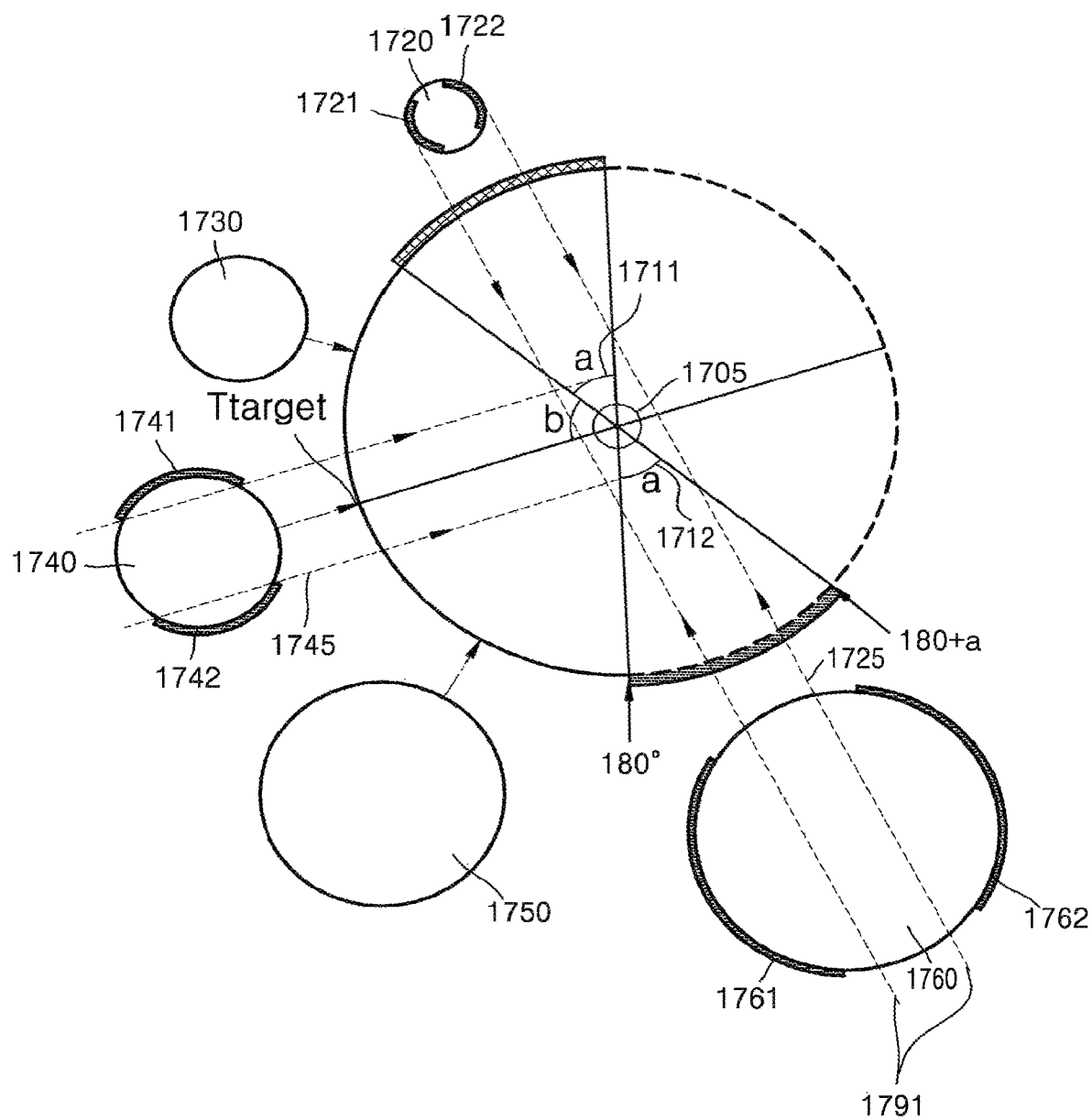
FIG. 17 is a view for describing the setting of a target time.

FIG. 17 is a view for describing the setting of a target time.

Referring to FIG. 17, as a whole, FIG. 17 identically corresponds to FIG. 14. In detail, an object 1705, a first angular section 1711, and a second angular section 1712 of FIG. 17 identically correspond to the object 1405, the first angular section 1411, and the second angular section 1412 of FIG. 14. Surfaces 1721 and 1722 of an object 1720 are clearly imaged in the first image acquired in the first angular section 1711, as illustrated in FIG. 17. Also, surfaces 1761 and 1762 of an object 1760 are clearly imaged in the second image acquired in the second angular section 1712, as illustrated in FIG. 17.

Compared to the above, surfaces 1741 and 1742 of an object 1740 in an image acquired in an angular section corresponding to the target time Ttarget are clearly imaged as illustrated in FIG. 17.

In other words, the surfaces 1741 and 1742 of the object 1740 that are clearly imaged and correspond to the target time Ttarget and the surfaces 1721 and 1722, or 1761 and 1762, of the object 1740, or the object 1760, that are clearly imaged and correspond to the first and second images are portions that do not overlap each other. Accordingly, the target time Ttarget is set to be a middle time between the first time t1 and the second time t2, and then the target image indicating the state of an object at a set target time may be reconstructed.

In detail, in imaging the object 1705, surface portions, for example, the surfaces 1722 and 1721, or 1761 and 1762, that extend in a direction similar to the direction 1791 may be imaged by warping at least one of the first and second images, and surface portions, for example, the surfaces 1741 and 1742, that extend in a direction parallel to the direction 1741 may be imaged by warping the image acquired in an angular section corresponding to the target time Ttarget. Accordingly, even the surfaces that are not clearly sampled at the target time Ttarget may be clearly imaged in a reconstructed target image.

Although in FIG. 17 a case of reconstructing a target image by warping a filtered back-projected partial angular image is described as an example, the image reconstructor 720 may reconstruct the target image by adjusting the projection data itself. In detail, each piece of projection data acquired in the one-cycle angular section may be corrected according to the state of the object at the target time Ttarget. In detail, the pieces of projection data included in the one-cycle angular section image different portions of the object according to a view. Accordingly, the image reconstructor 720 may reconstruct the target image by estimating a state of the object at the target time Ttarget by using the first information, adjusting each of a plurality of pieces of projection data corresponding to a plurality of views according to the estimated state of the object, and performing filtered back-projection on the adjusted projection data.

Figure 18A:
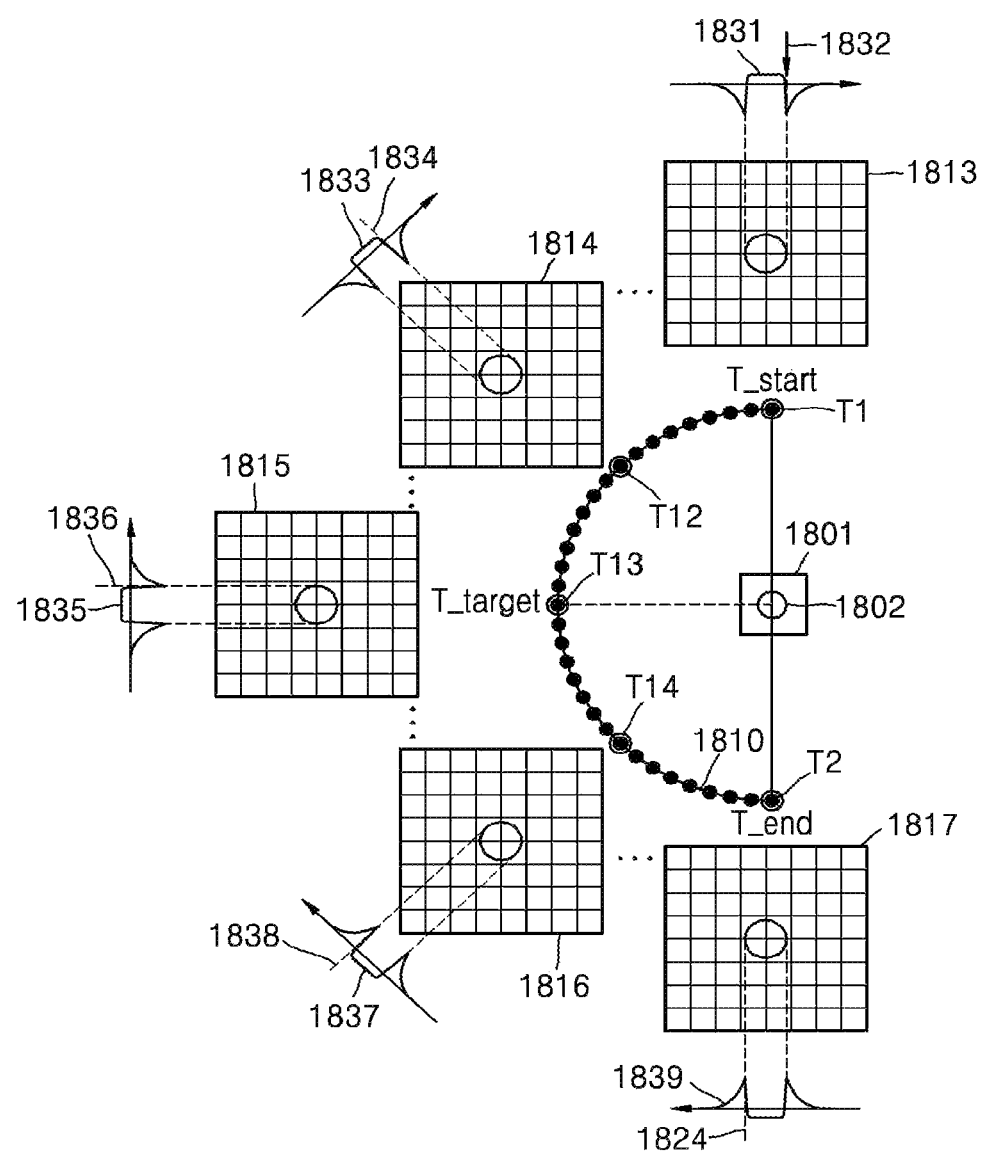
FIGS. 18A and 18B are views for describing reconstruction of a target image indicating an object that does not move.
Figure 18B:
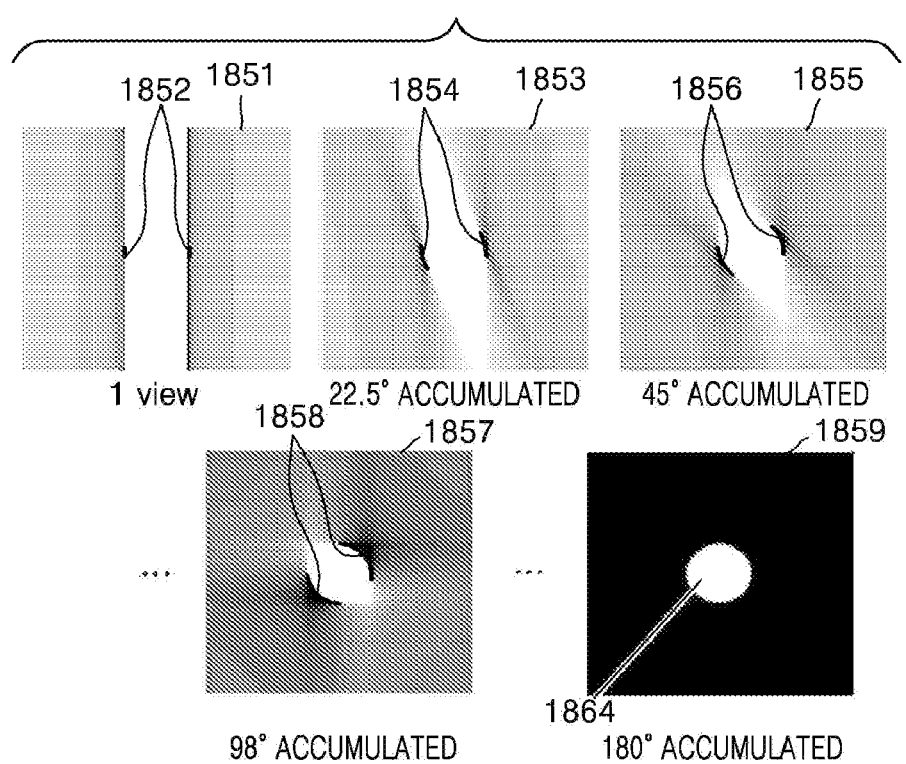

FIGS. 18A and 18B are views for describing reconstruction of a target image indicating an object that does not move. In detail, FIG. 18A illustrates that the X-ray generator 106 performs a tomography scan while rotating around an object 1801. Also, FIG. 18B illustrates an operation of performing back-projection on projection data acquired by filtering raw data acquired through a tomography scan.

In FIG. 18A, a case in which the X-ray generator 106 rotates around the object 1801 and performs a tomography scan and a tomography image is reconstructed by a filtered back-projection method is described as an example. Also, a case in which the object 1801 includes a circular target 1802 as illustrated in FIG. 18A is described as an example. Also, as described in FIG. 13, the one-cycle angular section 1360 is an angle of 180°+fan angle that is a section of projection data. In FIG. 18A, however, a case in which a tomography scan is performed while rotating 180° is described as an example, for convenience of explanation.

Referring to FIG. 18A, as the X-ray generator 106 moves along a source trajectory 1810 that is circular and projects X-rays toward an object 1805 at each of a plurality of positions having a predetermined angular interval, projection data is acquired. The projection data is filtered and thus filtered projection data is acquired. In FIG. 18A, a plurality of points located on the source trajectory 1810 indicate the positions where the X-ray generator 106 is located and projects X-rays. For example, while moving at a predetermined interval such as 0.5°, 1°, or 3°, the X-ray generator 106 may project X-rays toward the object 1805. Rotation starts at a first time T1 and stops at a second time T2. Accordingly, the first time T1 corresponds to a rotation angle 0° and the second time T2 corresponds to a rotation angle 180°.

In detail, when the X-ray generator 106 projects X-ray toward the object 1801 at the first time T1, the X-rays projected in an X-ray projection direction 1832 pass through an object 1813 and thus a signal 1831 may be acquired. A value of the signal 1831 may vary on a surface of the object 1813 due to a difference in transmissivity of the X-ray according to a material of the object 1813. In detail, the value of the signal 1831 may vary on a surface arranged in a direction parallel to the X-ray projection direction 1832.

Also, when the X-ray generator 106 projects X-rays toward the object 1801 at a third time T12, the X-rays projected in an X-ray projection direction 1834 pass through an object 1814 and thus a signal 1833 may be acquired. A value of the signal 1833 may vary on a surface arranged in a direction parallel to the X-ray projection direction 1834.

Also, when the X-ray generator 106 projects X-rays toward the object 1801 at a fourth time T13, the X-rays projected in an X-ray projection direction 1836 pass through an object 1815 and thus a signal 1835 may be acquired. A value of the signal 1835 may vary on a surface arranged in a direction parallel to the X-ray projection direction 1836.

Also, when the X-ray generator 106 projects X-rays toward the object 1801 at a fifth time T14, the X-rays projected in an X-ray projection direction 1838 pass through an object 1816 and thus a signal 1837 may be acquired. A value of the signal 1837 may vary on a surface arranged in a direction parallel to the X-ray projection direction 1838.

Also, when the X-ray generator 106 projects X-rays toward the object 1801 at the second time T2, the X-rays projected in an X-ray projection direction 1824 pass through an object 1817 and thus a signal 1839 may be acquired. A value of the signal 1839 may vary on a surface arranged in a direction parallel to the X-ray projection direction 1824.

Also, since the signal 1831 includes information about a surface that is arranged in the X-ray projection direction 1832, an image 1851 acquired by performing filtered back-projection on the signal 1831 contributes to imaging of the surface arranged in the X-ray projection direction 1832. Also, since the signal 1833 includes information about a surface that is arranged in the X-ray projection direction 1834, the filtered projection data corresponding to the signal 1833 contributes to imaging of the surface arranged in the X-ray projection direction 1834. In other words, the projection data acquired at each view contributes to imaging of a surface of the object corresponding to each view. This may be explained by using a Fourier slice theorem that shows a relationship between a frequency component of an image and a value of the projection data acquired by projection a parallel beam toward the object 1801. The "view" corresponds to a direction, position, and/or rotation angle when the X-ray generator 106 projects X-rays toward the object.

Also, the DAS 116 of FIG. 4 may acquire a signal, for example, the signal 1831. The image processing unit may process the signal 1831 and generate filtered projection data. The filtered projection data is back-projected, thereby acquiring the image 1851.

In detail, when the X-ray generator 106 rotates and projects X-rays at a plurality of positions or views and thus a plurality of pieces of filtered projection data are acquired, the pieces of filtered projection data are accumulated and back-projected, thereby reconstructing a tomography image. In other words, an image representing the object may be acquired through a back-projection process in which the filtered projection data is reflected to image pixels.

Referring to FIG. 18B, a surface of the circular target 1802 included in the object 1801 at the first time T1 appears in the back-projected image 1851 corresponding to the first time T1. The pieces of filtered projection data are accumulated and back-projected with respect to the respective views acquired as the X-ray generator 106 rotates counterclockwise.

For example, a back-projected image 1853 is acquired by accumulating and back-projecting the pieces of filtered projection data acquired in an angular section having an angle of 22.5°. A partial surface 1854 of the circular target 1802 in the object 1801 appears in the back-projected image 1853.

Next, a back-projected image 1855 is acquired by accumulating and back-projecting the pieces of filtered projection data acquired in an angular section having an angle of 45°. A partial surface 1856 of the circular target 1802 in the object 1801 appears in the back-projected image 1855.

Next, a back-projected image 1857 is acquired by accumulating and back-projecting the pieces of filtered projection data acquired in an angular section having an angle of 98°. A partial surface 1858 of the circular target 1802 in the object 1801 appears in the back-projected image 1857.

Next, a back-projected image 1859 is acquired by accumulating and back-projecting the pieces of filtered projection data acquired in an angular section having an angle of 180°. An entire surface 1864 of the circular target 1802 in the object 1801 appears in the back-projected image 1859.

For an object that does not move, a state, for example, at least one of the size, position, and shape, of the object 1801 is unchanged when referring to each of the first time T1, the third time T12, the fourth time T13, the fifth time T14, and the second time T2, which are a plurality of times included in the one-cycle angular section.

Accordingly, in the reconstruction of a tomography image by accumulating the pieces of filtered back-projected data of the pieces of projection data corresponding to the views included in the one-cycle angular section, since the state of the object 1801 is unchanged at each of the views, no blurring due to motion artifacts is generated in the back-projected image 1859 that is finally reconstructed.

Figure 18C:
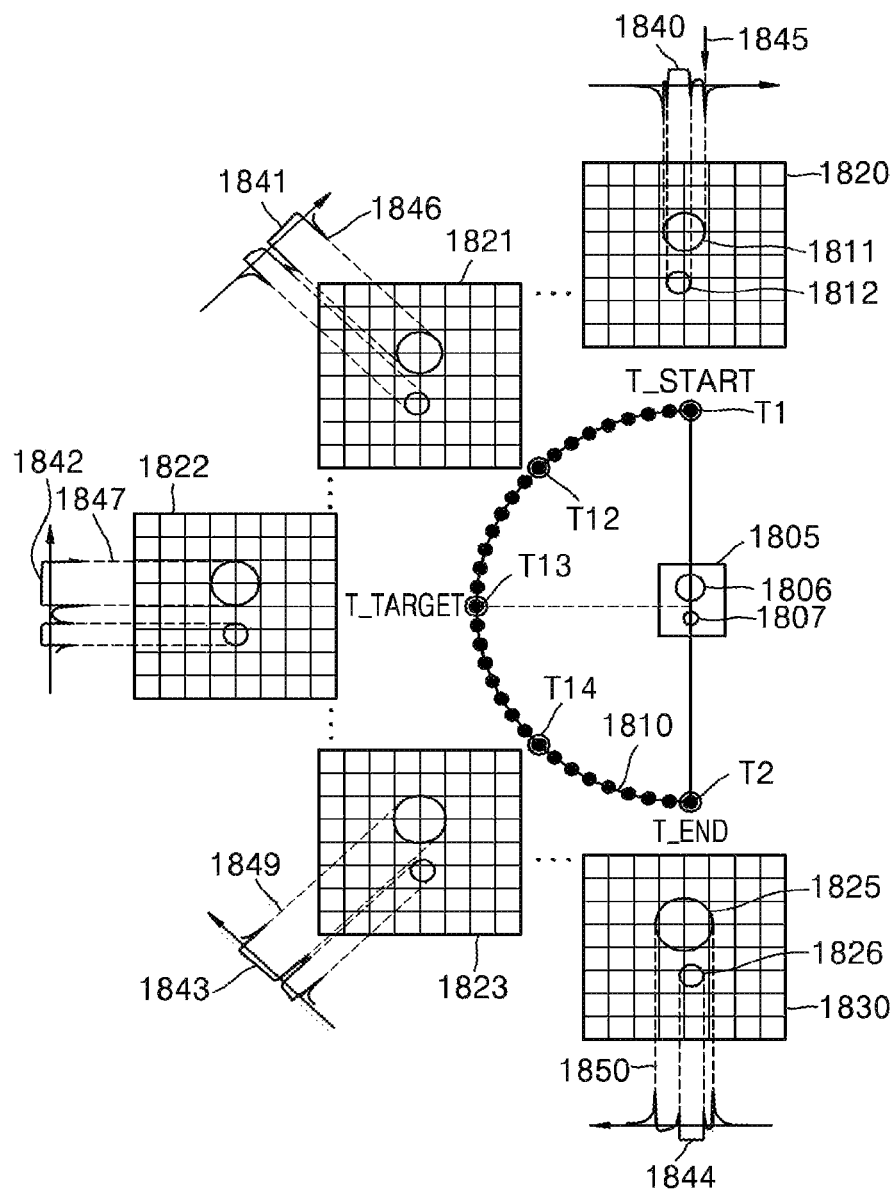
FIGS. 18C and 18D are views for describing motion artifacts that may be generated during reconstruction of a target image indicating an object that moves.
Figure 18D:
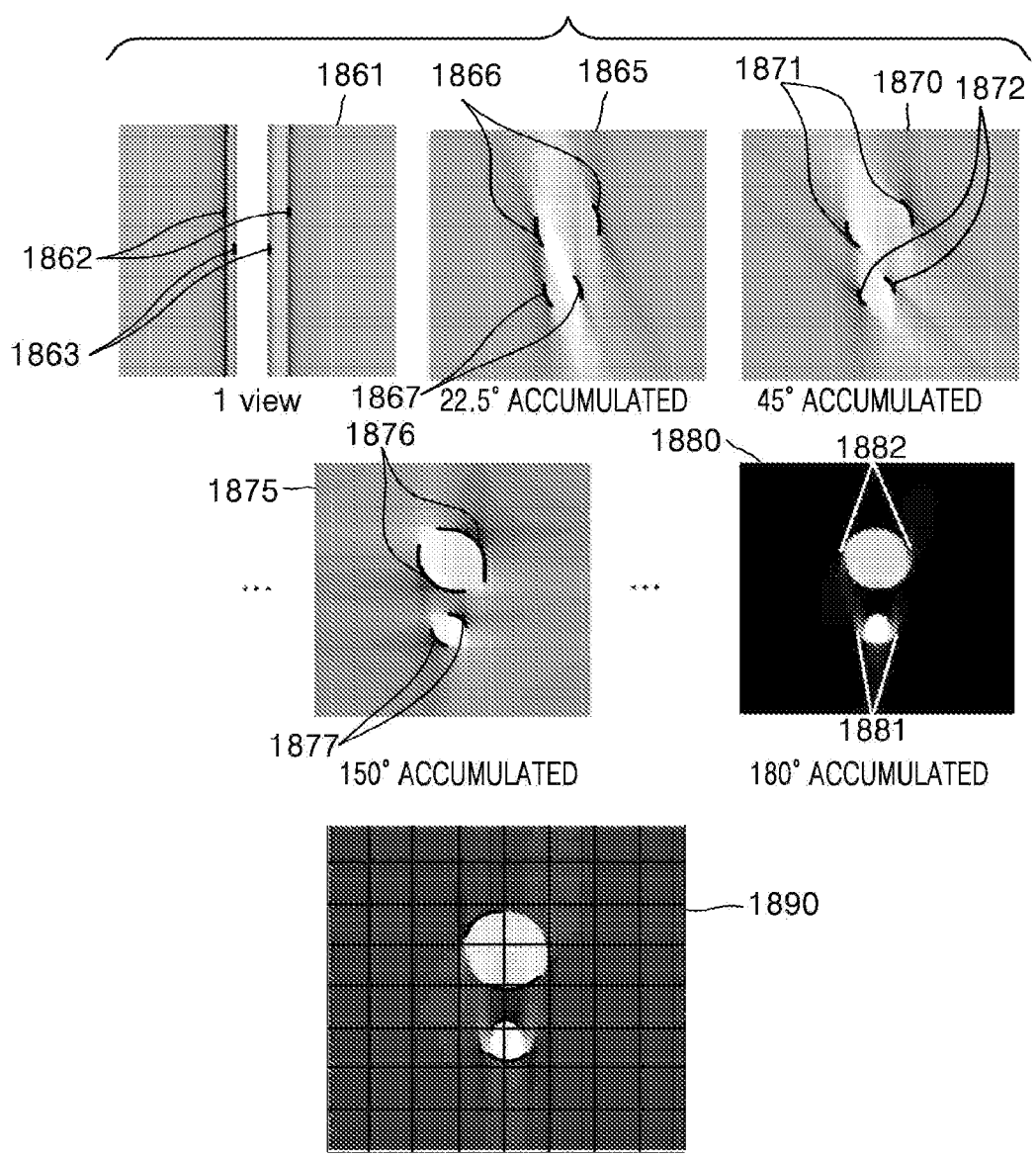

FIGS. 18C and 18D are views for describing motion artifacts that may be generated during the reconstruction of a target image indicating an object that moves. In detail, 18C illustrates that the X-ray generator 106 performs a tomography scan while rotating around the object 1805. Also, 18D illustrates an operation of performing back-projection on projection data acquired by filtering raw data acquired through a tomography scan. In 18D, a case of reconstructing a tomography image by the filtered back-projection method is described as an example. Also, a case in which the object 1805 includes two circular targets 1806 and 1807 as illustrated in 18C is described as an example. In the following description, for convenience of explanation, an upper circular target of the object 1805 is referred to as a first target 1806 and a lower circular target of the object 1805 is referred to as a second target 1807. Also, as illustrated in FIG. 13, the one-cycle angular section 1360 is an angle of 180+fan angle. However, in 18C, for convenience of explanation, a case of rotating by 180° and performing a tomography scan is described as an example.

Referring to 18C, the X-ray generator 106 moves along the source trajectory 1810 that is circular and projects X-rays toward the object at each of a plurality of positions having a predetermined angular interval, thereby acquiring projection data. Then, the projection data is filtered and thus filtered projection data is acquired. In 18C, a plurality of points located on the source trajectory 1810 indicate the positions where the X-ray generator 106 is located to project X-rays. For example, the X-ray generator 106 may move at a predetermined interval such as 0.5°, 1°, or 3° and may project X-rays toward the object 1805. The X-ray generator 106 rotates starting from the first time T1 to the second time T2. Accordingly, the first time T1 corresponds to a rotation angle of 0°, and the second time T2 corresponds to a rotation angle of 180°.

The object 1805 may move like an object 1820, an object 1821, an object 1822, an object 1823, and object 1830, respectively, at the first time T1, the third time T12, the fourth time T13, the fifth time T14, and the second time T2. In detail, the size of the first target 1806 included in the object 1805 expands without changing its position, whereas the second target 1807 does not expand but may move from the left to the right.

In detail, when the X-ray generator 106 projects X-rays toward the object 1805 at the first time T1, the X-rays projected in an X-ray projection direction 1845 pass through an object 1820 and thus a signal 1840 may be acquired. A value of the signal 1840 may vary on a surface of the object 1820 due to a difference in transmissivity of the X-ray according to a material of the object 1820. In detail, the value of the signal 1840 may vary on a surface arranged in a direction parallel to the X-ray projection direction 1845.

Also, when the X-ray generator 106 projects X-rays toward the object 1805 at a third time T12, the X-rays projected in an X-ray projection direction 1846 pass through an object 1821 and thus a signal 1841 may be acquired. A value of the signal 1841 may vary on a surface arranged in a direction parallel to the X-ray projection direction 1846.

Also, when the X-ray generator 106 projects X-rays toward the object 1805 at the fourth time T13, the X-rays projected in an X-ray projection direction 1847 pass through an object 1822 and thus a signal 1842 may be acquired. A value of the signal 1842 may vary on a surface arranged in a direction parallel to the X-ray projection direction 1847.

Also, when the X-ray generator 106 projects X-rays toward the object 1805 at the fifth time T14, the X-rays projected in an X-ray projection direction 1849 pass through an object 1823 and thus a signal 1843 may be acquired. A value of the signal 1843 may vary on a surface arranged in a direction parallel to the X-ray projection direction 1849.

Also, when the X-ray generator 106 projects X-rays toward the object 1805 at the second time T2, the X-rays projected in an X-ray projection direction 1850 pass through an object 1830 and thus a signal 1844 may be acquired. A value of the signal 1844 may vary on a surface arranged in a direction parallel to the X-ray projection direction 1850.

Also, since the signal 1840 includes information about a surface that is arranged in the X-ray projection direction 1845, an image 1861 acquired by performing filtered back-projection on the signal 1840 contributes to imaging of the surface arranged in the X-ray projection direction 1845. Also, since the signal 1841 includes information about a surface that is arranged in the X-ray projection direction 1846, the filtered projection data corresponding to the signal 1841 contributes to imaging of the surface arranged in the X-ray projection direction 1846. In other words, the projection data acquired at each view contributes to imaging of a surface of the object corresponding to each view. The "view" corresponds to a direction, position, and/or rotation angle when the X-ray generator 106 projects X-rays toward the object.

Also, the DAS 116 of FIG. 4 may acquire a signal, for example, the signal 1840. The image processing unit may process the signal 1840 and generate filtered projection data. The filtered projection data is back-projected, thereby acquiring the image 1861.

In detail, when the X-ray generator 106 rotates and projects X-rays at a plurality of positions or views and thus a plurality of pieces of filtered projection data are acquired, the pieces of filtered projection data are accumulated and back-projected, thereby reconstructing a tomography image. In other words, an image representing the object may be acquired through a back-projection process in which the filtered projection data is reflected to image pixels.

Referring to 18D, a surface 1862 of the first target 1811 and a surface 1863 of the second target 1812 included in the object 1820 at the first time T1 appear in the back-projected image 1861 corresponding to the first time T1. The pieces of filtered projection data are accumulated and back-projected with respect to the respective views acquired as the X-ray generator 106 rotates counterclockwise.

For example, a back-projected image 1865 is acquired by accumulating and back-projecting the pieces of filtered projection data acquired in an angular section having an angle of 22.5°. A partial surface 1866 of the first target 1806 and a partial surface 1876 of the second target 1807 in the object 1805 appear in the back-projected image 1865.

Next, a back-projected image 1870 is acquired by accumulating and back-projecting the pieces of filtered projection data acquired in an angular section having an angle of 45°. A partial surface 1871 of the first target 1806 and a partial surface 1872 of the second target 1807 in the object 1805 appear in the back-projected image 1870.

Next, a back-projected image 1875 is acquired by accumulating and back-projecting the pieces of filtered projection data acquired in an angular section having an angle of 150°. A partial surface 1876 of the first target 1806 and a partial surface 1877 of the second target 1807 in the object 1805 appear in the back-projected image 1875.

Next, a back-projected image 1880 is acquired by accumulating and back-projecting the pieces of filtered projection data acquired in an angular section having an angle of 180°. Entire surfaces of the first target 1806 and the second target 1807 in the object 1805 appear in the back-projected image 1875.

In 18D, an image 1890 is a tomography image showing a finally reconstructed object through the back-projection process.

However, due to motion of the object, pieces of surface information of the pieces of filtered projection data acquired at each view do not match with one another. Accordingly, when a plurality of pieces of filtered projection data acquired in the one-cycle angular section are accumulated, as illustrated in 18D, the surface does not clearly appear and thus blurrings 1881 and 1882 are generated.

According to the present invention, even when the object includes various materials, surfaces, and/or shapes as in the object 1805 of 18C, motion of the object 1805 may be traced and the motion of the object 1805 may be accurately estimated without limiting the object to be tomography scanned. Accordingly, an image that is motion corrected according thereto may be reconstructed. The above-described image reconstruction operation using the first information is described below in detail with reference to FIGS. 19A to 24.

Figure 18E:
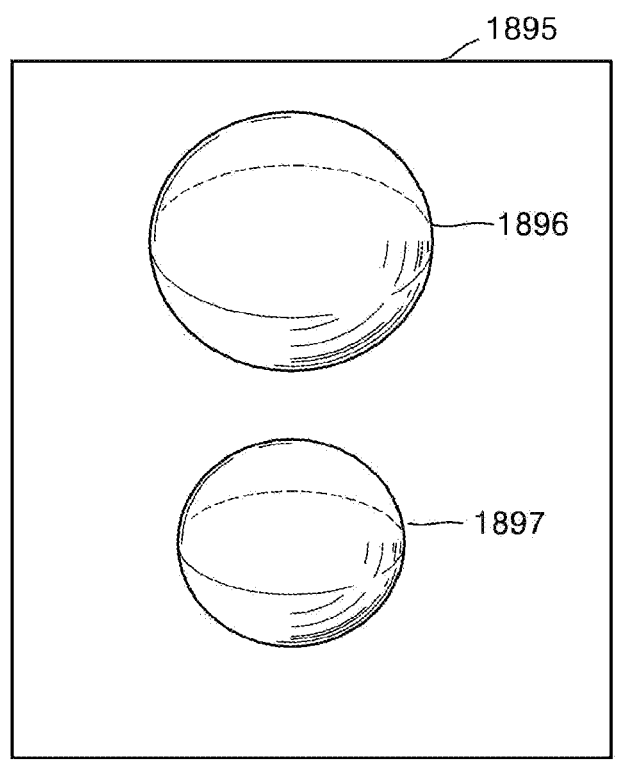
FIG. 18E is a view for describing an object presented in a 3D tomography image.

FIG. 18E is a view for describing an object presented as a 3D tomography image. Although a 2D tomography image is described as an example in the above-described drawings, a target image may be reconstructed as a 3D tomography image.

In detail, Referring to FIG. 13C, an object may be reconstructed as a 3D tomography image 1895. When the target image is reconstructed as a 3D tomography image 1895, the first image and the second image are acquired as 3D tomography images showing the object. The first image may include information about motion of the object in 3D.

Figure 19A:
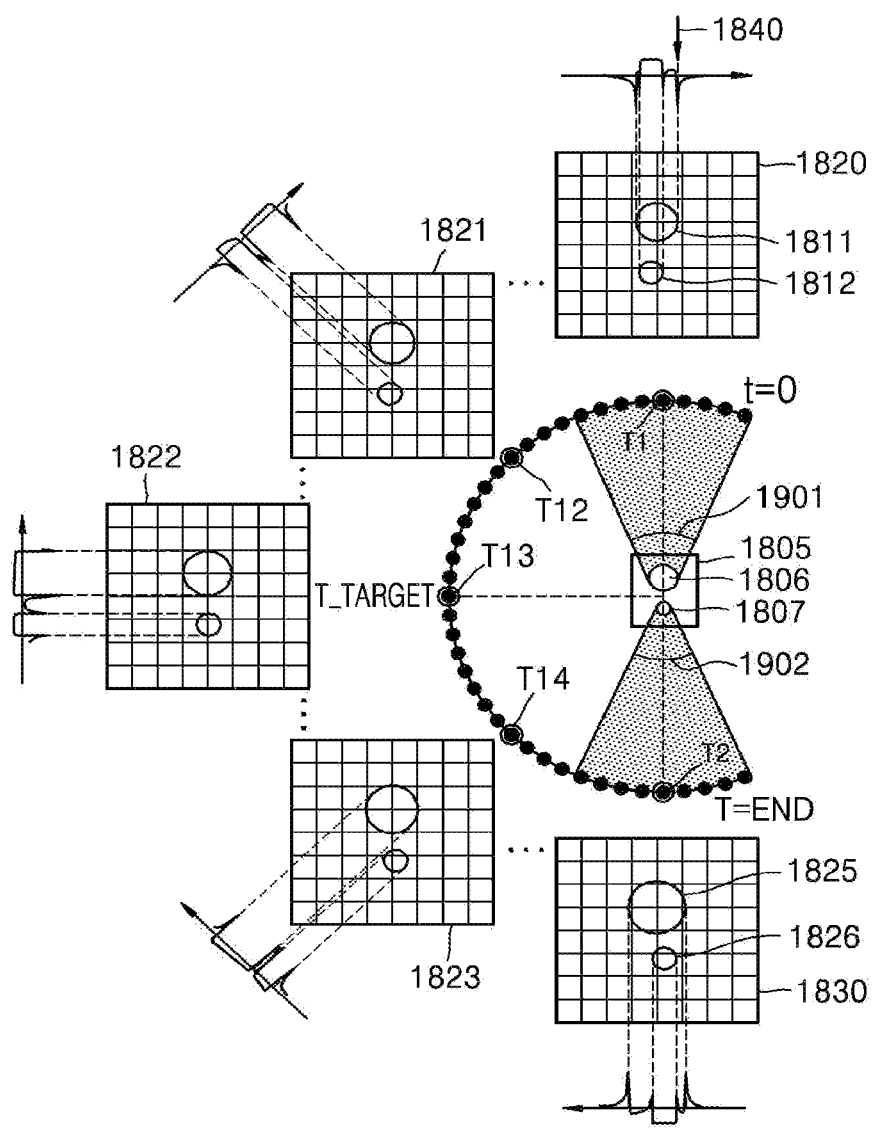
FIGS. 19A and 19B are views for describing a measurement of a motion amount of the object.
Figure 19B:
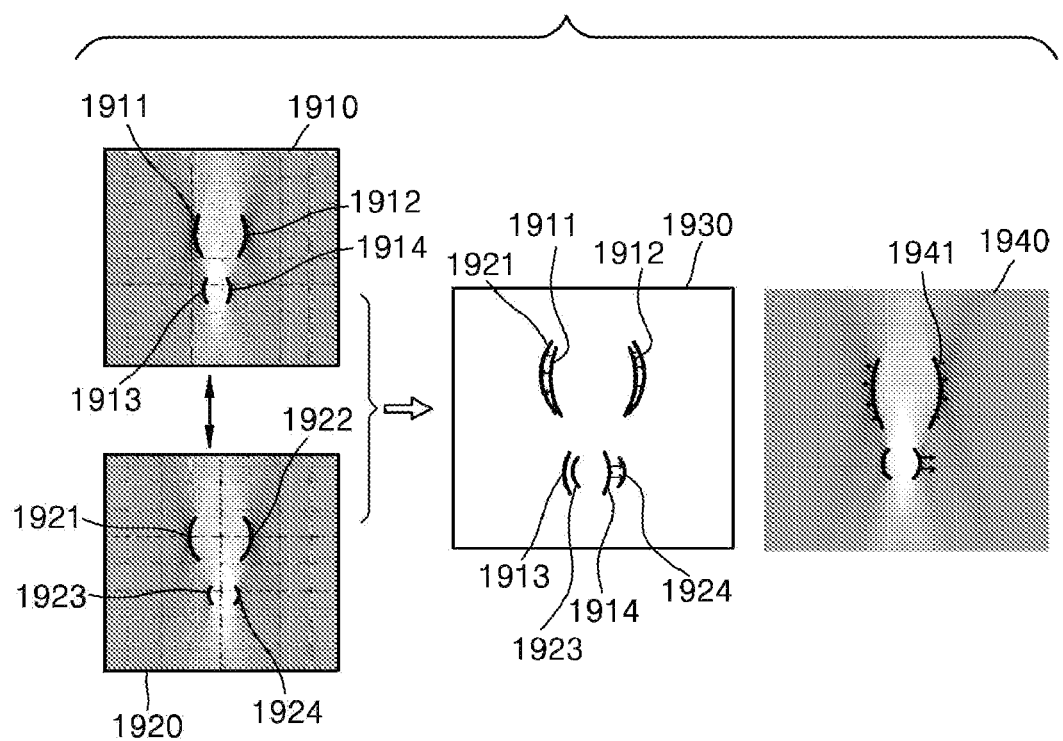

For example, as illustrated in 18C, when the object is presented in the 3D tomography image 1895 as the first target 1896 and the second target 1897, the first information may include information about motions of the first target 1896 and the second target 1897. FIGS. 19A and 19B are views for describing a measurement of a motion amount of the object. In FIGS. 19A and 19B, the first angular section 1901 and the second angular section 1902 identically correspond to the first angular section 1361 and the second angular section 1362 of FIG. 13, respectively. A first image 1910 and a second image 1920 respectively correspond to the first image 1310 and the second image 1320 of FIG. 13. MVF information 1940 is identical to the MVF information described in FIG. 13B. Accordingly, in FIGS. 19A and 19B, redundant descriptions with FIGS. 18A and 18B are omitted. Also, since the object 1805 in FIG. 19A is identical to the object 1805 of 18C, a redundant description with 18C are omitted.

Referring to FIG. 19B, the first image 1910 is acquired by using the projection data corresponding to the first angular section 1901 that are acquired while the X-ray generator 106 rotates around the object 1805. The first image 1910 shows surfaces 1911 and 1912 included in the first target 1806 and surfaces 1913 and 1914 included in the second target 1807. Also, the second image 1920 is acquired by using the projection data corresponding to the second angular section 1902 that are acquired while the X-ray generator 106 rotates around the object 1805. The second image 1920 shows surfaces 1921 and 1922 included in the first target 1806 and surfaces 1923 and 1924 (included in the second target 1807. In other words, the projection data acquired in each view of a predetermined angular section included in the one-cycle angular section contribute to imaging other different surfaces or other different areas of the object 1805.

Since surfaces of the same portions of the object 1805 are shown in the first image 1910 and the second image 1920, the data acquirer 710 compares the first image 1910 and the second image 1920 as in an image 1930 and acquires the MVF 1940 indicating motion of the object 1805. The MVF 1940 includes vectors 1941 indicating a direction of a motion and a degree (amount) of a motion of the surface of the same portion. Accordingly, the first information indicating motion of the object 1805 between the first time T1 and the second time T2 may be acquired through the MVF 1940.

Since the first image 1910 and the second image 1920 are images reconstructed by using the projection data acquired in a partial angular section, the reconstructed image may have a high temporal resolution and reduced motion artifacts according thereto. The reconstruction of a target image at a target time Ttarget using the MVF 1940 that is acquired is described below in detail with reference to FIG. 20A to 21C.

Figure 20A:
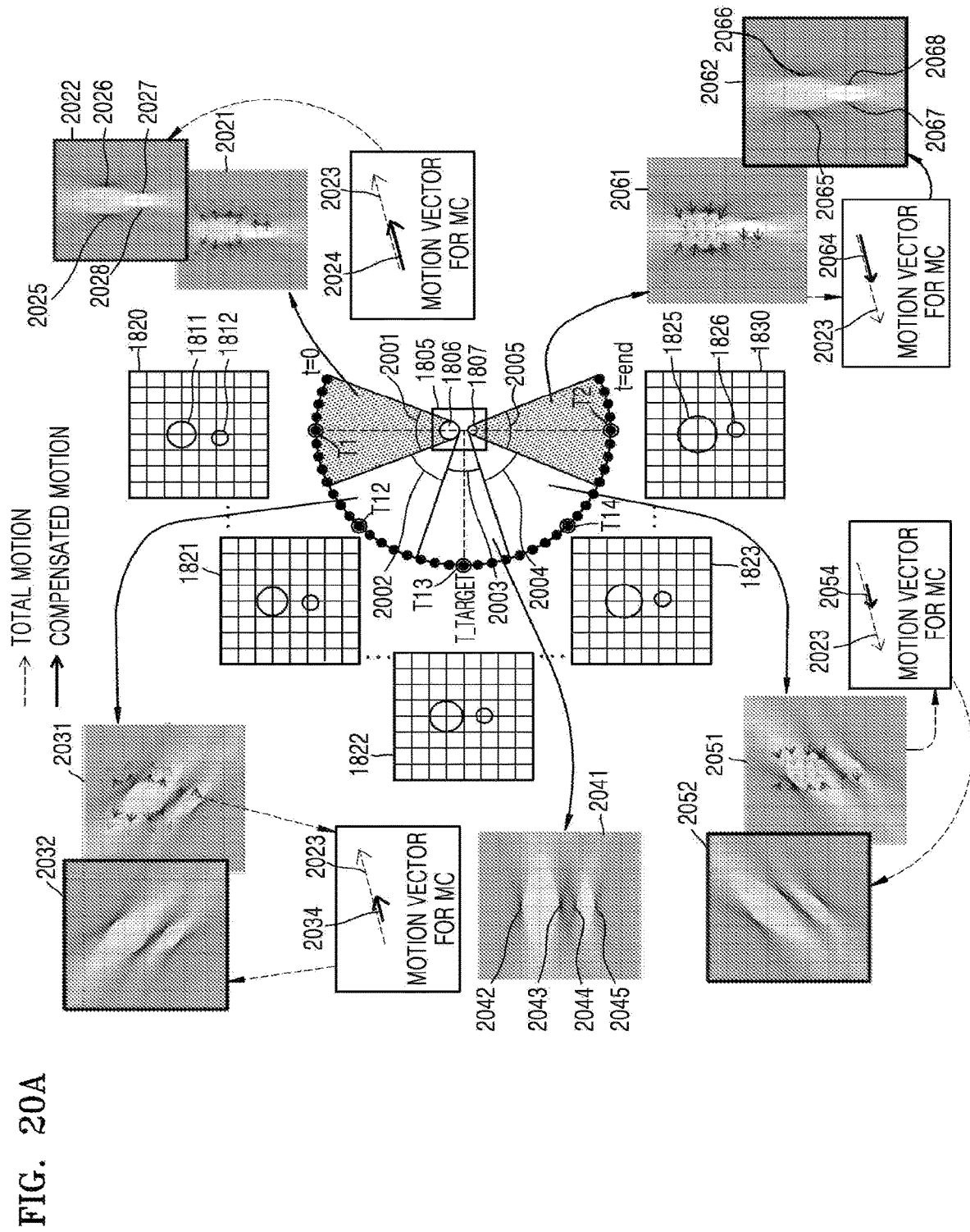
FIGS. 20A and 20B are views for describing the operation of reconstructing a target image.
Figure 20B:
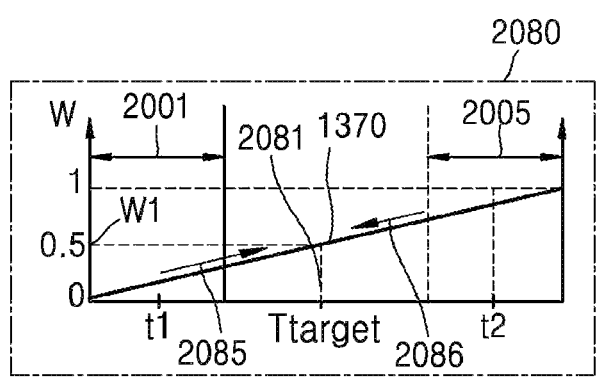

FIGS. 20A and 20B are views for describing the operation of reconstructing a target image. Redundant descriptions with FIGS. 18A and 19B are omitted.

The image reconstructor 720 reconstructs a target image at the target time Ttarget by using information indicating motion of the object 1805, for example, the MVF.

As described above, first information 2080 of FIG. 20B may be acquired by using the MVF 1940. Since the first information is the same as the first information described in FIG. 13C, a detailed description thereof is omitted. A degree of motion of the object 1805 at the target time may be estimated by using the first information 2080. Alternatively, a state including at least one of the size, shape, and position of the object 1805 at the target time Ttarget may be estimated by using the first information 2080.

As described above in FIGS. 19A and 19B, the projection data acquired in each view or a predetermined angular section included in one-cycle angular section contribute to imaging of other different surfaces or other different areas of the object 1805.

In the reconstruction of a target image, the image reconstructor 720 may perform motion correction by using the first information on a surface portion or an area of the object 1805 that is imaged by using the projection data acquired at a time other than the target time Ttarget, except for a surface portion or area of the object 1805 that is imaged by using the projection data acquired at the target time Ttarget.

In FIG. 20A, for convenience of explanation, the one-cycle angular section is divided into five angular sections 2001, 2002, 2003, 2004, and 2005, and images that are obtained by back-projecting the projection data acquired in each of the divided angular sections are illustrated. In detail, a partial image 2021 is acquired by back-projecting the projection data acquired in the first angular section 2001. A partial image 2031 is acquired by back-projecting the projection data acquired in the third angular section 2002. A partial image 2041 is acquired by back-projecting the projection data acquired in the fourth angular section 2003. A partial image 2051 is acquired by back-projecting the projection data acquired in the fifth angular section 2004. Also, a partial image 2061 is acquired by back-projecting the projection data acquired in the second angular section 2005.

In FIG. 20A, the first angular section 2001, the second angular section 2005, the partial image 2021, and the partial image 2061 identically correspond to the first angular section 1901, the second angular section 1902, the first image 1910, and the second image 1920 of FIGS. 19A and 19B, respectively.

Referring to FIG. 20A, a case in which the target time Ttarget is set to be a middle between the first time T1 and the second time T2 is described as an example. As described in FIG. 17, when the projection data acquired in an angular section adjacent to the target time Ttarget are back-projected, only surfaces 2042, 2043, 2044 or 2045 arranged in a horizontal direction are imaged in the partial image 2041. Surfaces that are not imaged in the partial image 2041 are imaged by using the projection data acquired in an angular section other than the fourth angular section 2003 including the target time Ttarget in the one-cycle angular section.

In the imaging of the surface that is not imaged in the partial image 2041, the image reconstructor 720 may perform motion correction by using the first information in order to reduce blurring.

In detail, surfaces or partial areas shown in the partial image 2021 acquired in the first angular section 2001 are corrected according to the MVF. In other words, referring to the first information 2080, it is assumed that an amount W of a motion in the first angular section 2001 is 0 and an amount W1 of motion of the object 1805 at a target time Ttarget 2081 is 0.5 (W1=0.5). Then, the surface of the object 1805 at the target time Ttarget 2081 may be accurately acquired by warping the object 1805 included in the partial image 2021 corresponding to the first angular section 2001 by a motion amount W of 0.5) (W=0.5). Accordingly, a corrected partial image 2022 is generated by performing motion correction on the partial image 2021, based on a motion amount 2024 which is generated from a start time (t=0) to the target time Ttarget and compared to a total motion amount 2023. The total motion amount 2024 may correspond to maximum motion amount W of 1 (W=0) in the first information 2080, and the motion amount 2024 may correspond to a difference between the motion amount W1 at the target time Ttarget 2081 and the motion amount W at a time of 0 (t=0) corresponding to the first angular section 2001.

Motion correction is performed on the other angular sections in the same manner as in the first angular section. In detail, the corrected partial image 2032 that is corrected by performing motion correction on the partial image 2031 that is obtained by back-projecting the projection data acquired in the third angular section 2002, based on a motion amount 2034 generated from the third time T12 to the target time Ttarget 2081 compared to the total motion amount 2023.

Also, a corrected partial image 2062 is generated by performing motion correction on the partial image 2061 that is obtained by back-projecting the projection data acquired in the second angular section 2005, based on the motion amount 2064 generated from an end time (t=end) to the target time Ttarget 2081 compared to the total motion amount 2023. Also, a corrected partial image 2052 is generated by performing motion correction on the partial image 2051 that is obtained by back-projecting the projection data acquired in the fifth angular section 2004, based on a motion amount 2054 generated from the fifth time T14 to the target time Ttarget 2081 compared to the total motion amount 2023.

The motion correction using the projection data acquired at a time prior to the target time Ttarget 2081 and the motion correction using the projection data acquired at a time after the target time Ttarget 2081 may be performed in opposite directions. In detail, referring to the first information 2080, the motion correction prior to the target time Ttarget 2081 is performed in a direction 2085 in which the motion amount W increases and the motion correction after the target time Ttarget 2081 is performed in a direction 2086 in which the motion amount W decreases. Accordingly, the directions of the total motion amount 2023 at the first time T1 and the total motion amount 2023 at the second time T2 are illustrated to be opposite to each other.

Also, the first information includes information about motions of the imaged surfaces in the partial image 2021 and the partial image 2061. Accordingly, the image reconstructor 720 may perform motion correction by warping a surface or a partial area of the object 1805 in the first direction that is perpendicular to a direction in which X-rays are projected in the first angular section 2001 and the second angular section 2005.

A target image corresponding to the target time Ttarget may be reconstructed by using the corrected partial images 2022, 2032, 2052, and 2062 and the partial image 2041 acquired in the fourth angular section 2003 including the target time Ttarget. Since the corrected partial images 2022, 2032, 2052, and 2062 accurately reflect a motion state of the object 1805 at the target time Ttarget, generation of motion artifacts may be reduced in the target image reconstructed by performing motion correction using the above-described first information.

When an image is reconstructed by tomography scanning a moving object without performing motion correction, blurring may be severely generated in a surface portion due to the projection data acquired at a time that is far from the target time Ttarget. In detail, surfaces extending in the horizontal direction are imaged in the partial image 2041 acquired in the fourth angular section 2003 including the target time Ttarget 2081, and surfaces extending in a vertical direction that are not imaged in the partial image 2041 are imaged in the partial image 2021 and the partial image 2061 respectively corresponding to the first time T1 and the second time T2 that are located farthest from the target time Ttarget 2081. As described above, due to the motion of the object 1805, the surfaces imaged in partial image 2021 acquired in the first angular section 2001 that is a start angular section and the partial image 2061 acquired in the second angular section 2005 that is an end angular section are considerably different in their positions and sizes. In other words, blurring is most severely generated in an image reconstructed by using the projection data acquired in the start angular section and the projection data acquired in the end angular section. Accordingly, the surfaces extending in the vertical direction in the target image Ttarget 2081 are blurred due to the surfaces having different positions and sizes and imaged in the partial image 2021 and the partial image 2061. In detail, when the middle time between the first time T1 and the second time T2 is set to be the target time Ttarget, as illustrated in 18C, blurring 1881 and 1882 are most severely generated in the surfaces extending in the vertical direction in the back-projected image 1880 that is the target image as in 18D.

In an embodiment of the present invention, the image reconstructor 720 may generate a target image 2070 by performing motion correction on the partial images acquired in the one-cycle angular section by using the first information and thus motion artifacts may be reduced.

Also, when the target time Ttarget 2081 is set in the middle of the first time T1 and the second time T2 that are the start time and the end time of the one-cycle angular section, motion correction may be effectively performed on the surfaces 1881 and 1882 where blurring is most severely generated in the image reconstructed corresponding to the target time Ttarget 2081, and thus motion artifacts in the reconstructed imaged may be reduced. Accordingly, the target time Ttarget may be set at the middle time of the one-cycle angular section and motion correction is performed by using the first information, and thus the target image having an optimized image quality is thereby constructed.

In detail, since the first information is acquired by using the partial image 2021 and the partial image 2061 that are generated by using the projection data acquired in each of the first angular section 2001 and the second angular section 2005, the first information most accurately includes information about motions of, for example, surface components 2025, 2026, 2027, and 2028, and 2065, 2066, 2067, and 2068, respectively included in the partial image 2021 and the partial image 2061. Accordingly, motion correction may be accurately performed on the surface components 2025, 2026, 2027, and 2028, and 2065, 2066, 2067, and 2068, which are vertically arranged with respect to the object 1805, by performing motion correction based on the first information. However, in the first information, information about motions of surface components included in, for example, the partial image 2031, 2041, or 2051, generated based on the projection data acquired in a view included in a section other than the first angular section 2001 and the second angular section 2005, may be less accurate than the information about motions of the surface components 2025, 2026, 2027, and 2028, and 2065, 2066, 2067, and 2068, respectively included in the partial image 2021 and the partial image 2061.

In detail, the motions of the surfaces found in the first angular section 2001 and the second angular section 2005 that, respectively, are the start section and the end section of the one-cycle angular section have the lowest correlation with a motion of a surface found in an angular section, for example, the fourth angular section 2003 that is orthogonal to the first angular section 2001 and the second angular section 2005. Accordingly, among the information about a motion of a surface of the object according to the first information, an error may appear to be the largest in information about a motion of a surface component included in an image, for example, the partial image 2041, that is generated by using the projection data acquired in an angular section, for example, the fourth angular section 2003 that is orthogonal to the first angular section 2001 and the second angular section 2005.

In setting the target time, when the fourth time T13 that is orthogonal to the first angular section 2001 and the second angular section 2005 and also is a middle time between the first angular section 2001 and the second angular section 2005 is set to be the target time, there is no need to perform motion correction on a surface component, for example, the surface components 2042, 2043, 2044, and 2045, imaged by using the projection data acquired in the fourth angular section 2003 that is orthogonal to the first angular section 2001 and the second angular section 2005. Accordingly, the influence of an error that may occur in the motion correction of the object may be reduced by removing an error that may occur in performing the motion correction on the surface component, for example, the surface components 2042, 2043, 2044, and 2045, imaged in an angular section that is orthogonal to the first angular section 2001 and the second angular section 2005. Accordingly, when the position of the target time Ttarget is located at the middle position between the first angular section 2001 and the second angular section 2005, the quality of a reconstructed target image may be improved.

Also, although FIG. 20A illustrates a case in which the one-cycle angular section is divided into a plurality of angular sections and motion correction is performed for each of back-projected images corresponding to the angular sections, as an example. Also, the motion correction may be performed on a partial image obtained by back-projecting the projection data acquired in each view included in the one-cycle angular section. Alternatively, the motion correction may be performed in a process of back-projecting the projection data acquired in each view. Also, the motion correction may be performed on a partial image obtained by back-projecting the projection data acquired in a view group including several views. Alternatively, the motion correction may be performed in a process of back-projecting the projection data acquired in the view group.

Also, although FIG. 20A illustrates a case of performing motion correction on the partial images, motion correction may be performed on projection data corresponding to each view and the target image may be reconstructed by performing filtered back-projection on the corrected projection data corresponding to each view.

Figure 20C:
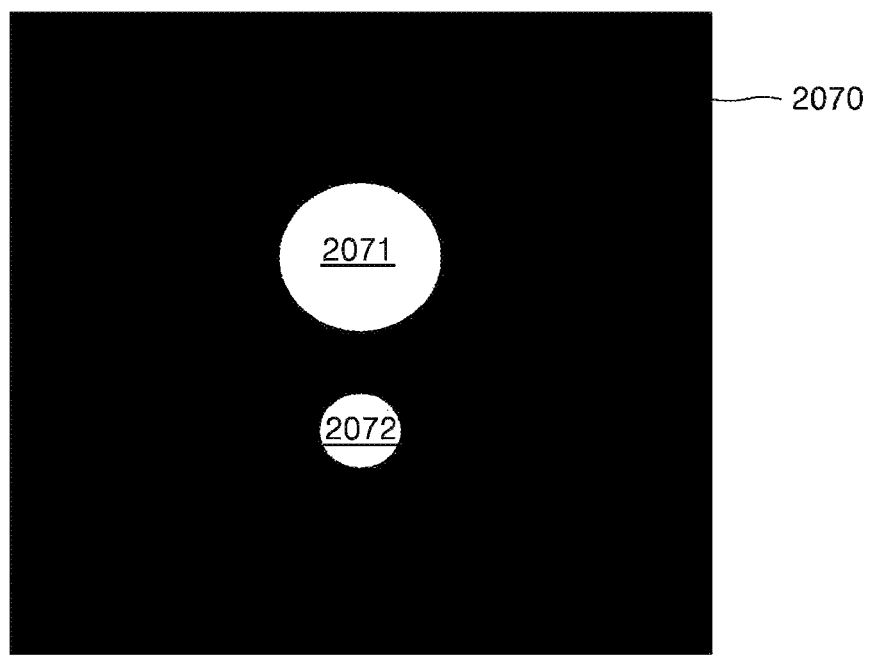
FIG. 20C is a reconstructed target image.

FIG. 20C is a reconstructed target image. Referring to FIG. 20C, an object includes two circular targets 2071 and 2072. The circular targets 2071 and 2072 respectively corresponded to a first target 1806 and a second target 1807 included in the object 1805 illustrated in FIG. 20A. Referring to FIG. 20C, the target image 2070 reconstructed by the image reconstructor 720 according to an embodiment of the present invention shows an object when the target time Ttarget is a middle time between the first time T1 and the second time T2.

The target image 2070 has hardly any blurring due to motion artifacts and accurately reflects a state of the object at the target time Ttarget.

Figure 21A:
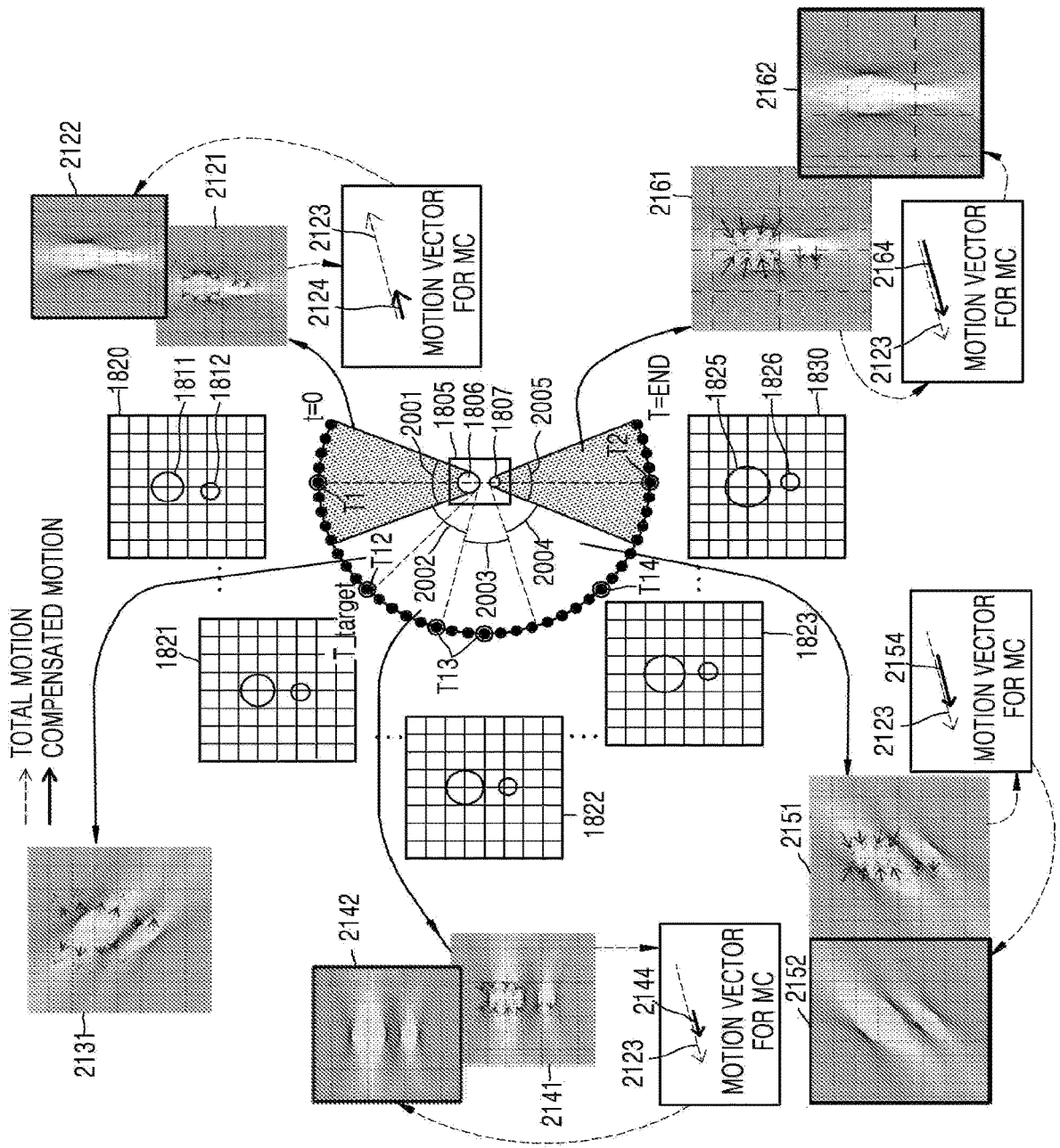
FIGS. 21A and 21B are views for describing the operation of reconstructing a target image.
Figure 21B:
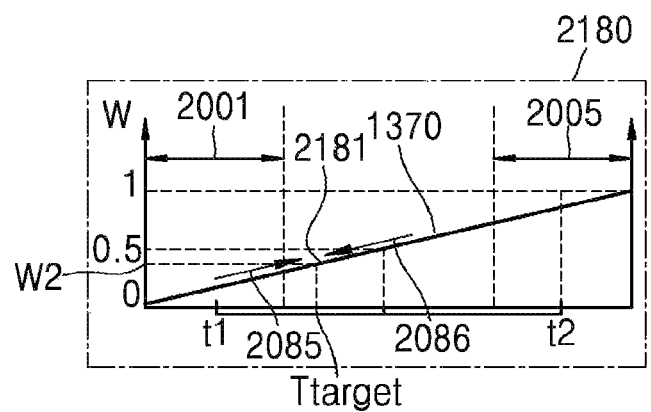

FIG. 21A is a another view for describing the operation of reconstructing a target image.

Referring to FIG. 21A, a redundant description with FIG. 20A is omitted because most parts are substantially the same as those in FIG. 20A, except that a time that is not the middle time of the one-cycle angular section is set as the target time Ttarget.

Referring to FIG. 21A, a time, for example, the third time T12 that is not the middle time of the one-cycle angular section, is set as the target time Ttarget.

Referring to FIG. 21A, a corrected partial image 2122 is generated by performing motion correction on a partial image 2121, based on a motion amount 2124 generated from a start time (t=0) to the target time Ttarget compared to a total motion amount 2123. The total motion amount 2123 corresponds to a motion amount W that is 1 (W=1) in the first information 2180 shown in FIG. 21B. The motion amount 2124 corresponds to a difference between the motion amount W at the start time (t=0) and a motion amount W2 at the target time Ttarget 2181.

Motion correction is performed on the other angular sections in the same manner as that in the first angular section. In detail, a corrected partial image 2142 is generated by performing motion correction on a partial image 2141, based on a motion amount 2144 generated from the fourth time T13 to the target time Ttarget compared to the total motion amount 2123.

Also, a corrected partial image 2152 is generated by performing motion correction on a partial image 2151, based on a motion amount 2154 generated from the fifth time T14 to the target time Ttarget compared to the total motion amount 2123. Also, a corrected partial image 2162 is generated by performing motion correction on a partial image 2161, based on a motion amount 2164 generated from the end time (t=end) to the target time Ttarget compared to the total motion amount 2123.

A target image corresponding to the target time Ttarget may be reconstructed by using the corrected partial images 2122, 2142, 2152, and 2162, and the partial image 2131 acquired in the third angular section 2002 including the target time Ttarget.

Figure 21C:
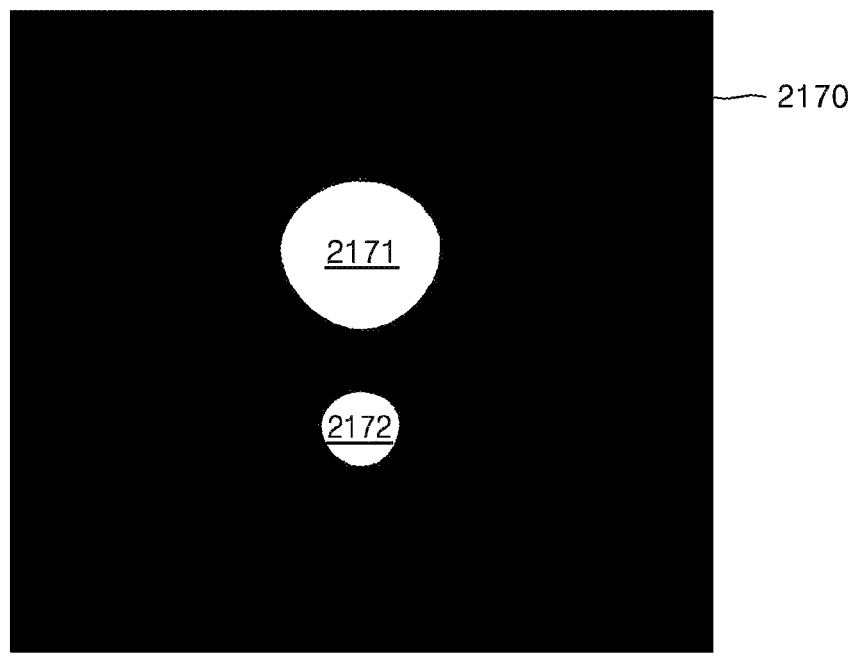
FIG. 21C is a reconstructed target image.

FIG. 21C is a reconstructed target image.

Referring to FIG. 21C, a target image 2170 reconstructed by the image reconstructor 720 according to an embodiment of the present invention shows the object when the target time Ttarget is not a middle time between the first time T1 and the second time T2 as illustrated in FIG. 21A.

The target image 2170 has hardly any blurring due to motion artifacts.

However, the quality of the target image 2170 reconstructed when the target time Ttarget is not a middle time between the first time T1 and the second time T2 may be lower than the quality of the target image 2070 reconstructed when the target time Ttarget is a middle time between the first time T1 and the second time T2. For example, when the target image 2170 and the image 2070 are compared with each other, it may be seen that the shapes of a first target 2171 and a second target 2172 included in the object are partially deformed. In detail, in the target image 2170, the shape of a lower surface of the first target 2171 appears to be slightly distorted.

In other words, in the target image, a degree of motion correction of the object included in the target image may vary according to the target time Ttarget. In detail, as the target time Ttarget is closer to the middle time between the first time T1 and the second time T2, motion correction is performed better and thus the target image may become an image that better reflects the state of the object at the target time Ttarget. In contrast, when the target time Ttarget is not the middle time between the first time T1 and the second time T2, motion correction is poorly performed and thus the target image may not accurately reflect the state of the object at the target time Ttarget compared to a case in which the target time Ttarget is the middle time between the first time T1 and the second time T2.

Accordingly, in the reconstructed target image, motion correction of the object may be performed better when the target time Ttarget corresponds to the middle time between the first time T1 and the second time T2, compared to a case in which target time Ttarget does not correspond to the middle time between the first time T1 and the second time T2.

In terms of the image quality, the quality of a reconstructed image may vary according to the position or view in the one-cycle angular section to which the target time Target is set. The "image quality" may vary according to how clearly the image shows the state of the object at a particular time. For example, the image quality may correspond to a degree of deformation of the object. Also, for example, it may be said that an image that accurately reflects the state of the object at the particular time has a superior image quality. In contrast, it may be said that an image that does not accurately reflect the state of the object at the particular time such that at least one of the position, shape, and size of the object is different from those of the object at the particular time has poor image quality. In detail, as illustrated in FIGS. 20C and 21C, the quality of a reconstructed image is optimal when the target time is the middle time between the first time T1 and the second time T2.

Figure 22A:
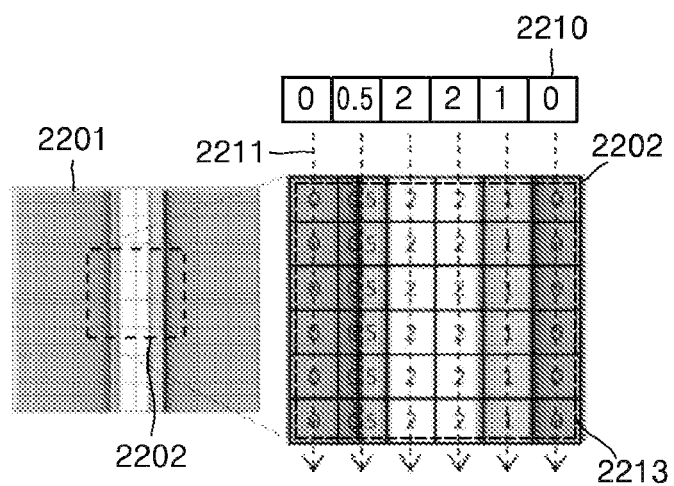
FIGS. 22A and 22B are views for describing a warping operation used to reconstruct a target image.
Figure 22B:
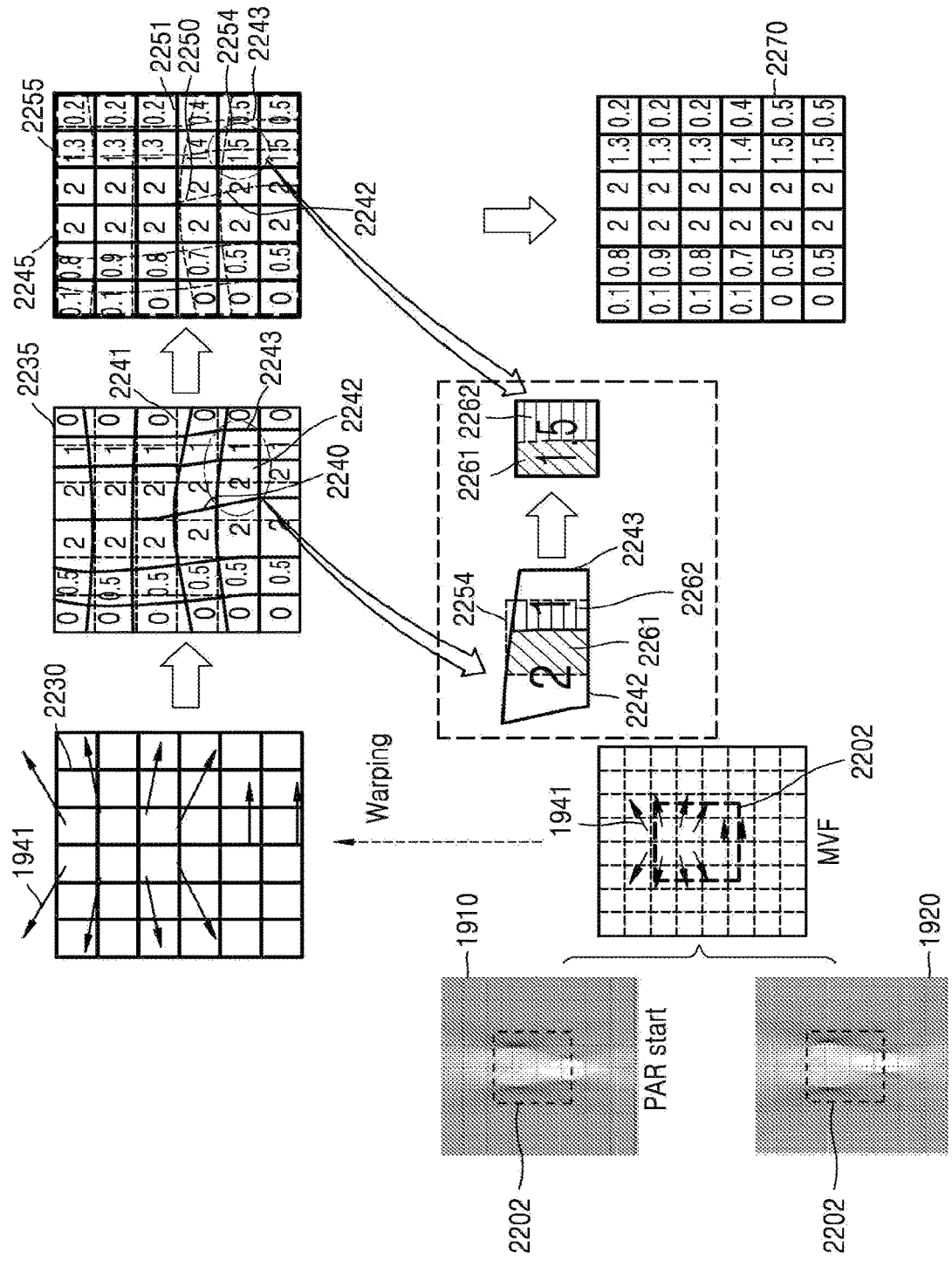

FIGS. 22A and 22B are views for describing a warping operation used to reconstruct a target image.

To reconstruct a target image, the image reconstructor 720 performs back-projection, that is, reflects the filtered projection data acquired at a plurality of views included in the one-cycle angular section in an image domain 2201 indicating the object. In the following description, the back-projection is performed on a partial area 2202 included in the image domain 2201. The area 2202, as illustrated in FIGS. 22A and 22B, may be image data including pixel values or an image represented by pixel values. Also, the area 2202 may be an image space for imaging the object. In FIGS. 22A and 22B, a case in which filtered projection data 2210 acquired as X-rays are projected in a direction 2211 at the first time T1 that is the start time of the one-cycle angular section is back-projected is described as an example. The image data included in the area 2202 may be referred to as back-projected projection data.

Referring to FIG. 22B, the image reconstructor 720 may warp an image grid formed of a plurality of pixels to image the object according to a motion amount of the object at the target time Ttarget based on the first information, and may reconstruct the target image by using a warped image grid.

In detail, referring to FIGS. 22A and 22B, the filtered projection data 2210 is reflected to the image grid included in the filtered projection data 2210. The reflection of the filtered projection data 2210 to the image grid that is an image space is referred to as back-projection.

Accordingly, the area 2202 is filled with pixel values 2213, as illustrated in FIG. 22A. When no motion is generated by the object, motion artifacts may not be generated in a reconstructed target image even if an image is imaged while the filtered projection data 2210 according to each view is accumulatively reflected to the image grid. However, when motion is generated by the object during the one-cycle angular section, a difference between surfaces indicating the same portion of the object is generated in a plurality of pieces of the filtered projection data acquired at each view. Accordingly, when the filtered projection data 2210 according to each view is accumulatively reflected to the image grid to image the image, motion artifacts may be generated in a reconstructed target image.

In the present embodiment, in order to reduce motion artifacts of a moving object, motion correction is performed as described with reference to FIGS. 20A and 21A. In the following description, warping of the image grid of the image reconstructor 720 for motion correction is described in detail.

The image reconstructor 720 warps an image grid 2230 to image the same portion as the area 2202 according to the MVF indicating a motion amount of the object toward the target time Ttarget in the area 2202, by using the first information, for example, MVF information, indicating motion of the object. For example, the upper left area in the image grid 2230 may be warped according to the vectors 1941.

Then, an image grid 2240 warped from the image grid 2230 is generated. The image reconstructor 720 reflects pixel values included in the filtered projection data 2210 to the image grid 2240 that is warped. Accordingly, the pixel values are included in an area 2235 identically corresponding to the area 2202, as illustrated in FIG. 22B. In the area 2235, a rectangular image grid 2241 represented as a dotted grid indicates a general image grid that is not warped.

Next, the image reconstructor 720 resamples the area 2235 including the pixel values according to the warped image grid 2240 to an area 2245 including pixel values according to a rectangular image grid 2241. In detail, the pixel values according to the warped image grid 2240 are interpolated by using a quadratic image pixel matrix and are transformed to pixel values according to Cartesian coordinates.

In the following description, a case of resampling pixel values of pixels 2242 and 2243 included in the warped image grid 2240 to a pixel value 2254 included in the rectangular image grid 2241 is described as an example. The pixel 2242 included in the warped image grid 2240 has a signal value "2" and the pixel 2243 has a signal value "1". In other words, since an image signal value included in the entire area of the pixel 2242 is 2, the signal value "2" is included in the pixel 2242 by being distributed at an area ratio of the pixel 2242. Accordingly, a signal value "1" may be included in a partial area 2261 corresponding to the half of the entire area of the pixel 2242. Also, since the image signal value included in the entire area of the pixel 2243 is 1, the signal value "1" is included in the pixel 2243 (by being distributed at an area ratio in the pixel 2243. Accordingly, a signal value "0.5" may be included in a partial area 2262 corresponding to the half of the entire area of the pixel 2243. Also, a signal value "1.5" that is a sum of the signal value "1" of the partial area 2261 and the signal value "0.5" of the partial area 2262 may be included in the pixel 2254 according to the rectangular image grids 2241 and 2251 including the partial area 2261 and the partial area 2262.

Accordingly, pixel values 2255 are arranged in the area 2245 that is resampled, according to the rectangular image grid 2251. Accordingly, the pixel values 2255 included in the area 2245 may be generated by resampling all pixel values included in the area 2235.

Also, in addition to the above method, various methods may be employed as the method of transforming the pixel values arranged according to a warped image grid to the pixel values arranged according to a rectangular image grid.

Also, motion correction may be performed by using warping with respect to each of all pieces of back-projected projection data corresponding to a plurality of views included in the one-cycle angular section. The target image may be reconstructed by accumulating the back-projected projection data on which motion correction is performed.

Also, the motion correction through warping of an image grid may be performed not for each view, but the motion correction may be performed by each group for a predetermined angular section including a plurality of views.

As in the above-described example, the image reconstructor 720 may generate motion-corrected image data 2270 by using an image grid warped based on the first information.

Figure 23A:
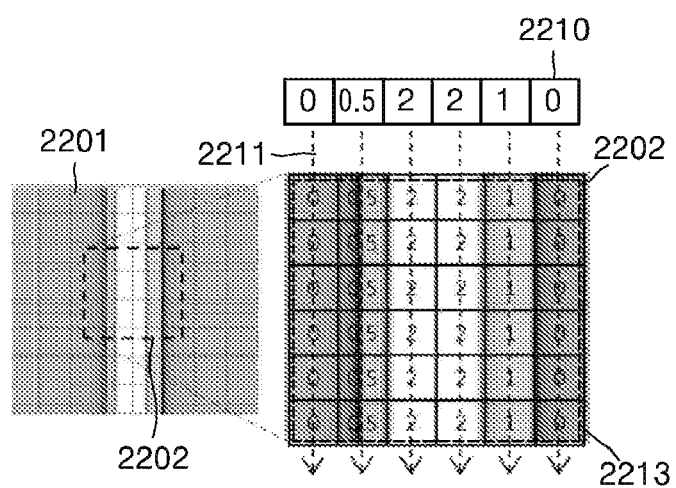
FIGS. 23A and 23B are views for describing the warping operation used to reconstruct a target image.
Figure 23B:
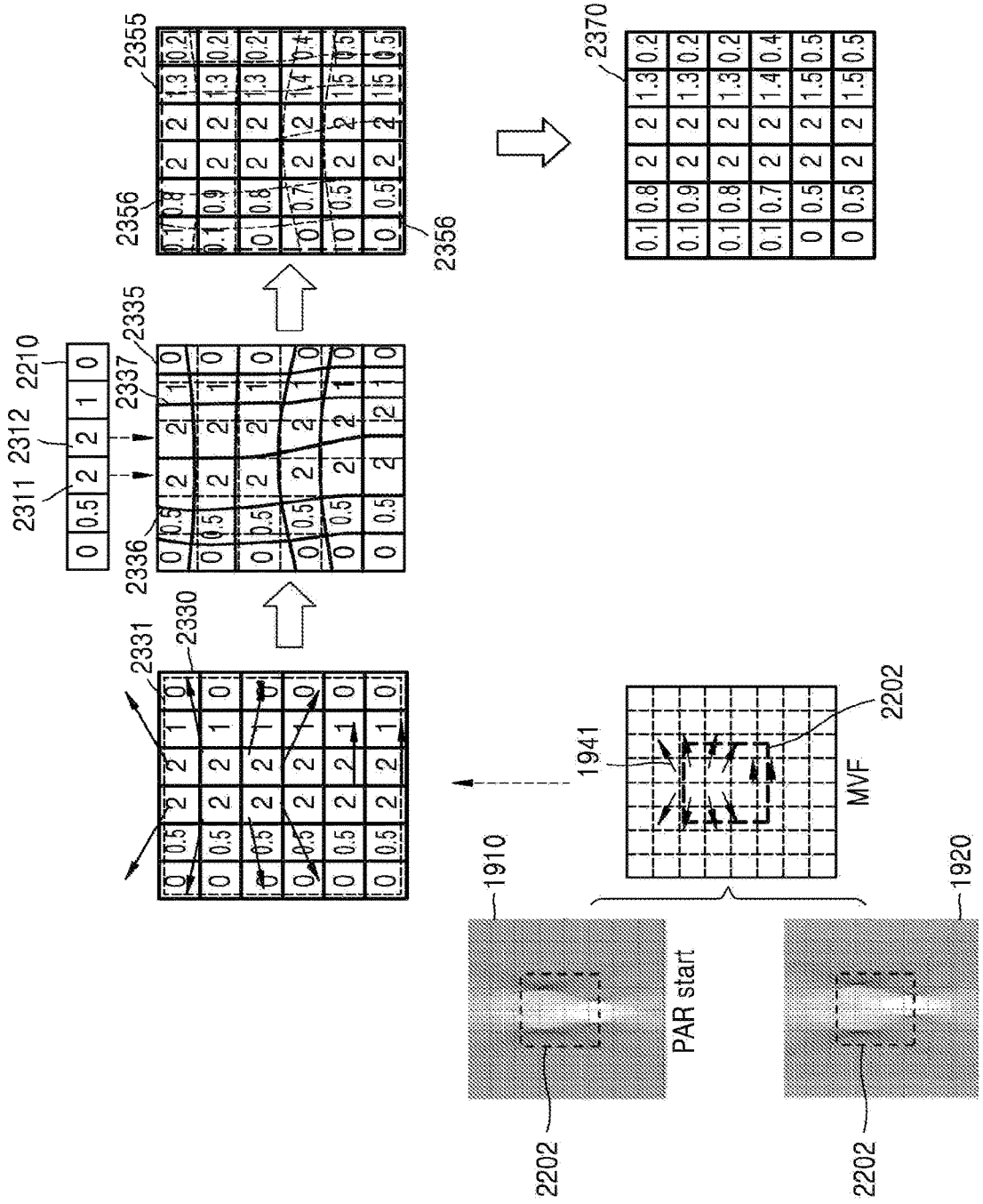

FIGS. 23A and 23B are views for describing the warping operation used to reconstruct a target image. In FIGS. 23A and 23B, a redundant description with FIGS. 22A and 22B is omitted.

In detail, the image reconstructor 720 may generate a motion-corrected target image by warping the back-projected image according to the first information. In detail, in the back-projection process, the image reconstructor 720 may reconstruct the target image by warping the pixel corresponding to the data acquired through a tomography scan based on the first information. In detail, the image reconstructor 720 may warp the pixel based on a motion amount of the object at the target time Ttarget according to the MVF.

Referring to FIGS. 23A and 23B, pixels of an image (or image data) 2330 generated by back-projecting the filtered projection data 2210 are warped based on the MVF information 1940. Accordingly, pixel values 2331 included in the image 2330 are generated into a warped image 2335 corresponding to the object at the target time Ttarget based on the MVF 1941. In detail, a pixel value "2" of filtered projection data 2311 corresponds to pixel value "2" 2336 in third column of the warped image 2335. A pixel value "2" of a filtered projection data 2312 corresponds to a pixel values "2" 2337 in the fourth column of the warped image 2335.

The warped image 2335 generates a motion-corrected image 2355 by resampling in the method described in FIG. 22B. Pixel values 2356 included in the motion-corrected image 2355 accurately reflect motion of the object at the target time Ttarget. Accordingly, motion artifacts in a finally reconstructed target image may be reduced.

Figure 24A:
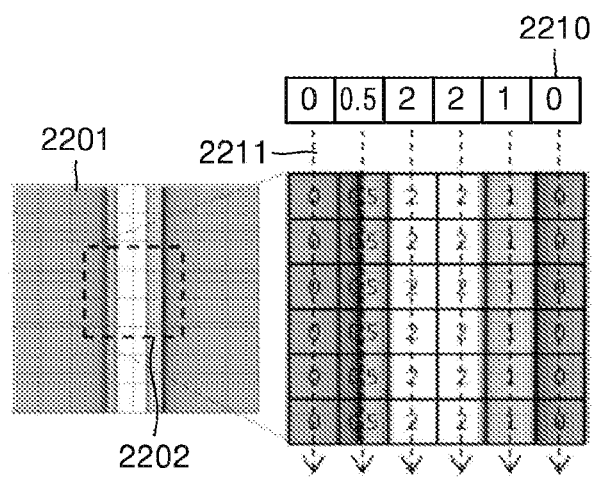

FIGS. 24A and 24B are views for describing an operation of reconstructing a target image. In FIGS. 24A and 24B, redundant descriptions with FIGS. 22A to 23B are omitted. The image reconstructor 720 may perform motion correction in the back-projection process based on the first information. In detail, the image reconstructor 720 may warp the center of a voxel indicating the object based on the first information and may reconstruct a target image by back-projecting the position of a warped voxel. The voxel indicates one unit space in a virtual 3D grid space for imaging the object. In FIGS. 24A and 24B, a case in which the virtual 3D grid space for imaging the object is illustrated with pixels that form a 2D grid space instead of voxels that form a 3D grid space is illustrated as an example.

In detail, the image reconstructor 720 may find which of values of pixels in a detector array should be referred to, by using the MVF from the target time Ttarget to each time when a pixel value at a predetermined position in an image to be reconstructed is affected by a motion at each time. In view of the voxel indicating the object at the target time Ttarget, in order to back-project the filtered projection data at a view other than the target time Ttarget toward a voxel, a destination of a voxel where a voxel moves at a corresponding time is calculated by reflecting motion of the object. The motion amount of a voxel to correct motion of the object may be calculated by using an inverse MVF of the MVF from a corresponding time to the target time Ttarget. The value of the pixel in the detector array to be used after the position of a voxel is moved according to a calculated correction amount may be calculated.

In detail, referring to FIGS. 24A and 24B, the image reconstructor 720 performs field inversion on the MVF indicating the motion amount of the object at the target time Ttarget and generates a field-inversed MVF 2410. The position of each pixel in a back-projected image 2420 is moved by using the field-inversed MVF 2410.

For example, the positions of the pixels in the back-projected image 2420 are moved based on motion vectors 2411, 2421, 2422, and 2423 included in the field-inversed MVF 2410. In detail, a pixel in the first row and sixth column in the back-projected image 2420 is moved as an arrow 2431 based on the vector 2421 and the vector 2422. A pixel in the fifth row and sixth column in the back-projected image 2420 is moved as an arrow 2432 based on the motion vector 2423. Also, the position of a pixel in an area 2427 of the field-inversed MVF 2410 where no motion is detected remains the same.

Next, the image reconstructor 720 calculates which position of the detector array corresponds to a pixel value in a particular pixel when the pixel value of the particular pixel is projected based on a moved pixel position, and takes the filtered projection data 2210 at a calculated position to accumulate a value in the particular pixel, thereby acquiring the back-projected image 2420.

For example, considering the moved position 2431, the center of a pixel 2451 in the first row and sixth column in the back-projected image 2450 is acquired by using a pixel value at a position P1 in the filtered projection data 2210. The position P1 is not located at the center of a pixel 2456 in the first row and sixth column in the filtered projection data 2210, but is located close to a pixel 2455 in the first row and fifth column, thereby being affected by the pixel 2456 and the pixel 2455. Accordingly, the pixel 2451 may have a value "0.2" by being affected by the pixel 2456 having a value "0" and the pixel 2455 having a value "1", as illustrated in FIG. 24B.

Also, similarly, the center of a pixel 2452 in the fifth column and the sixth column in the back-projected image 2450 is located on a surface of the pixel 2452 and a pixel 2457 that neighbor each other according to a motion 2432 of the pixel, as illustrated in FIG. 24B. Accordingly, the pixel 2451 is affected by the pixel 2456 and the pixel 2455. Accordingly, the pixel 2451 may have a value "0.5" that is a middle value between the pixel 2456 having a value "0" and the pixel 2455 having a value "1".

As described above, the image reconstructor 720 may acquire a motion-corrected target image 2470 that is a motion-corrected back-projected image by warping a voxel by using a field-inversed MVF, rather than by using the warping described with reference to FIGS. 22A to 23B.

Figure 25A:
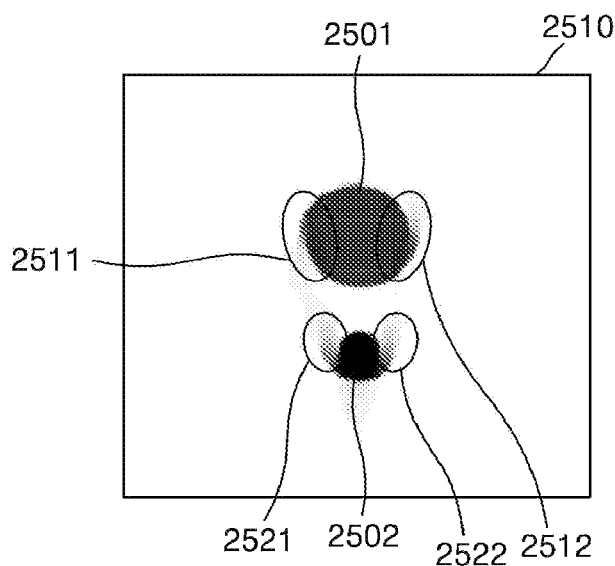
FIGS. 25A and 25B are views for describing reconstructed target images.
Figure 25B:
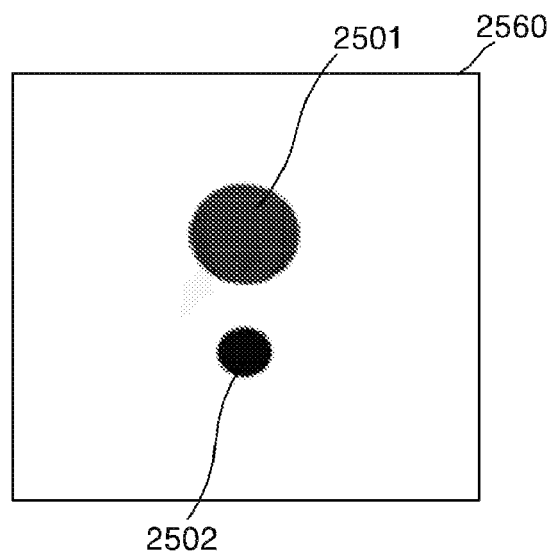

FIGS. 25A and 25B are views for describing reconstructed target images. FIG. 25A illustrates a tomography image 2510 acquired by the half reconstruction method described with reference to FIGS. 18A to 18E. FIG. 25B illustrates a tomography image 2560 that is motion-corrected by using the first information according to an embodiment of the present invention. Also, FIG. 25B illustrates the tomography image 2560 when the target time Ttarget is a middle time between the first time T1 and the second time T2.

Referring to FIG. 25A, blurring 2511 and 2512 are generated in a first target 2501 of the object included in the tomography image 2510 and blurring 2521 and 2522 are generated in a second target 2502.

In contrast, referring to FIG. 25B, in the tomography image 2560 reconstructed in the tomography apparatus 700 according to an embodiment of the present invention, it may be seen that no blurring is generated in the first target 2501 and the second target 2502.

Figure 26:
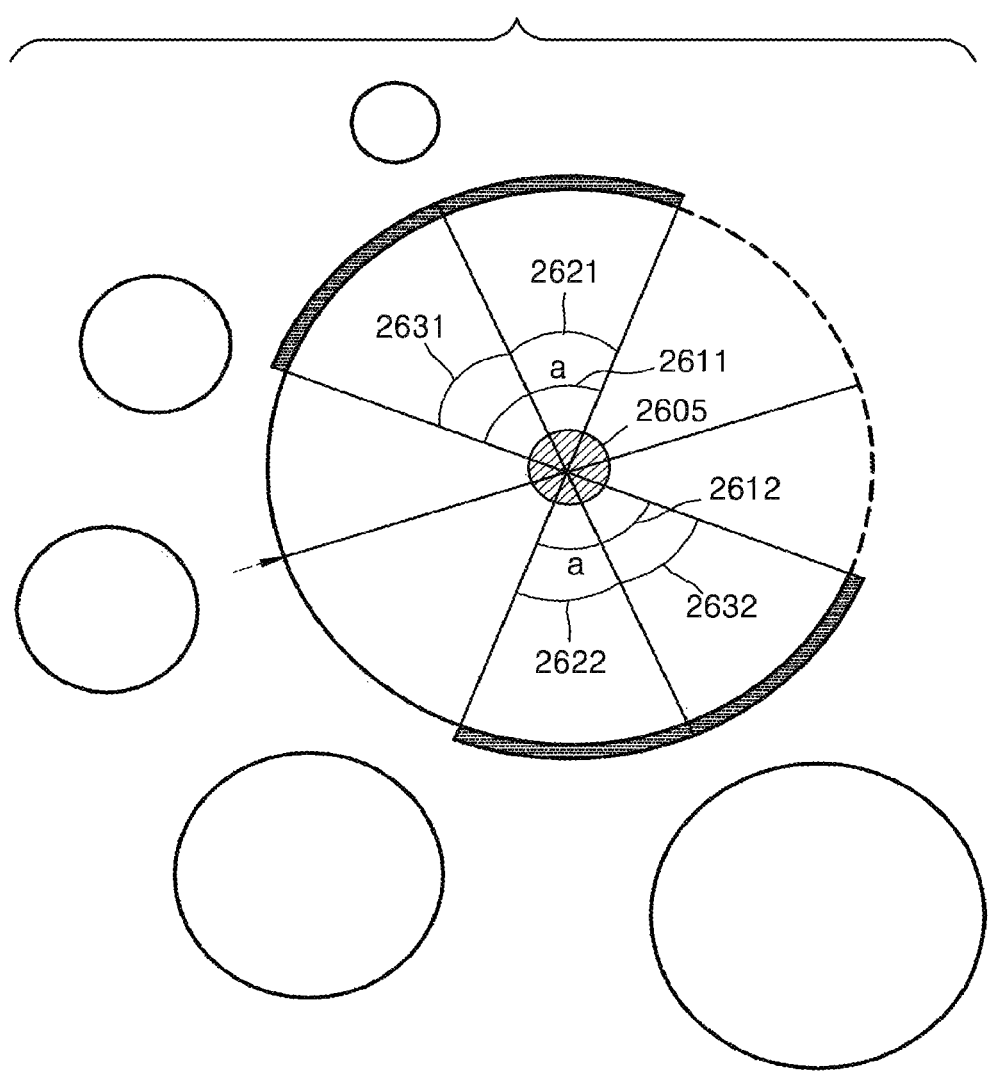
FIG. 26 is a view for describing the measurement of a motion amount of the object.

FIG. 26 is a view for describing the measurement of a motion amount of the object.

When the data acquirer 710 acquires the first image and the second image, as a value "a" of the first angular section and the second angular section increases, temporal resolutions of the first image and the second image may be degraded.

To prevent the degradation of the temporal resolution of the first image and the second image, when a tomography scan is performed by projecting X-rays while the X-ray generator 106 rotates around the object according to the half reconstruction method, a plurality of images are acquired in a plurality of angular sections included in a first "a" angular section 2611 that is an initial additional angular section of the one-cycle angular section, and a plurality of images are acquired in a plurality of angular sections included in a last "a" angular section 2612 that is a last additional angular section of the one-cycle angular section. The first information may be acquired by using the acquired images. In FIG. 26, a case in which each of the first "a" angular section 2611 corresponding to the first angular section 1411 of FIG. 14 and the last "a" angular section 2612 corresponding to the second angular section 1412 of FIG. 14 are divided into two angular sections is illustrated as an example.

Referring to FIG. 26, the data acquirer 710 acquires the first image and the third image respectively from a first angular section 2621 and a third angular section 2631 which are included in the first "a" angular section 2611 of the one-cycle angular section having an angle of 180°+a. The first angular section 2621 may correspond to the first "a/2" of the first "a" angular section 2611, and the third angular section 2631 may correspond to the last "a/2" of the first "a" angular section 2611. The data acquirer 710 acquires the second image and the fourth image respectively from a second angular section 2622 and a fourth angular section 2632 which are included in the last "a" angular section 2612 of the one-cycle angular section. The second angular section 2622 may correspond to the first "a/2" of the last "a" angular section 2612, and the fourth angular section 2632 may correspond to the last "a/2" of the last "a" angular section 2612. The first information indicating a relationship between time and a motion amount of the object may be acquired based on a motion amount between the first image and the second image, and a motion amount between the third image and the fourth image. The first angular section 2621 and the second angular section 2622 are angular sections having a conjugate-angle relationship. The third angular section 2631 and the fourth angular section 2632 are angular sections having a conjugate-angle relationship.

Also, the data acquirer 710 may divide each of the first "a" angular section 2621 and the last "a" angular section 2612 into three or more angular sections, and may acquire the first information by using the image reconstructed from each of the angular sections.

Since the generation of the first information by using the two images acquired in the two angular sections having a conjugate-angle relationship is already described with reference to FIG. 13, a detailed description thereof is omitted.

Figure 27:
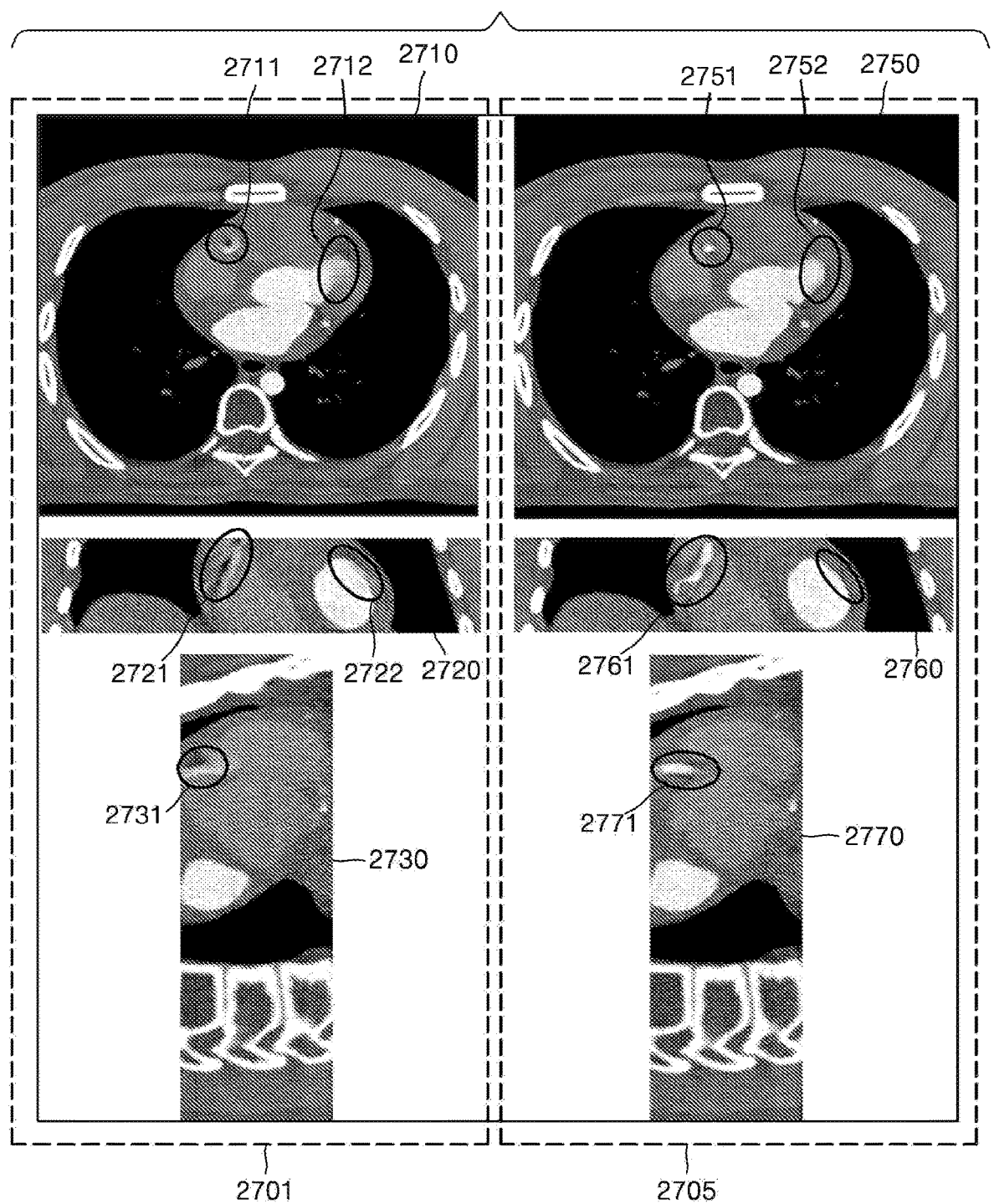
FIG. 27 is a view for describing motion artifacts existing in a reconstructed tomography image.

FIG. 27 is a view for describing motion artifacts existing in a reconstructed tomography image.

Referring to FIG. 27, a block 2701 illustrates tomography images reconstructed by a tomography apparatus of the related art and a block 2705 illustrates tomography images reconstructed by the tomography apparatuses 600 and 700 according to embodiments of the present invention.

Referring to a cross-sectional tomography image 2710 of the block 2701, motion artifacts are generated due to a motion of a coronary artery 2711 in a portion where the coronary artery 2711 is displayed and thus the image is blurred. Also, blurring is generated in a surface 2712 due to a motion of an organ.

Also, in a cross-sectional tomography image 2720, blurring is generated in a horizontal section 2721 of a blood vessel including coronary artery 2711 and thus the blood vessel is not clearly reconstructed. Also, in a cross-sectional tomography image 2730, blurring is generated in a portion 2731 where a blood vessel including coronary artery 2711 is displayed and thus the blood vessel is not clearly reconstructed.

In contrast, in a cross-sectional tomography image 2750 reconstructed in the tomography apparatuses 600 and 700 according to embodiments of the present invention, a portion where a coronary artery 2751 is displayed is clearly reconstructed and thus a surface 2752 of an organ is clearly reconstructed.

Also, in a cross-sectional tomography image 2760, a horizontal cross-section 2761 of a blood vessel including coronary artery 2751 is clearly reconstructed, and in a cross-sectional tomography image 2770, a blood vessel including coronary artery 2751 is displayed is clearly reconstructed.

As described above, in an embodiment of the present invention, the first image and the second image having a high temporal resolution may be acquired by acquiring the first image and the second image in partial angular sections included in the one-cycle angular section. Since a motion amount of the object is measured by using the first image and the second image having a temporal resolution, the first information indicating a relationship between time and a motion amount of the object may more accurately reflect a change in the motion of the object. Also, since an image at the target time Ttarget is reconstructed by using the first information, an image having reduced motion artifacts may be reconstructed.

Figure 28:
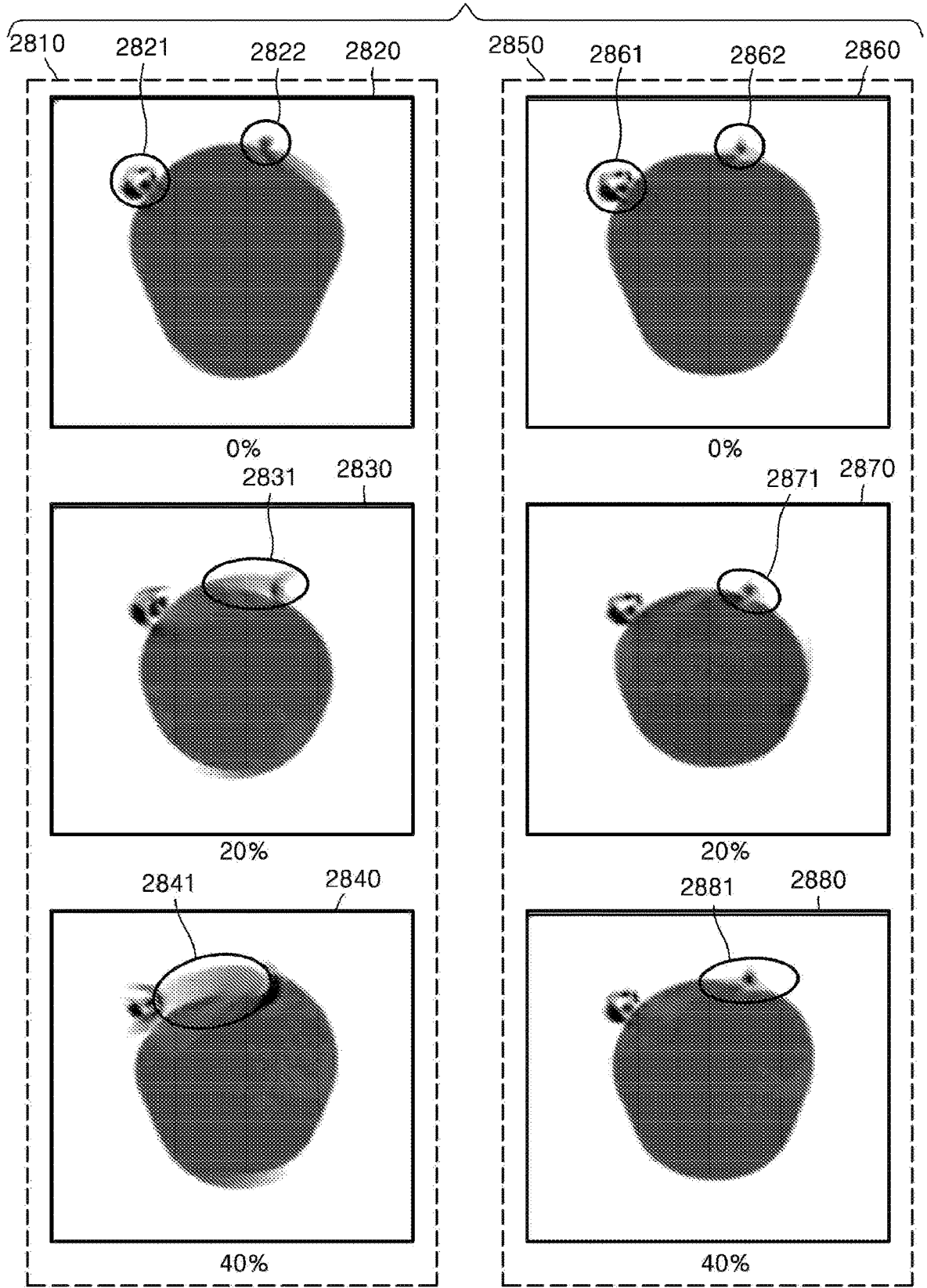
FIG. 28 is a view for describing motion artifacts existing in a reconstructed tomography image.

FIG. 28 is a view for describing motion artifacts existing in a reconstructed tomography image.

Referring to FIG. 28, when a relative time indicating time between R-R peaks of an ECG is expressed in percentage (%), tomography images reconstructed by using times when 0%, 20%, and 40% of relative times as the target time Ttarget are illustrated. For example, if time between R-R peaks is 0.2 second, relative time is 0.2 second and 20% of relative time is (0.2*20/100)=0.04 second. In detail, a block 2810 illustrates tomography images reconstructed by a tomography apparatus of the related art, and a block 2850 illustrates tomography images reconstructed by the tomography apparatuses 600 and 700 according to embodiment of the present invention. In the following description, the tomography images included in the block 2810 are referred to as the "tomography images of the related art" and the tomography images included in the block 2850 are referred to as the "tomography images according to the present invention".

Referring to FIG. 28, when a tomography image 2820 of the related art and a tomography image 2860 according to the present invention are compared with each other at a time when a relative time is 0%, a plurality of areas 2821 and 2822 where blurring is generated due to motion artifacts are present in the tomography image 2830 of the related art, whereas in the tomography image 2860 according to the present invention, motion artifacts are remarkably reduced in areas 2861 and 2862 identically corresponding to the areas 2821 and 2822 where blurring is generated.

Also, when a tomography image 2830 of the related art and a tomography image 2870 according to the present invention are compared with each other at a time when a relative time is 20%, an area 2831 where blurring is generated due to motion artifacts is present in the tomography image 2830 of the related art, whereas in the tomography image 2870 according to the present invention, motion artifacts are remarkably reduced in an area 2871 identically corresponding to the areas 2831 where blurring is generated.

Also, when a tomography image 2840 of the related art and a tomography image 2880 according to the present invention are compared with each other at a time when a relative time is 40%, a plurality of areas 2841 where blurring is generated due to motion artifacts are present in the tomography image 2840 of the related art, whereas in the tomography image 2880 according to the present invention, motion artifacts are remarkably reduced in an area 2881 identically corresponding to the areas 2841 where blurring is generated.

Figure 29A:
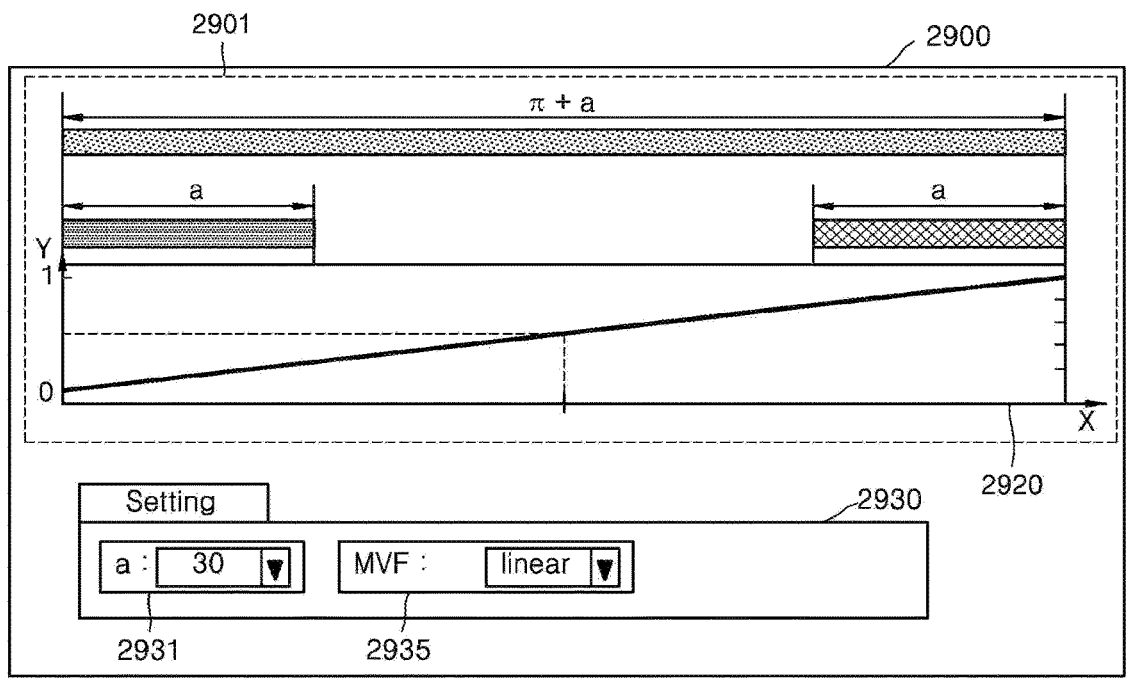
FIGS. 29A and 29B illustrate user interface screens displayed on the tomography apparatus, according to embodiments of the present invention.
Figure 29B:
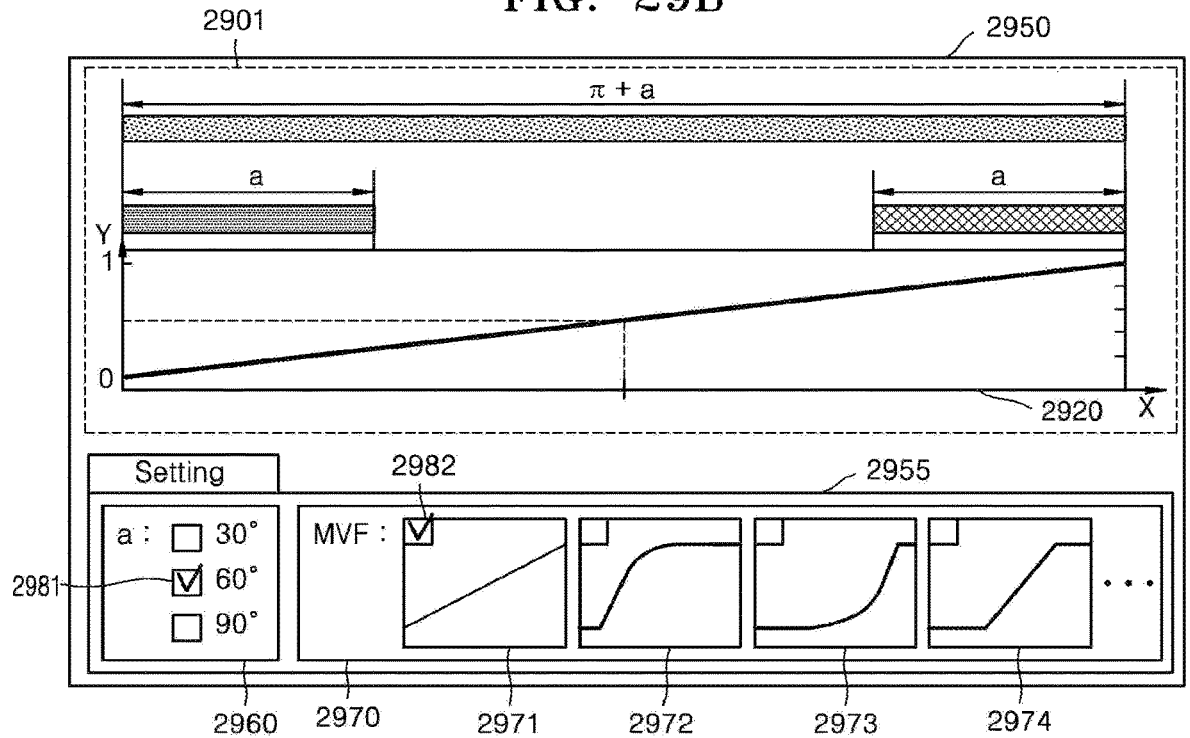

FIGS. 29A and 29B illustrate user interface screens displayed on the tomography apparatus, according to embodiments of the present invention.

Referring to FIG. 29A, the display 740 displays a user interface screen 2900 for setting the first information. In detail, the user interface screen 2900 includes a first menu 2930 for setting a relationship between time and a motion amount of the object in the first information.

Also, the user interface screen 2900 may further include a second menu 2901 for displaying the first information. Since the first information displayed in the second menu 2901 identically corresponds to the first information 1380 described with reference to FIG. 13C, a redundant description with FIG. 13C is omitted.

The first menu 2930 may include a submenu 2935 for setting a relationship between the time and the motion amount of the object. In the submenu 2935, any one of relationships included in the submenu 2935 may be selected or an equation for setting a relationship may be directly input, according to whether the relationship between the time and the motion amount of the object is linear or quadratic.

Also, the first menu 2930 may further include a second submenu 2931 for setting an angular value of the first angular section and the second angular section. Accordingly, a user may directly set the angular value of the first angular section and the second angular section by using the second submenu 2931.

In FIG. 29A, a case in which the relationship between the time and the motion amount of the object is linear in the submenu 2935 is illustrated as an example.

Also, the user interface 750 receives an input of the second information corresponding to the relationship between the time and the motion amount of the object through the user interface screen 2900. In detail, when the user selects an item "linear" in the submenu 2935 of the user interface screen 2900, the data acquirer 710 generates the first information based on the second information. In the above-described example, when the item "linear" is selected, the data acquirer 710 may generate first information 2920 based on a linear relationship between the time and the motion amount of the object.

Also, although FIGS. 29A and 29B illustrate a case in which the display 740 displays a user interface screen as an example, the user interface screen used in FIGS. 29A and 29B may be generated by the user interface 750 and transmitted to an external display (not shown) that is not included in the tomography apparatus 700. Then, the external display may display the received user interface screen and the user viewing the displayed user interface screen and may input information to set the first information through the user interface 750.

Also, FIG. 29B illustrates another example of the user interface screen for setting the first information.

Referring to FIG. 29B, the display 740 displays a user interface screen 2950 for setting the first information. In detail, the user interface screen 2950 includes a first menu 2955 for setting the relationship between the time and the motion amount of the object in the first information. The second menu 2901 of FIG. 29B is identical with the second menu 2901 of FIG. 29A.

Referring to FIG. 29B, the first menu 2955 may include a first submenu 2970 for setting the relationship between the time and the motion amount of the object. The first submenu 2970 includes at least one of items 2971, 2972, 2973, and 2974 directly displaying the first information as illustrated in FIG. 29B.

The user may select any one of the items 2971, 2972, 2973, and 2974 included in the first submenu 2970 by using a selection cursor 2982. FIG. 29B illustrates a case in which the first item 2971 is selected. As the first item 2971 is selected, the first information 2920 may be set in the second menu 2901 as illustrated in FIG. 29B.

Also, the first menu 2950 may further include the second submenu 2960 for setting the angular value of the first angular section and the second angular section. The second submenu 2960 includes a plurality of predetermined angular values as illustrated in FIG. 29B. The user may select any one of the angular values included in the second submenu 2960 by using a selection cursor 2981. FIG. 29B illustrates a case in which an item "60°" is selected in the second submenu 2960 as an angular value of the first angular section and the second angular section.

In addition to the user interface screens 2900 and 2950 of FIGS. 29A and 29B, user interface screens having a variety of forms for setting the first information may be generated and displayed.

Also, the data acquirer 710 may automatically set the angular value of the first angular section and the second angular section. Also, the data acquirer 710 may automatically set a graph form of the first information.

Figure 30:
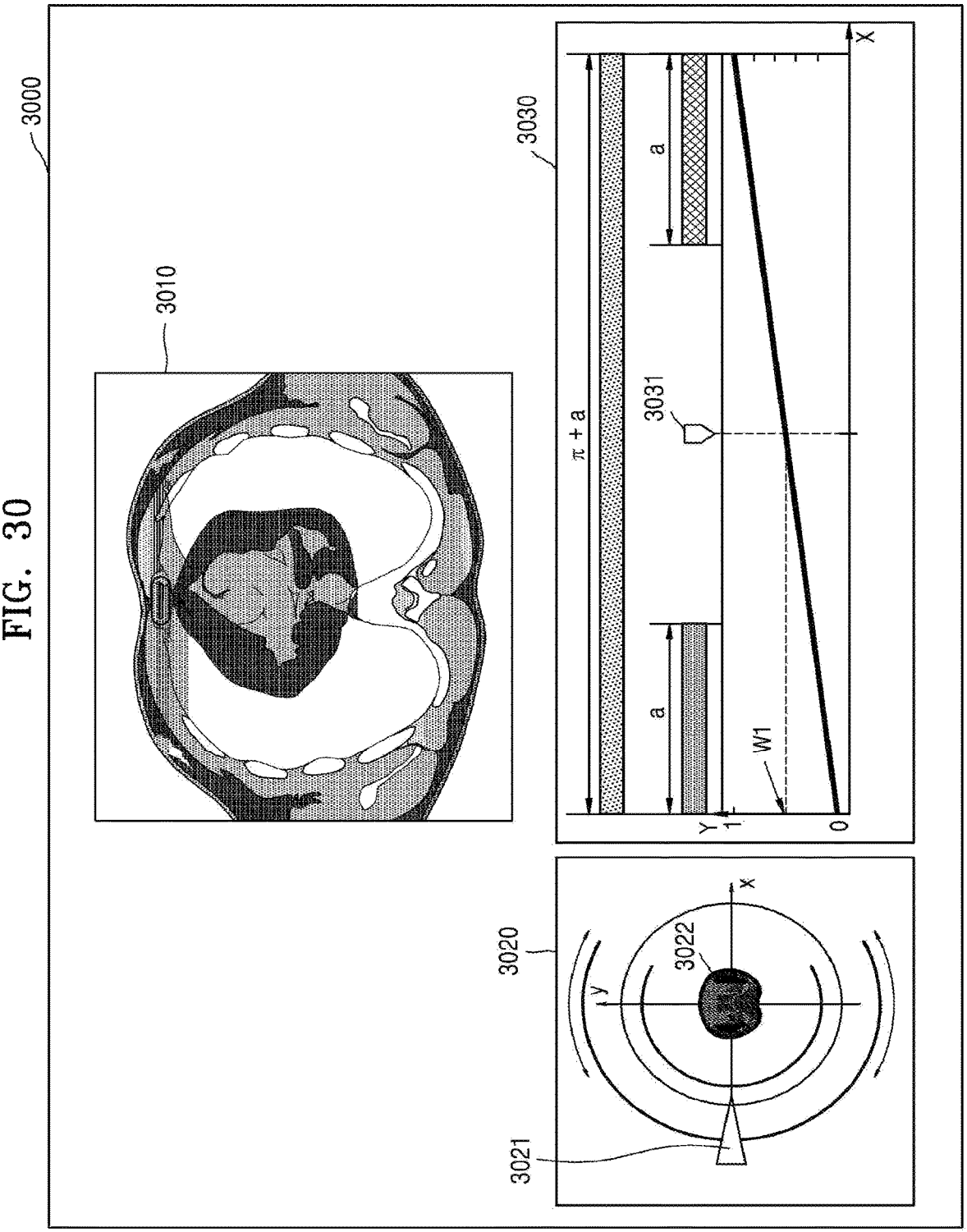
FIG. 30 is a view illustrating the user interface screen displayed on the tomography apparatus, according to an embodiment of the present invention.

FIG. 30 is a view illustrating the user interface screen displayed on the tomography apparatus, according to an embodiment of the present invention.

Referring to FIG. 30, the display 740 may display a user interface screen 3000 including a menu for setting the target time Ttarget.

Referring to FIG. 30, the menu may include at least one of a first submenu 3020 and a second submenu 3030 to set the target time Ttarget.

In detail, the first submenu 3020 may include a one-cycle angular section around an object 3022 in the form of coordinates as illustrated in FIG. 30. A user may select the target time Ttarget by selecting a predetermined position or time included in the one-cycle angular section through the first submenu 3020 by using a cursor 3021.

Also, the second submenu 3030 may include information indicating the one-cycle angular section, including the first information. Since the second submenu 3030 identically corresponds to the contents illustrated in FIG. 13C, a redundant description with FIG. 13C is omitted. The user may select the target time Ttarget by selecting a predetermined position or time included in the one-cycle angular section through the second submenu 3030 by using a cursor 3031.

Also, when both the first submenu 3020 and the second submenu 3030 are displayed by being included in the user interface screen 3000 and the target time Ttarget is selected by using, for example, the cursor 3021 in the first submenu 3020, the cursor 3031 in the second submenu 3030 may be displayed at a position corresponding to the selected target time. Alternatively, the target time Ttarget may be selected by using the cursor 3031 in the second submenu 3030, and the cursor 3021 in the first submenu 3020 may be displayed at a position corresponding to the selected target time.

Also, the user interface screen 3000 may display a target image 3010 corresponding to a selected target time.

Accordingly, the user may easily set the target time by using the user interface screen 3000. When an unclear surface or an image error exists in a reconstructed target image 3010, the user may observe the reconstructed target image 3010 included in the user interface screen 3000, and reset the target time. Accordingly, the target image 3010 in which the unclear surface or an image error is reduced may be reconstructed again.

Figure 31A:
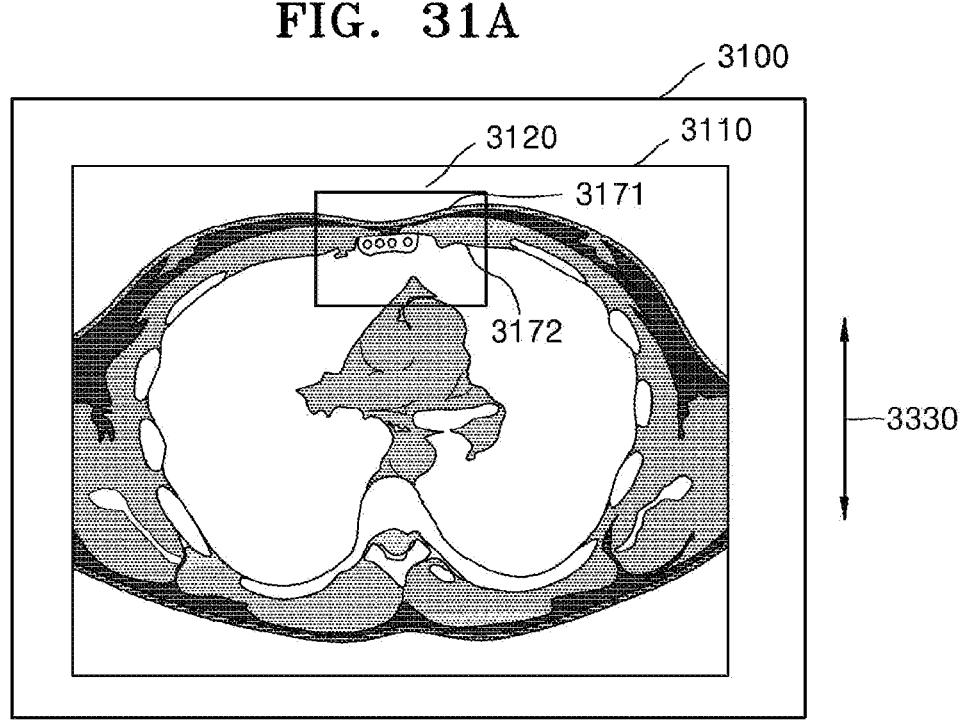
FIGS. 31A and 31B are views illustrating the user interface screen displayed on the tomography apparatus, according to an embodiment of the present invention.
Figure 31B:
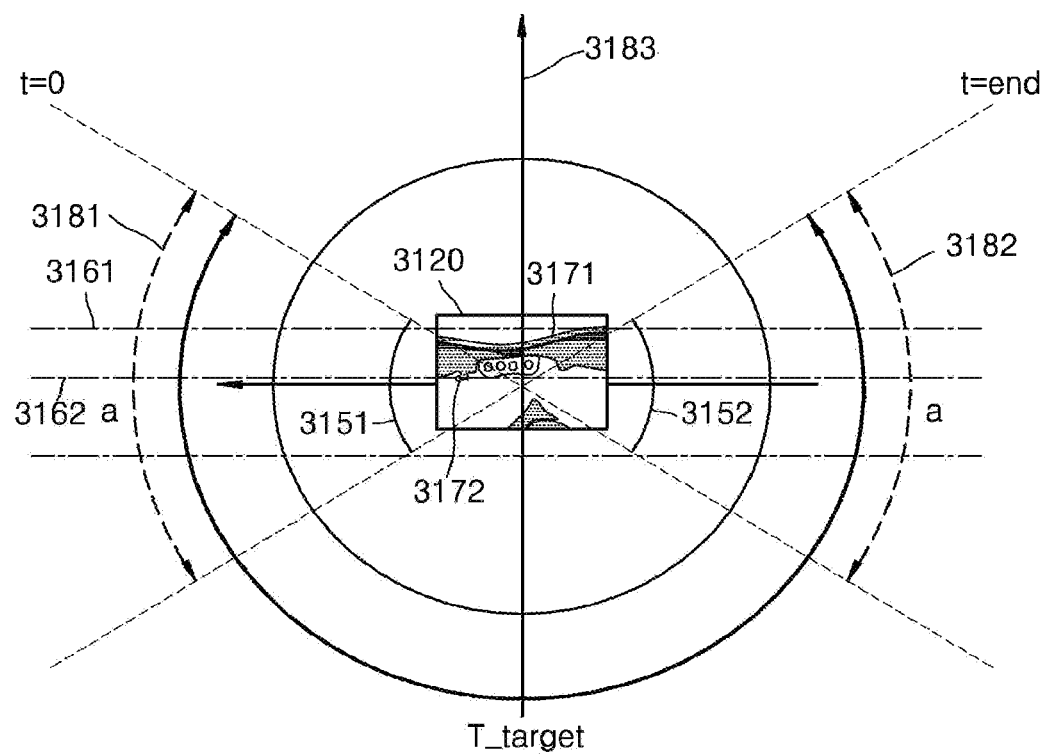

FIGS. 31A and 31B are views illustrating the user interface screen displayed on the tomography apparatus, according to an embodiment of the present invention. In detail, FIG. 31A is a view for describing setting of a region of interest (ROI). FIG. 31B illustrates a configuration for setting a position or view angle of the first angular section and the second angular section according to a set ROI.

The display 740 may display a medical image. The medical image may be various medical images such as a scout image, a tomography image, an MRI image, an X-ray image, or an ultrasonic image.

The user may set a predetermined area of a medical image as an ROI through the user interface 750.

Referring to FIG. 31A, a cross-sectional tomography image 3110 is illustrated as an example of a medical image 3100 displayed in the display 740.

The user may set the ROI through the user interface 750. Also, the data acquirer 710 may automatically extract a portion needing precise image interpretation such as an area suspected of disease in the medical image and may set an extracted portion as an ROI.

The data acquirer 710 may extract a surface included in the ROI and may set the first angular section and the second angular section based on a direction of the extracted surface. In detail, the data acquirer 710 may extract surfaces 3171 and 3172 included in the ROI and may acquire a view angle corresponding to the extracted area. At least one of the first angular section, the second angular section, a start position of the one-cycle angular section, an end position of the one-cycle angular section, and the target time is set according to the acquired view angle, the first image and the second image may be respectively acquired in the first angular section and the second angular section corresponding to the above-described setting.

As described with reference to FIGS. 16 and 17, a direction of a surface that is clearly sampled varies according to a direction in which an X-ray beam is irradiated. Accordingly, surfaces included in an ROI 3120 may be more clearly sampled by adjusting the direction of an X-ray beam according to a direction of a surface included in the ROI 3120.

In detail, referring to FIG. 31B, the data acquirer 710 may set directions 3161 and 3162 corresponding to surfaces 3171 and 3172 included in the ROI 3120 or a view angle of the X-ray generator 106. The positions of the first angular section and the second angular section are set according to the set direction or view angle. For example, when directions in which the surfaces 3171 and 3172 extend are the directions 3161 and 3162, a first angular section 3151 and a second angular section 3152 may be set to correspond to the directions 3161 and 3162. Accordingly, the first image is acquired by projecting X-rays from the left side of an ROI 3120, and the second image may be acquired by projecting X-rays from the right side of the ROI 3120.

The data acquirer 710 may generate the first information by using the first image and the second image.

As described above, when the first angular section 3151 and the second angular section 3152 are set based on the directions of the surfaces 3171 and 3172 included in the ROI 3120, the surfaces 3171 and 3172 included in the ROI 3120 may be more clearly sampled and thus the quality of a reconstructed image may be improved.

Also, the image reconstructor 720 may set at least one of the first angular section, the second angular section, a start portion of the one-cycle angular section (angular position corresponding to t=0), an end position of the one-cycle angular section (angular position corresponding to t=end), and the target time Ttarget, considering a direction in which an object moves. For example, the first angular section and the second angular section may be set such that a measurement of motion may be possible with respect to a direction in which a lot of motions of the object are generated.

When the object is a person and a tomography image to be acquired is a cross-sectional tomography image as illustrated in FIG. 31A, for example, a lot of motions are generated in two directions as illustrated by a double-head arrow 3330 along the front and back sides of the person due to the breathing or heartbeat of the person.

In detail, a lot of motions are generated in the direction 3330 and, in order to observe the motions in the direction 3330 in a better way, a surface, for example, the surface 3171, extending in a direction perpendicular to the direction 3330 or in a direction adjacent to the direction perpendicular to the direction 3330 is clearly imaged. In other words, when a lot of motions of the direction 3330 are generated, the surface 3171 is clearly imaged in the first image and the second image that are used to acquire the first information. As the first information is acquired by comparing the surface 3171 imaged in the first image and the surface 3171 imaged in the second image, the motion amount of the object in the direction 3330 may be accurately identified.

Accordingly, in order to measure the motion amount of the object in the direction 3330, the first angular section and the second angular section may be set to be the first angular section 3181 and the second angular section 3182. Then, the first information with respect to the motion of the object in a first direction 3183 (same as the direction 3330) perpendicular to the directions 3161 and 3162 in which X-rays are projected, in the first angular section 3181 and the second angular section 3182, may be acquired. When motion correction is performed by applying a motion amount with respect to the first direction 3183, a target image corresponding to the target time Ttarget may be further reconstructed.

Also, the tomography apparatus 700 may perform the following operations.

The data acquirer 710 reconstructs at least one reference image to estimate motion of the object by performing a tomography scan while rotating in an angular section less than one turn around the object, and acquires the first information indicating the motion amount of the object. The "angular section less than one turn" may identically correspond to the above-described one-cycle angular section. Also, at least one reference image may be a partial angular image acquired in a partial angular section included in the one-cycle angular section. In detail, the reference image may be at least one of the first image 1310 and the second image 1320 which are described in FIG. 13. Also, the reference image may be at least one of the first image and the third image respectively acquired in the first angular section 2621 and the third angular section 2631, and the second image and the fourth image respectively acquired in the second angular section 2622 and the fourth angular section 2632, which are described with reference to FIG. 26.

In detail, the data acquirer 710 acquires the first image corresponding to the first time and acquires the second image corresponding to the second time through the PAR method. The first information indicating the relationship between the time and the motion amount of the object based on the motion amount between the first image and the second image.

The image reconstructor 720 performs the above-described motion correction operation to reconstruct a target image having reduced motion artifacts corresponding to the target time Ttarget in one cycle by using the first information acquired by the data acquirer 710.

Also, the tomography apparatus 700 may perform the following operation.

The data acquirer 710 acquires the first image and the second image respectively corresponding to the first time and the second time and indicating parts of the surfaces forming the object, by performing a tomography scan on the object. The data acquirer 710 acquires the first information indicating the motion of the object by using the acquired first image and second image. The first information may indicate the relationship between the time and the motion amount of the surface forming the object corresponding to the MVF between the first image and the second image.

The image reconstructor 720 reconstructs the target image by using the first information.

Also, the tomography apparatus 700 may perform the following operation.

The data acquirer 710 performs a tomography scan on a moving object and acquires the first partial image and the second partial image by using data acquired in a start angular section and an end angular section facing the start angular section, respectively. The data acquirer 710 acquires the first information indicating the relationship between the time and the motion amount of the surface of the object corresponding to the MVF between the first partial image and the second partial image.

The image reconstructor 720 reconstructs a target image indicating the object at the target time Ttarget, based on the first information.

Also, the tomography apparatus 700 may perform the following operation.

The data acquirer 710 performs a tomography scan on the object, acquires the first image and the second image respectively corresponding to the first time and the second time and indicating parts of surface forming the object, and acquires the first information indicating the motion of the object by using the first image and the second image. The image reconstructor 720 reconstructs the target image indicating the object by warping at least one of raw data needed for the half reconstruction method and an image acquired by filtered back-projecting the raw data, based on the first information.

Also, the tomography apparatus 700 may perform the following operation.

The data acquirer 710 acquires the first image and the second image that are partial images by using the data acquired in each of the first angular section corresponding to the first view point and the second angular section corresponding to the second view point and facing the first angular section, by performing a tomography scan on the object. The data acquirer 710 may acquire the first information indicating the motion amount of the object based on the first image, the second image, and the additional information.

The image reconstructor 720 reconstructs the target image indicating the object at the target time, based on the first information.

In detail, in performing a tomography scan on the object, even when the object does not move by itself, the object may have motion due to external factors. For example, when vibrations, motions, or shakes occur in the table where the object is located, and/or the tomography apparatus, which may generate motions to the object, the object may be vibrated, moved, or shaken. The generation of motion of the object due to the external factors may cause blurring in the imaging of the object.

When blurring occurs in the imaging of the object due to the external factors as described above, the data acquirer 710 may acquire the first image, the second image, and the first information and remove the blurring in the imaging of the object due to the external factors.

Also, the tomography apparatus 700 may perform the following operation.

The data acquirer 710 acquires the first image and the second image that are partial images by using the data acquired in each of the first angular section corresponding to the first view point and the second angular section corresponding to the second view point and facing the first angular section, by performing a tomography scan on the object. The data acquirer 710 may acquire additional information that is information about motion generated in the object during tomography. The data acquirer 710 may acquire the first information indicating the motion amount of the object based on the first image, the second image, and the additional information.

The image reconstructor 720 reconstructs the target image indicating the object at the target time, based on the first information.

In detail, the additional information may be used in performing a tomography scan on the object in order to accurately predict a motion pattern of the object. For example, when the object is a heart and the heart suddenly beats fast or beats in an unexpected pattern, additional information that is information about motion of the heat is acquired and the first information may be set by reflecting the additional information.

Also, when the object does not move and motion such as vibrations, movements, and shakes of the tomography apparatus which causes motion in the table where the object is located or in the object is generated, motion may be generated in the object due to the external factors of the object. In this case, additional information that is information about motion generated in the object during tomography due to the external factors may be acquired and the first information may be set by reflecting the additional information.

For example, the additional information may be acquired by monitoring motion of the object being tomography scanned, by using a monitoring apparatus that monitors motion of the object such as a digital stethoscope. The shape of a graph may be set in the first information by reflecting the motion pattern of the object generated in the one-cycle angular section and acquired by the digital stethoscope. For example, when the motion pattern of the object has a linear pattern in the one-cycle angular section according to the additional information, the data acquirer 710 may set the first information in the form as illustrated in the first item 2971 of FIG. 29. In another example, when the object moves fast in the initial section of the one-cycle angular section and then hardly moves after the initial section of the one-cycle angular section, according to the additional information, the first information may be set in the form as illustrated in the item 2972 of FIG. 29.

Also, the tomography apparatus 700 may further include a monitor (not shown) for acquiring the additional information. In this case, the data acquirer 710 may receive the additional information from the monitor and acquire the first information based on the received additional information. The monitor may include various types of apparatuses for monitoring motion of the object, for example, a digital stethoscope, a motion detection sensor, and an image sensor for detecting motion.

Also, the tomography apparatus 700 may not include the monitor for acquiring the additional information and may use only the additional information received from a monitor (not shown) that is externally connected.

As described above, the motion amount generated in the one-cycle angular section is measured based on the first and second images, and the motion pattern of the object in the one-cycle angular section may be set based on the additional information, thereby acquiring the first information that more accurately indicates the motion of the object.

Figure 32:
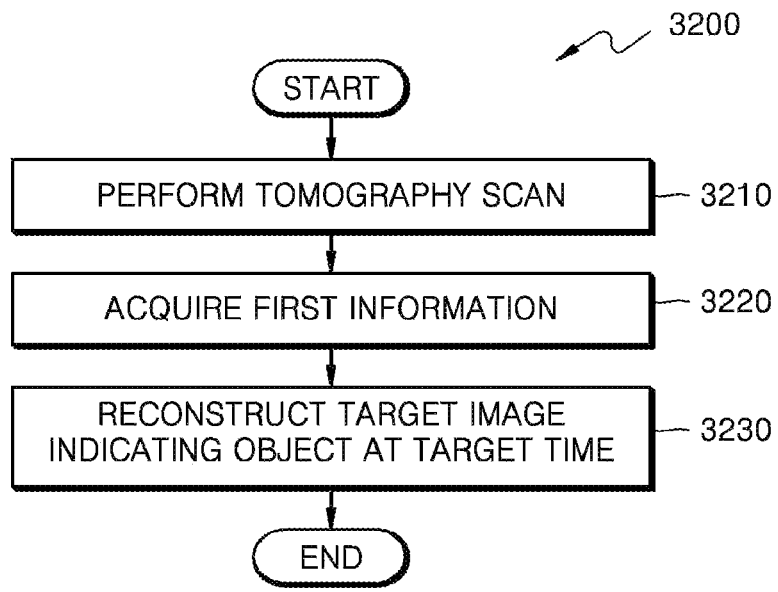
FIG. 32 is a flowchart for explaining a method for reconstructing a tomography image according to an embodiment of the present invention.

FIG. 32 is a flowchart for explaining a method 3200 for reconstructing a tomography image according to an embodiment of the present invention. The operation of steps included in the tomography image reconstruction method 3200 according to the present embodiment is the same as the operation of elements included in the tomography apparatuses 600 and 700 according to the embodiments of the present invention described with reference to FIGS. 1 to 31. Accordingly, in describing the tomography image reconstruction method 3200, redundant descriptions with FIGS. 1 to 31 are omitted.

Referring to FIG. 32, the tomography image reconstruction method 3200 according to an embodiment of the present invention performs a tomography scan on the object (Operation 3210). In detail, through the tomography scan, the first image that is a partial image is acquired by using the data acquired in the first angular section corresponding to the first time, and the second image that is a partial image is acquired by using the data acquired in the second angular section corresponding to the second time (Operation 3210). The operation 3210 may be performed by the data acquirer 710 of the tomography apparatus 700. Each of the first angular section and the second angular section may have a value less than 180°.

The first information indicating the motion amount at a time point based on the motion amount between the first image and the second image is acquired in the operation 3210 (Operation 3220). In detail, the first information may be acquired by comparing only the first image and the second image. The operation 3220 may be performed by the data acquirer 710 of the tomography apparatus 700. The first information may be a motion amount of the object at the time point. Also, when a moving object is scanned, the object being imaged in the first image and the object being imaged in the second image are different from each other in at least one of a size, a position, and a shape.

In detail, the first information may indicate a motion amount of a surface forming the object. Also, the first information may indicate the relationship between the time and the motion amount of the surface forming the object corresponding to the MVF between the first image and the second image.

Also, in the acquisition of the first information, a user interface screen for setting the first information is displayed, and the second information corresponding to the relationship between the time and the motion amount of the object in the first information may be received through the displayed user interface screen. The first information may be generated based on the second information.

Also, when a tomography scan is performed while an X-ray generator 106 rotates around the object and projects X-rays to the object, the operation 3210 of acquiring the first image and the second image may include operations of acquiring the first partial image and the third partial image respectively from the first angular section 2621 and the third angular section 2631, which are included in the first "a" angular section 2611 of the angular section having an angle of 180°+a that is an angular section of one cycle, and the second partial image and the fourth partial image respectively from the second angular section 2622 and the fourth angular section 2632, which are included in the last "a" angular section 2612 of the one-cycle angular section, as illustrated in FIG. 26. The first information indicating the relationship between the time and the motion amount of the object may be acquired based on the motion amount between the first partial image and the second partial image, and the motion amount between the third partial image and the fourth partial image. The first angular section and the second angular section have a conjugate-angle relationship with each other, and the third angular section and the fourth angular section have a conjugate-angle relationship with each other.

Also, the tomography image reconstruction method 3200 may further include, prior to the operation 3210, operations of displaying a medical image and selecting an ROI in the medical image (not shown). The operation 3210 may include operations of extracting a surface line included in the ROI, acquiring a view angle corresponding to an extracted surface line, setting the first angular section and the second angular section according to the view angle, and acquiring the first image and the second image respectively from the first angular section and the second angular section.

Also, the tomography image reconstruction method 3200 may further include an operation of displaying a user interface screen including a menu for setting a target time (not shown).

The target image corresponding to the target time between the first time and the second time is reconstructed based on the first information acquired in the operation 3220 (Operation 3230). The operation 3230 may be performed by the image reconstructor 720 of the tomography apparatus 700. In detail, the target image may be acquired through motion correction based on the motion amount of the object at the target time, based on the first information.

Also, in the reconstructed target image, a degree of motion correction of the object included in the target image may vary according to the target time.

Also, in the target image, when the target time corresponds to a middle angle between the first angular section and the second angular section, motion correction of the object may be improved compared to motion correction of the object when the target time does not correspond to the middle angle.

Figure 33:
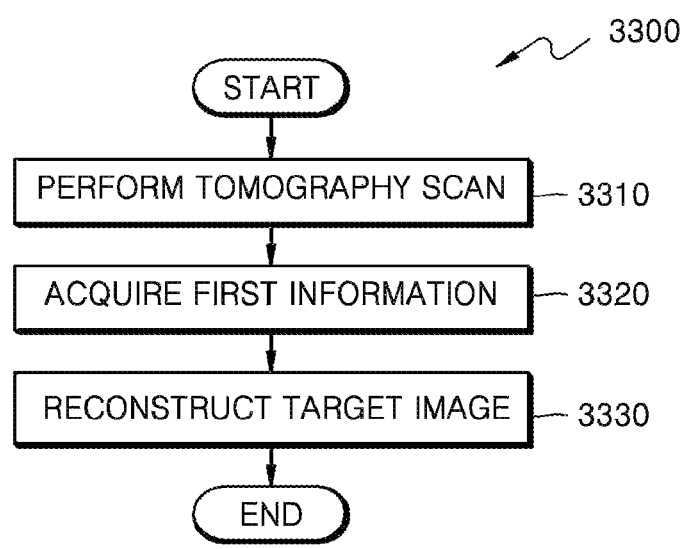
FIG. 33 is a flowchart for explaining a method for reconstructing a tomography image according to another embodiment of the present invention.

FIG. 33 is a flowchart for explaining a method 3300 for reconstructing a tomography image according to another embodiment of the present invention. The operation of steps included in the tomography image reconstruction method 3300 according to the present embodiment is the same as the operation of elements included in each of the tomography apparatuses 600 and 700 according to the embodiments of the present invention described with reference to FIGS. 1 to 31. Accordingly, in describing the tomography image reconstruction method 3300, redundant descriptions with FIGS. 1 to 31 are omitted.

Referring to FIG. 33, in the tomography image reconstruction method 3300 according to the present embodiment, a tomography scan is performed on a moving object (Operation 3310). In detail, the first image and the second image that are partial images respectively corresponding to the first time and the second time and indicating the same portions of surfaces forming the object are acquired. In detail, the first image and the second image are acquired by using the data acquired in each of the first partial angular section corresponding to the first time, and the second angular section corresponding to the second time and facing the first angular section, by performing a tomography scan while rotating in an angular section less than one turn around the object. The operation 3310 may be performed by the data acquirer 710 of the tomography apparatus 700.

The first information indicating the motion of the object is acquired by using the first image and the second image acquired in the operation 3310 (Operation 3320). The operation 3320 may be performed by the data acquirer 710 of the tomography apparatus 700. The first information may indicate the relationship between the time and the motion amount of the surface forming the object corresponding to the MVF between the first image and the second image.

A corresponding target image is reconstructed based on the first information acquired in the operation 3320 (Operation 3330). In detail, the target image may be reconstructed by performing the motion correction described with reference to FIGS. 19A to 24. The operation 3330 may be performed by the image reconstructor 720 of the tomography apparatus 700.

Figure 34A:
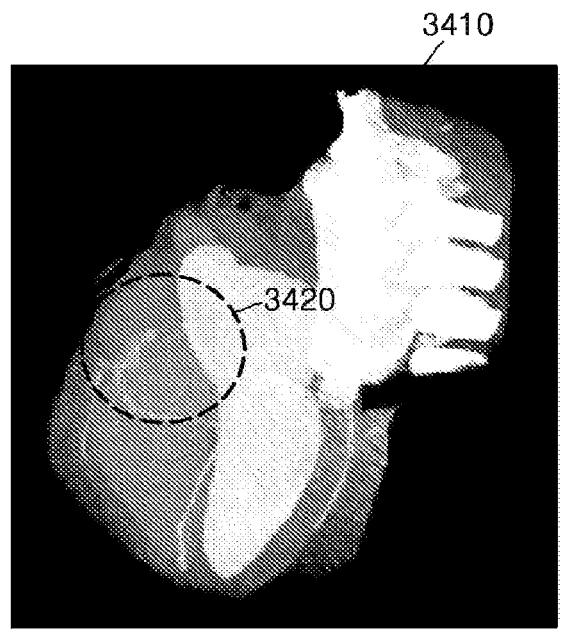
FIG. 34A is a reconstructed target image generated by a related art CT system.

FIG. 34A is a reconstructed target image generated by a related art CT system. Referring to FIG. 34A, reconstructed target image 3410 is reconstructed by a related art CT system (not shown) includes X-ray detector having 128 detector raw under the condition that a rotation time is 300 ms and heart rate is 70 bpm.

Referring to FIG. 34A, as shown in a region 3420, blurring due to the motion is incurred in the reconstructed target image 3410. Accordingly, coronary artery of heart in the reconstructed target image 3410 is not clearly imaged.

Figure 34B:
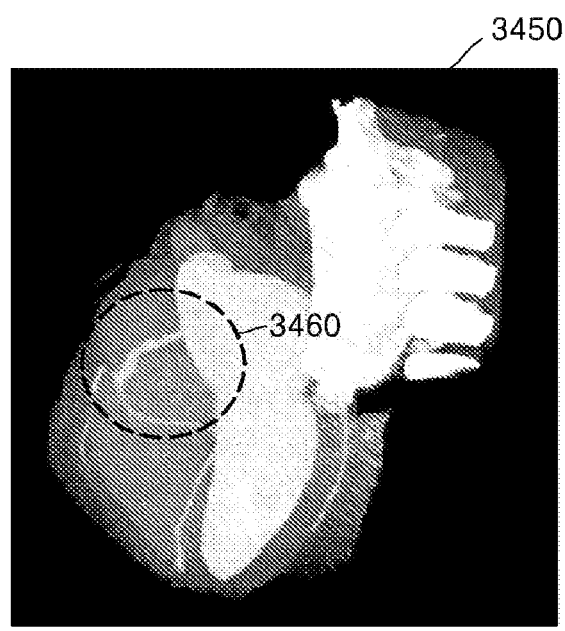
FIG. 34B is a reconstructed target image obtained by tomography apparatus according to exemplary embodiments of the present invention.

FIG. 34B is a reconstructed target image obtained by tomography apparatus according to exemplary embodiments.

Referring to FIG. 34B, reconstructed target image 3450 is reconstructed under the condition that X-ray detector has 128 detector raw rotation time, a rotation time is 300 ms and heart rate is 70 bpm. Referring to FIG. 34B, as shown in a region 3460, motion correction is effectively performed in the exemplary embodiments, and therefore coronary artery of heart in the reconstructed target image 410 is clearly imaged.

As described above, in the tomography apparatus according to the present invention and the tomography image reconstruction method thereof, an image with reduced motion artifacts may be reconstructed by using the raw data acquired while rotating by an angular section of one turn, that is, an angular section corresponding to an angle of 180°+an additional angle. Accordingly, compared to an amount of data needed for motion correction according to the related art, an amount of data for reconstructing a motion corrected image may be reduced to an amount of data corresponding to the angular section having an angle of 180°+fan angle, and the time for data acquisition may be reduced. Accordingly, the amount of X-rays irradiated toward a patient may be reduced.

Also, in the tomography apparatus according to the present invention and the tomography image reconstruction method thereof, as described above, a target image is reconstructed by acquiring information about motion of the object through the first and second images having a high temporal resolution, and thus a state of motion of the object may be accurately reflected and a target image having a high temporal resolution may be reconstructed. Also, as motion correction is effectively performed on a surface that is imaged by using the projection data acquired in the start angular section and the end angular section in the one-cycle angular section where blurring is most severely generated, a target image having a high temporal resolution may be reconstructed. Accordingly, an image with reduced motion artifacts may be reconstructed.

In addition, other embodiments of the present invention can also be implemented through computer readable code/ instructions in/on a medium, e.g., a computer readable medium, to control at least one processing element to implement any above described embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A tomography apparatus comprising:
at least one processor configured to:
obtain partial images of an object, wherein each of the partial images is obtained by using data acquired in an angular section which has an angle of less than 180° and is incomplete image showing a part of the object, the partial images comprising a first image and a second image that imaged a surface of a portion of the object in correspondence to a first time and a second time, respectively, by performing a tomography scan on the object that is moving,
obtain first information indicating motion of the object by comparing the surface of the portion of the object included in the first image with the surface of the portion of the object included in the second image, and
reconstruct a target image based on the first information.

2. The tomography apparatus of claim 1, wherein the first image and the second image are obtained by using data acquired in a first angular section and a second angular section, respectively, each of the first angular section and the second angular section having an angle value of less than 180°.

3. The tomography apparatus of claim 2, wherein the first information is acquired by comparing only the first image and the second image.

4. The tomography apparatus of claim 1, wherein the object imaged in the first image and the object imaged in the second image are different from each other in at least one from among a size, a position, and a shape.

5. The tomography apparatus of claim 1, wherein the first information comprises information indicating a motion amount of the surface of the portion of the object corresponding to time points between the first time and the second time, as information corresponding to a motion vector field between the first image and the second image.

6. The tomography apparatus of claim 2, wherein the at least one processor is further configured to perform the tomography scan in a one-cycle angular section that is less than one 360° turn,
the first angular section corresponds to a start section of the one-cycle angular section, and
the second angular section corresponds to an end section of the one-cycle angular section.

7. The tomography apparatus of claim 1, wherein the at least one processor is further configured to reconstruct the target image of the object at a target time between the first time and the second time, based on the first information.

8. The tomography apparatus of claim 7, wherein different time points are selected between the first time and the second time, and
a degree of a motion correction of the object included in the target image varies based on the target time selected to correspond to the different time points.

9. The tomography apparatus of claim 7, wherein the target time corresponds to a middle time between the first time and the second time, and
in the target image, a motion correction of the object is improved based on the target time selected to correspond to the middle time, as compared to the motion correction of the object when the target time does not correspond to the middle time.

10. The tomography apparatus of claim 1, further comprising:
a gantry comprising a rotating frame,
wherein the at least one processor is further configured to reconstruct the target image by using pieces of projection data corresponding to views that are raw data acquired by performing the tomography scan while rotating the rotating frame less than one 360° turn.

11. The tomography apparatus of claim 1, wherein the first information comprises information indicating a motion amount of the surface of the portion of the object during a period between the first time and the second time.

12. A method for reconstructing a tomography image, the method comprising:
obtaining partial images of an object, wherein each of the partial images is obtained by using data acquired in an angular section which has an angle of less than 180° and is incomplete image showing a part of the object, the partial images comprising a first image and a second image that imaged same portions of a surface forming the object and correspond to a first time and a second time, respectively, by performing a tomography scan on the object that is moving;
obtaining first information indicating a motion of the object, by comparing the surface of the portion of the included in the first image with the surface of the portion of the object included in the second image; and
reconstructing a target image based on the first information.

13. The method of claim 12, wherein the obtaining the partial images comprises:
obtaining the first image and the second image by using data acquired in a first angular section and a second angular section, respectively, each of the first angular section and the second angular section having an angle value less than 180°.

14. The method of claim 13, wherein the obtaining the first information comprises:
obtaining the first information by comparing only the first image and the second image.

15. The method of claim 12, wherein the object imaged in the first image and the object imaged in the second image are different from each other in at least one from among a size, a position, and a shape.

16. The method of claim 12, wherein the first information comprises information indicating a motion amount of the surface forming the object corresponding to time points between the first time and the second time, as information corresponding to a motion vector field between the first image and the second image.

17. The method of claim 13, wherein the obtaining the first image and the second image comprises performing the tomography scan in a one-cycle angular section that is less than one 360° turn,
the first angular section corresponds to a start section of the one-cycle angular section, and
the second angular section corresponds to an end section of the one-cycle angular section.

18. The method of claim 12, wherein the reconstructing the target image comprises:
reconstructing the target image of the object at a target time between the first time and the second time, based on the first information.

19. The method of claim 18, wherein different time points are selected between the first time and the second time, and
a degree of a motion correction of the object included in the target image varies based on the target time selected to correspond to the different time points.

20. The method of claim 18, wherein the target time is selected to correspond to a middle time between the first time and the second time, and
in the target image, a motion correction of the object is improved based on the target time selected to correspond to the middle time, as compared to the motion correction of the object when the target time does not correspond to the middle time.

21. The method of claim 12, wherein the reconstructing the target image comprises:
reconstructing the target image by using pieces of projection data corresponding to views that are raw data acquired by performing the tomography scan while rotating a rotating frame of a gantry less than one 360° turn.

22. The method of claim 12, wherein the first information comprises information indicating a motion amount of the surface of the object during a period between the first time and the second time.

23. A tomography apparatus comprising:
at least one processor configured to:
obtain a first image and a second image that are partial images of an object respectively corresponding to a first time and a second time and comprise same portions of surfaces forming the object, by performing a tomography scan on the object that is moving, wherein each of the first image and the second image is obtained by using data acquired in an angular section which has an angle of less than 180° and is incomplete image showing a part of the object,
obtain first information indicating a motion of the object by the surface of the portion of the object included in the second image, and
reconstruct a target image of the object at a target time, which is a time point between the first time and the second time, by warping at least one from among raw data needed for half reconstruction and an image acquired by performing filtered back-projection on the raw data, based on the first information,
wherein the first time is included in a first angular section and the second time is included in a second angular section that opposes the first angular section.

24. A tomography apparatus comprising:
at least one processor configured to:
obtain a first image and a second image that are partial images of an object, by using data acquired in a first angular section corresponding to a first time and a second angular section corresponding to a second time and facing the first angular section, by performing a tomography scan on the object, wherein each of the first image and the second image is obtained by using data acquired in an angular section which has an angle of less than 180° and is incomplete image showing a part of the object,
obtain first information indicating a motion amount of the object by comparing the surface of the portion of the object included in the first image with the surface of the portion of the object included in the second image; and
reconstruct a target image of the object at a target time, which is a time point between the first time and the second time, based on the first information.

25. A medical imaging apparatus comprising:
at least one processor configured to:
obtain a first image and a second image that are partial images of an object, by using data acquired in a first angular section corresponding to a first time and a second angular section corresponding to a second time and facing the first angular section, by performing a tomography scan on the object that is moving, wherein each of the first image and the second image is obtained by using data acquired in an angular section which has an angle of less than 180° and is incomplete image showing a part of the object,
obtain first information indicating a motion amount of the object by comparing the surface of the portion of the object included in the first image with the surface of the portion of the object included in the second image, and
reconstruct a target image of the object at a target time, which is a time point between the first time and the second time, based on the first information.

* * * * *